(12) United States Patent
Krukowski et al.

(10) Patent No.: US 12,102,387 B2
(45) Date of Patent: Oct. 1, 2024

(54) SYSTEM AND METHODS FOR USE IN VISION ASSESSMENT TO DETERMINE REFRACTIVE ERRORS AND NEURODEGENERATIVE DISORDERS BY OCULAR BIOMARKING FEATURES

(71) Applicant: RemmedVR Sp. z o.o., Warsaw (PL)

(72) Inventors: Piotr Krukowski, Warsaw (PL); Marek Piszczek, Warsaw (PL); Klaudia Borowczyk, Warsaw (PL); Dorota Maciaszek, Warsaw (PL); Marcin Maciejewski, Warsaw (PL); Mateusz Pomianek, Warsaw (PL)

(73) Assignee: RemmedVR Sp. Z.o.o., Warsaw (PL)

( * ) Notice: Subject to any disclaimer, the term of this patent is extended or adjusted under 35 U.S.C. 154(b) by 532 days.

(21) Appl. No.: 17/239,413

(22) Filed: Apr. 23, 2021

(65) Prior Publication Data

US 2021/0330185 A1 Oct. 28, 2021

Related U.S. Application Data

(60) Provisional application No. 63/015,059, filed on Apr. 24, 2020.

(51) Int. Cl.
*A61B 3/113* (2006.01)
*A61B 5/00* (2006.01)
(Continued)

(52) U.S. Cl.
CPC ............ *A61B 3/113* (2013.01); *A61B 5/4076* (2013.01); *G02B 26/0833* (2013.01);
(Continued)

(58) Field of Classification Search
CPC ....... A61B 3/10; A61B 3/113; A61B 5/44076; A61B 2562/028; A61B 3/1005;
(Continued)

(56) References Cited

U.S. PATENT DOCUMENTS

| 8,113,655 B1 | 2/2012 | Tyrin et al. |
| 9,386,921 B2 | 7/2016 | Cleveland |

(Continued)

FOREIGN PATENT DOCUMENTS

| CN | 102961117 A | 3/2013 |
| CN | 108937840 A | 12/2018 |

(Continued)

OTHER PUBLICATIONS

URL Only) https://www.youtube.com/watch?v=kAreDffuVCQ.

(Continued)

*Primary Examiner* — Christopher Stanford
*Assistant Examiner* — Journey F Sumlar
(74) *Attorney, Agent, or Firm* — Howard & Howard Attorneys PLLC

(57) ABSTRACT

A diagnostic device for use in performing refractive errors assessment and neurodegenerative disorders screening is described herein. The diagnostic device includes a display configure to render dynamically adjusted, dichoptic visual stimuli to a user, a varifocal optics system orientated between the display and the user's eyes, an ocular reflex analyzer emitting light signals towards the user's eye s and obtaining light signal reflected from selected part of the eye to measure eye accommodation during an on-going visual stimulation, and an eye tracking system configured to track movement of the user's eyes.

17 Claims, 34 Drawing Sheets

(51) Int. Cl.
  *G02B 26/08* (2006.01)
  *G02B 26/10* (2006.01)
  *G02F 1/29* (2006.01)
(52) U.S. Cl.
  CPC ............. *G02B 26/10* (2013.01); *G02F 1/294* (2021.01); *A61B 2562/028* (2013.01); *G02F 2202/30* (2013.01); *G02F 2203/11* (2013.01)
(58) Field of Classification Search
  CPC ..... A61B 3/107; A61B 3/1173; A61B 5/4082; A61B 5/4094; A61B 5/40; A61B 5/4005; G02F 1/294; G02F 2203/11; G02F 2202/30; G02B 26/0833
  See application file for complete search history.

(56) References Cited

U.S. PATENT DOCUMENTS

| | | | |
|---|---|---|---|
| 9,678,345 | B1 | 6/2017 | Melzer et al. |
| 9,706,910 | B1 | 7/2017 | Blaha et al. |
| 10,248,001 | B1 | 4/2019 | Lu et al. |
| 10,310,598 | B2 | 6/2019 | Trail et al. |
| 10,317,672 | B2 | 6/2019 | Sarkar |
| 10,326,977 | B1 | 6/2019 | Mercier et al. |
| 10,335,027 | B2 | 7/2019 | Pamplona et al. |
| 10,379,356 | B2 | 8/2019 | Nicholls et al. |
| 10,394,034 | B2 | 8/2019 | Reshidko et al. |
| 10,445,860 | B2 | 10/2019 | Fix et al. |
| 2011/0157550 | A1* | 6/2011 | Chen ............ A61B 3/145 351/246 |
| 2017/0112667 | A1 | 4/2017 | Fateh |
| 2017/0172406 | A1 | 6/2017 | Pamplona et al. |
| 2017/0293146 | A1 | 10/2017 | Nicholls et al. |
| 2017/0293356 | A1 | 10/2017 | Khaderi et al. |
| 2018/0196509 | A1* | 7/2018 | Trail ............ G02B 27/0172 |
| 2018/0210547 | A1 | 7/2018 | Sarkar |
| 2018/0263488 | A1 | 9/2018 | Pamplona et al. |
| 2019/0050051 | A1 | 2/2019 | Cirucci et al. |
| 2019/0082954 | A1 | 3/2019 | Kiderman et al. |
| 2019/0150727 | A1 | 5/2019 | Blaha et al. |
| 2019/0155046 | A1 | 5/2019 | Wall et al. |
| 2019/0250703 | A1 | 8/2019 | Price et al. |
| 2019/0250704 | A1 | 8/2019 | Price et al. |
| 2019/0290529 | A1 | 9/2019 | Park |
| 2021/0055792 | A1* | 2/2021 | Vostrikov ............ G06V 40/18 |

FOREIGN PATENT DOCUMENTS

| | | |
|---|---|---|
| CN | 109288493 A | 2/2019 |
| DE | 10 2015 217 682 A1 | 3/2017 |
| DK | 2506754 T3 | 12/2014 |
| KR | 10-2018-0083069 A | 7/2018 |
| KR | 10-2019-0026651 A | 3/2019 |
| KR | 10-2019-0062023 A | 6/2019 |
| TW | M525171 U | 7/2016 |
| WO | 2014/055600 A1 | 4/2014 |
| WO | 2017/181010 A1 | 10/2017 |
| WO | 2018/112254 A1 | 6/2018 |
| WO | 2018/203297 A1 | 11/2018 |
| WO | 2018/213010 A1 | 11/2018 |
| WO | 2019/109058 A1 | 6/2019 |

OTHER PUBLICATIONS

Robert G. Alexander et al., Microsaccade Characteristics in Neurological and Ophthalmic Disease, Frontiers in Neurology, Mar. 13, 2018, pp. 1-9, vol. 9, Article 144.

Fatimah Zara Javaid et al., Visual and Ocular Manifestations of Alzheimer's Disease and Their Use as Biomarkers for Diagnosis and Progression, Frontiers in Neurology, Apr. 19, 2016, pp. 1-11, vol. 7, Article 55.

CA Antoniades et al., Ocular motor abnormalities in neurodegenerative disorders, Cambridge Ophthalmological Symposium, Eye (2015) 29, 200-207, Macmillan Publishers Limited.

Elliott Hampsey et al., Microsaccade rate as a measure of drug response, Journal of Eye Movement Research, Oct. 3, 2019, pp. 1-20, 12(6):12.

A.B. Sereno et al., Executive Functions: Eye Movements and Human Neurological Disorders, Encyclopedia of Neuroscience, 2009, pp. 117-122, https://doi.org/10.1016/B978-0-12-809324-5.02099-X, ScienceDirect, Elsevier Inc.

Mattias Nilsson Benfatto et al., Screening for Dyslexia Using Eye Tracking during Reading, Journal.pone, Dec. 9, 2016, pp. 1-16, PLoS One.

Ehud Ahissar et al., On the possible roles of microsaccades and drifts in visual perception, ScienceDirect, Vision Research 118 (2016), pp. 25-30, Elsevier Ltd.

J. M. Findlay, Frequency analysis of human involuntary eye movement, Kybernetik 8, Jun. 1971, pp. 207-214, https://link.springer.com/article/10.1007%2FBF00288749#citeas, SpringerLink.

Christoph Klein et al., An Introduction to its Scientific Foundations and Applications, Eye Movement Research, https://link.springer.com/book/10.1007%2F978-3-030-20085-5#about, SpringerLink.

Uzma Samadani et al., Sensitivity and specificity of an eye movement tracking-based biomarker for concussion, Future Science Group, Aug. 6, 2015, pp. 1-14.

Roberto Rodriguez-Labrada et al., Eye Movement Abnormalities in Neurodegenerative Diseases, IntechOpen, Jan. 25, 2019, 17 pages, https://doi.org/10.5772/intechopen.81948.

Kentaro Morita, MD, et al., Eye Movement as a biomarker of schizophreniz: Using an integrated eye movement score, Psychiatry and Clinical Neurosciences, 2017, pp. 104-114, 71, The Authors.

Ilya Obyedkov et al., Saccadic eye movements in different dimensions of schizophrenia and in clinical high-risk state of psychosis, BMC Psychiatry, 2019, pp. 1-10, 19:110, The Authors.

Christy K. Sheehy et al., Fixational microsaccades: A quantitative and objective measure of disability in multiple sclerosis, Multiple Sclerosis Journal, Feb. 7, 2020, 7 pages, https://doi.org/10.1177%2F1352458519894712, SAGE Publications Inc.

Marion Charvin, MD et al., Botulinum Toxin A for Chronic Exertional Compartment Syndrome, a Retrospective Study of 16 Upper- and Lower-Limb Cases, Clinical Journal of Sports Medicine, Jul. 16, 2021, 4 pages, https://doi.org/10.1097/JSM.0000000000000731.

Rebecca S. Braveman, MD, Introduction to Amblyopia, America Academy of Ophthalmology, Oct. 21, 2015, 3 pages, https://www.aao.org/disease-review/amblyopia-introduction.

https://www.hamamatsu.com/eu/en/product/type/S13989-01H/index.html.

Neil Sarkar (AdHawk Microsystems): Ultra-Fast Eye Tracking Without Cameras for Mobile AR Headsets, https://www.slideshare.net/AugmentedWorldExpo/neil-sarkar-adhawk-microsystems-ultrafast-eye-tracking-without-cameras-for-mobile-ar-headsets.

Joon-Suh Park et al., All-Glass, Large Metalens at Visible Wavelength Using Deep-Ultraviolet Projection Lithography, ACS Publications, Nov. 14, 2019, pp. 8673-8682, 19, 12, American Chemical Society, https://pubs.acs.org/doi/10.1021/acs.nanolett.9b03333.

Alan She et al., Adaptive metalenses with simultaneous electrical control of focal length, astigmatism, and shift, Science Advances, Feb. 23, 2018, pp. 1-7, The Authors.

Zhenyu Yang et al., Generalized Hartmann-Shack array of dielectric metalens sub-arrays for polarimetric beam profiling, Nature Communications, 2018, pp. 1-7, 9:4607, The Authors.

\* cited by examiner

| Parameter | VR optics B2C/B2B | Remmed optics |
|---|---|---|
| Accommodative stimuli zone | Range between 40-50cm and infinity (best case, probably will much more limited). | Range between 5cm and infinity. |
| Gaze-depending | Best if doesn't depend on the gaze point. | Focal plan is changing for the whole scene depending on therapeutic scenario, often without gaze input. As we don't require zero-latency, gaze-depending is not an issue. |
| Mode | Depth planes set at one time simultaneously. Could possibly support jumps mode. | Continuous and jump mode required. Active optics are not an issue. |
| Latency | Strong need for zero-latency passive system. | No need for zero-latency. |
| Number of planes | Finite number of depth planes with limited range of virtual distance (enough for regular use). | Unlimited number of depth planes or much higher limit. |
| Separate depth planes for the left and the right eye | No needed. | Yes. |
| Production Cost | Must suit B2C/B2B price points and keep compromise between value and end-price. | Specific use cases in healthcare sector doesn't require substantial cost cut. |

FIG. 17

Analysis of real and synthesized image data in MATLAB environment

Simulation of the waveform as a function of sampling frequency

| Movement disorders | Delayed saccade initiation | Slow saccadic velocity | Hypermetric saccades | Hypometric saccades | Square wave jerks | Saccadic intrusions during pursuit |
|---|---|---|---|---|---|---|
| *Hypokinetic* | | | | | | |
| PD[1] | | | | +[2] | | |
| MSA | | | + | + | +[3] | + |
| PSP[2] | | +[5] | | +[5] | +[6] | |
| CBD | + | +[7] | | | | |
| *Hyperkinetic* | | | | | | |
| *Myoclonus* | | | | | | |
| *Chorea* | | | | | | |
| OMAS | | | | | | +[8] |
| HD[9] | + | + | | | | |
| Neuroacanthocytosis[10] | + | + | | | | |

FIG. 35

| Table 1 \| Eye movement abnormalities in neurodegenerative disorders | | |
|---|---|---|
| Neurodegenerative disorder | Eye movement characteristics found in the clinic | Eye movements recorded in the laboratory |
| Lewy body parkinsonian diseases | | |
| Parkinson disease | Mild hypometria of upwards voluntary saccades; Mildly impaired smooth pursuit | ↓ Gain (hypometria) of voluntary saccades |
| Parkinson disease dementia | Not reported | ↑ Latency and ↓ gain of reflexive and (particularly) voluntary saccades; ↑ Antisaccade errors |
| Dementia with Lewy bodies | Supranuclear gaze palsy in some patients (case reports) | ↑ Latency of reflexive and voluntary saccades; ↓ Saccade prediction; ↑ Antisaccade errors; ↓ Express saccades (in the gap task) |
| Huntington disease | | |
| Symptomatic patients | Apraxia of saccades (difficulty with initiation) with or without head thrusting; Slow saccades, especially in patients with young age at onset; Gaze distractibility and impersistence | ↑ Saccade latency; ↑ Variability of saccade latency; ↓ Saccade velocity; ↑ Directional and timing errors of antisaccades and memory-guided saccades; Distractibility during smooth pursuit |
| Presymptomatic patients | Normal | ↑ Saccade latency; ↑ Variability of saccade latency; ↑ Antisaccade and memory-guided saccade errors |
| Dementia | | |
| FTD | Not reported, but patients who progress to PSP or corticobasal syndrome exhibit eye movement abnormalities characteristic of those disorders | Normal reflexive saccades; ↑ Antisaccade errors (in patients with behavioural variant FTD and PNFA) that are corrected normally; Normal antisaccades (in patients with semantic dementia) |
| Alzheimer disease | Impaired visual grasp reflex on clinical antisaccade test | ↑ Fixation instability; ↑ Latency of reflexive and voluntary saccades; ↑ Antisaccade errors; ↓ Correction of antisaccade errors |
| Abbreviations: FTD, frontotemporal dementia; PNFA, progressive nonfluent aphasia; PSP, progressive supranuclear palsy. | | |

FIG. 36

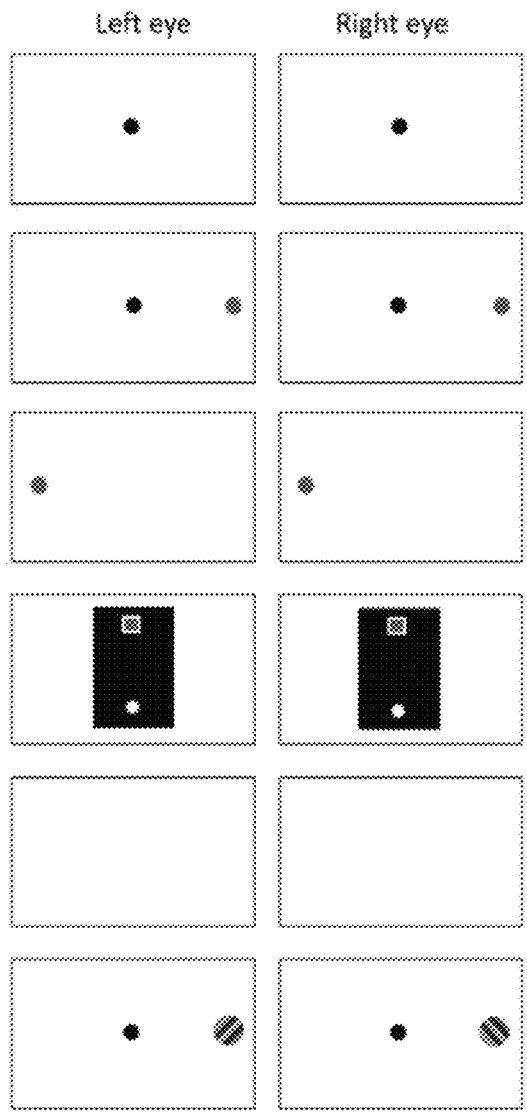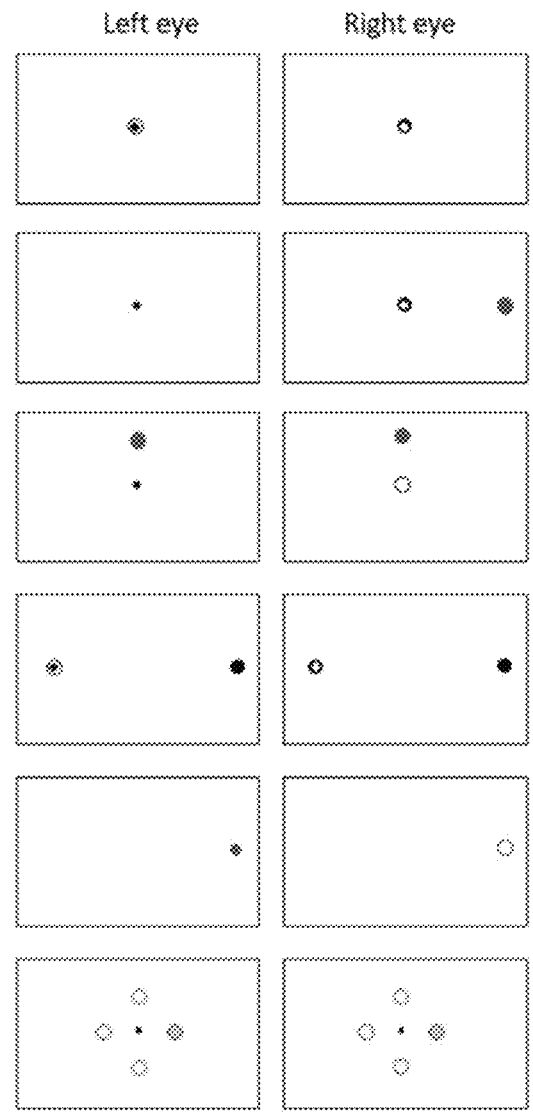
FIG. 37                    FIG. 38

SYSTEM AND METHODS FOR USE IN VISION ASSESSMENT TO DETERMINE REFRACTIVE ERRORS AND NEURODEGENERATIVE DISORDERS BY OCULAR BIOMARKING FEATURES

CROSS-REFERENCE TO RELATED APPLICATION

This application claims the benefit of U.S. Provisional Patent Application Ser. No. 63/015,059, filed Apr. 24, 2020, the disclosure of which is hereby incorporated by reference in its entirety.

TECHNICAL FIELD

The present invention relates to vision assessment and therapy and to systems and methods for the precise analysis of eye movements (-micro and -macro scale of temporal and spatial parameters) conducted during the displaying of visual, dynamic stimuli including dichoptic projection features and controlled, variable optical conditions adjusted separately for each eye. Purpose of these is to implement refractive errors eye exam augmented with neurodegenerative disorders (NDD) focused screening conducted under single system.

BACKGROUND OF THE INVENTION

Many people suffer from neurodegenerative diseases such as Alzheimer and Parkinson. In addition to the unquestioned pain of lost health and lives of individuals, this group of disorders carries a huge economic cost that is ultimately borne by entire societies. Early detection of neurodegenerative disorders can save $230 B a year in the US only in direct treatment and long-term care costs. Today there is no affordable, non-invasive, objective screening solution that can be provided to everyone over the age of 40. Known prodromal (neurodegenerative diseases) NDD screening method characteristics (currently) include: expensive screening (mostly based on MRI/PET findings); inaccessibility (provided by specialized care units); symptoms occur individual (there is no single, visible syndrome suiting all the cases); unharmonized criteria (most of the markers are nonspecific, science is on early stage of knowledge development); and Low social awareness (symptoms may be interpreted as normal aging). Which lead to the following: 1) Detecting prodromal PD (Parkinson's disease) is relatively uncommon, with prevalence estimates ranging from 0.5-4%; 2) One of the greatest current challenges is to identify markers for prodromal disease stages, which would allow novel disease-modifying therapies to be started earlier; 3) Global data indicate that PD will become a pandemic: prevalence more than doubled between 1990 and 2015, and PD now affects 6.2 million individuals; 4) Projected PD prevalence (US) will be more than 1.6 million with projected total economic burden surpassing $79 billion by 2037, and the economic burden of PD was previously underestimated; 5) The cost of AD (Alzheimer's disease) now rivals that of cancer and heart disease, but the growing epidemic of AD means that these costs will race ahead of the costs of other diseases in the coming years; thus, by 2050, it is predicted that 16 million Americans will have AD, resulting in $1 trillion per year in expenses to Medicare and Medicaid alone; and 6) Given our aging population, AD represents a looming public health crisis. The development of novel medical devices for AD treatment or detection requires the combined expertise and resources of many different research projects.

According to various studies, approximately 54 percent of U.S. adults said they visit or consult an optometrist/ophthalmologist (eye care doctors) at least once a year, which creates perfect conditions to supplement with additional set of screening tests focused on NDDs.

However, refractive errors exam are burdened with following issues: 1) Assessment requires 20 ft examination space, expensive equipment, and it is not reimbursed; 2) Inconsistent prescription results are the norm in eyecare as it relies on different OD/MD each time combined with patient declarative subjective judgment; 3) High cost of qualified personnel (average optometrist salary may exceed ~110.000 USD/year); and 4) Possible human error caused by lack of unified procedures, lack of objective data or lack of proper education.

Up to 5% of minors in a worldwide population who have problems with lazy eye or crossed eyes. Untreated, or not properly treated those conditions are likely to further adversely affect minor's binocular vision disorders, stereo-deficiency, learning abilities, motoric skills and willingness to socialize, which may lead to low self-esteem, disabilities and depression in such a minor's adult life. At least some known vision treatment therapies require the patient to attend vision therapy sessions at a clinic or therapists office, which may be difficult for patients to attend and receive consistent and frequent treatments. Also, traditional vision therapy tools are obsolete, with hard to follow treatment procedures. According to some studies, a prevalence of approximately 10% accommodation and convergence related disorders has been observed in schoolchildren, and that visual discomfort is also common among teenagers who carry these conditions (such as headaches and loss of concentration). Moreover, stereo deficiency may limit career options for patients with binocular vision disorders.

The present invention is aimed at one or more of the problems identified above.

SUMMARY OF INVENTION

In one aspect of the present invention, a diagnostic device for use in performing refractive errors assessment and neurodegenerative disorders screening is provided. The diagnostic device includes a display configure to render dynamically adjusted, dichoptic visual stimuli to a user, a varifocal optics system orientated between the display and the user's eyes, an ocular reflex analyzer emitting light signals towards the user's eye s and obtaining light signal reflected from selected part of the eye to measure eye accommodation during an on-going visual stimulation, and an eye tracking system configured to track movement of the user's eyes.

In another aspect of the present invention, a method of operating a diagnostic device for performing a neurodegenerative disease screening exam is provided. The diagnostic device includes a display configure to render dynamically adjusted, dichoptic or binocular visual stimuli to a user, a varifocal optics system orientated between the display and the user's eyes, an eye tracking system configured to track movement of the user's eyes, and a processor. The method includes the processor executing the algorithm steps of: adjusting the varifocal optics system to an initial refractive correction, displaying visual stimuli on the display based on desired test procedure, collecting eye movement data using eye tracking system, and determining neurodegenerative disease by comparing collected eye movement data with baseline eye movement data associated with desired test scenario.

In yet another aspect of the present invention, a method of operating a diagnostic device for performing a refractive errors assessment is provided. The diagnostic device including a display configure to render dynamically adjusted, dichoptic visual stimuli to a user, a varifocal optics system orientated between the display and the user's eyes, an ocular reflex analyzer emitting light signals towards the user's eye s and obtaining light signal reflected from selected part of the eye to measure eye accommodation during an on-going visual stimulation, an eye tracking system configured to track movement of the user's eyes, and a processor. The method including the processor executing the algorithm steps of: displaying visual stimuli on the display based on desired refractive errors assessment test procedure, collecting eye movement data using eye tracking system, collecting ocular accommodation data using the ocular reflex analyzer, and determining best refractive correction and ocular behavior based on collected eye movement data and ocular behavior data.

BRIEF DESCRIPTION OF DRAWINGS

Non-limiting and non-exhaustive embodiments of the present invention are described with reference to the following figures. Other advantages of the present disclosure will be readily appreciated, as the same becomes better understood by reference to the following detailed description when considered in connection with the accompanying drawings wherein:

FIG. 17 is a table that includes a summary of at least some benefits of the system shown in FIG. 1;

FIGS. 35 and 36 are illustrations of exemplary data files that may be generated by the system shown in FIGS. 3 and 18;

FIGS. 37-41 are illustrations of images that may be displayed by the head-mounted display unit;

Corresponding reference characters indicate corresponding components throughout the several views of the drawings.

DETAILED DESCRIPTION OF THE INVENTION

Figure 1:
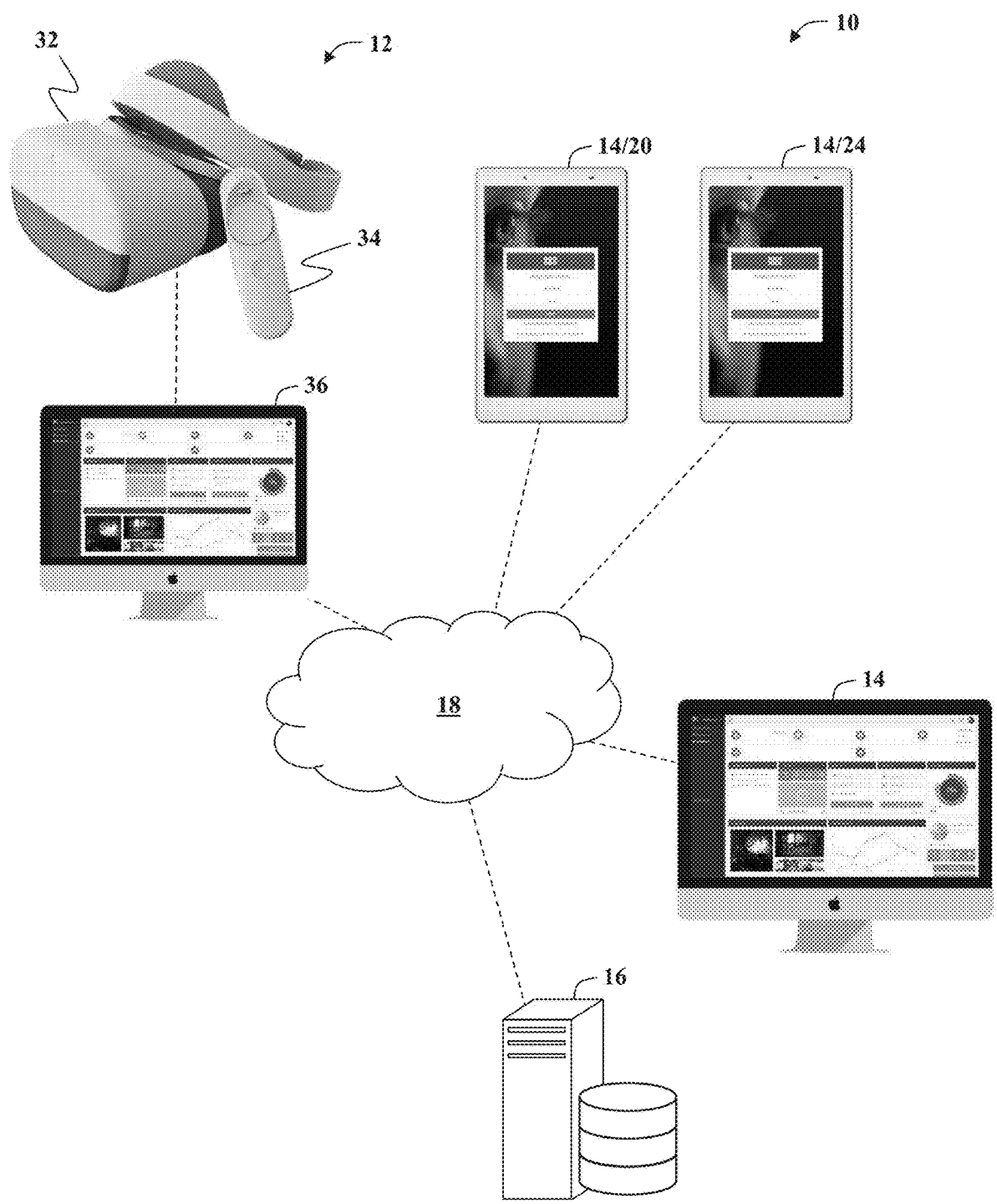
FIGS. 1 and 2 are schematic diagrams of a system including a vision assessment and therapy device for use in vision assessment and therapy, according to embodiments of the present invention.
Figure 2:
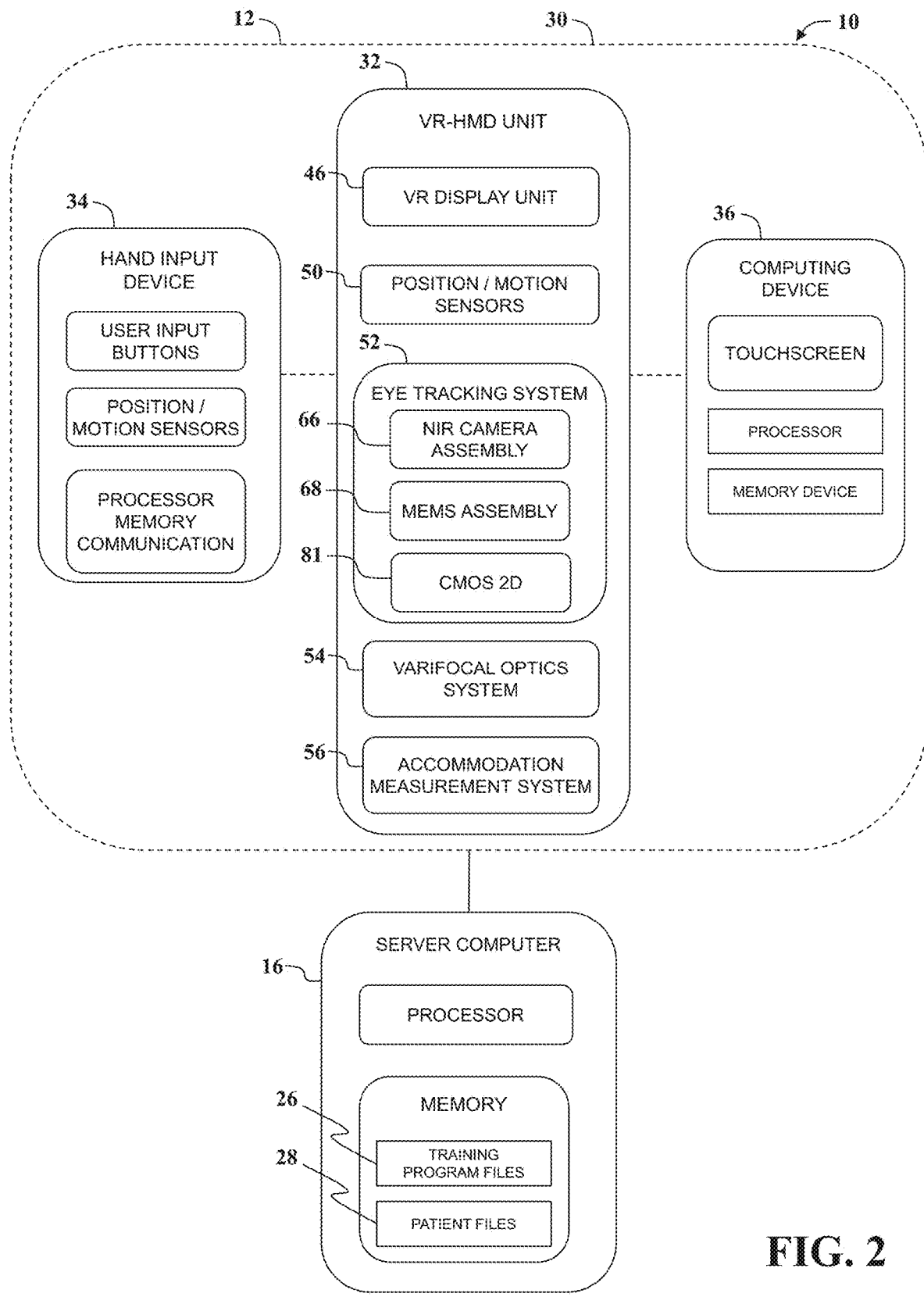
Figure 3:
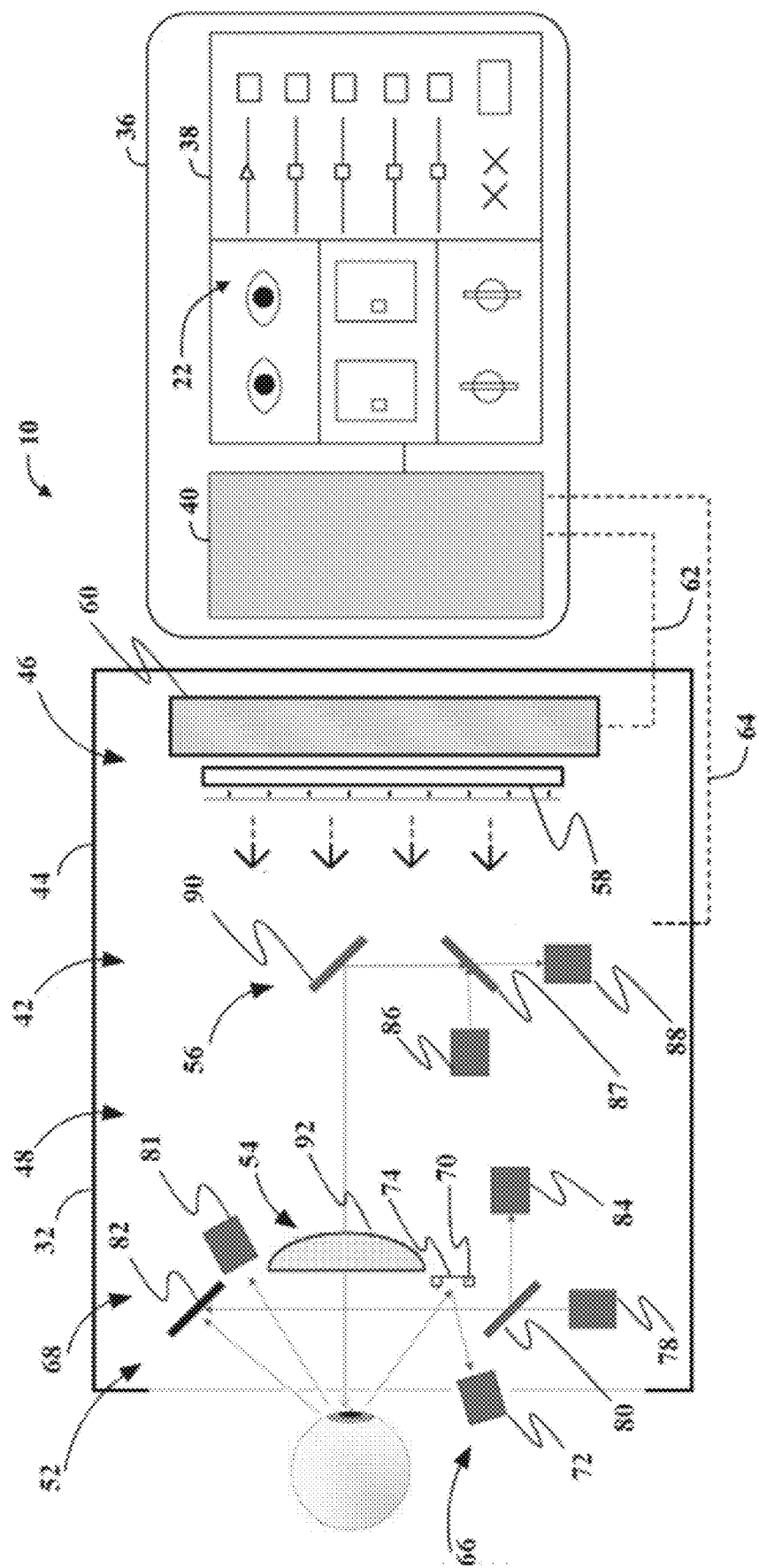
FIG. 3 is a schematic diagram of the vision assessment and therapy device including a head-mounted display unit, according to embodiments of the present invention.

Embodiments of the present invention includes a diagnostic device and methods utilizing physical eye response obtained during projected visual stimuli is provided. The device is configured to collect comprehensive sets of data used to analyze temporal and spatial parameters of eye movements within high resolution and physical features (e.g. retinal reflex).

The present invention relates to the methods and device for the precise analysis of eye movements (-micro and -macro scale of temporal and spatial parameters) performed during displayed visual, dynamic stimuli including dichoptic projection features and controlled, variable optical conditions provided separately for each eye. Disclosed set of modules mounted within a single diagnostic device that has operating software installed is designed to perform refractive errors eye exam augmented with neurodegenerative disorders (NDD) screening or diagnosis, conducted under a single system, in a fully automated way.

The device combines novel eye tracking methods implementing bi-modular design wherein 1) MEMS mirrors based eye tracking aims to provide spatial orientated data in the first place, and 2) 2D-profile sensor eye tracking is used to obtain temporal class data. Data acquisition model based on mentioned modules creates perfect conditions to achieve unattainable today level of data quality. Crucial part leading to this goal is unique optoelectronic design bundled with analytical software using e.g. ML methods.

Second part contributing to the main objectives is to provide dynamic visual stimuli displayed under binocular or dichoptic conditions under variable optical states assigned separately to each eye. This section is designed on the basis of the virtual reality concepts, however the approach is distinct in several aspects. The first one is related to general device form. The present invention may include stationary device determining sitting position of the user and simultaneous face brining directly to the device optical system which excludes common HMD approach related to VR industry. Additionally, varifocal optics used within disclosed device is different than state-of-the-art optics connected to VR headsets which is dictated by another use case and business sector needs.

Data acquisition model is also enhanced by Ocular Reflex Analyzer configured to obtain parameters describing, for example, accommodative state of the eye or astigmatism type and level. This output is used to impact refractive assessment process quality.

The combination of these modules within one system creates a perfect system to be implemented under use cases: refractive errors exam and NDD focused screening. Basic method executed during the assessment is to iteratively display scenario-determined, dynamic visual stimulus under variable optical conditions aiming to evoke selected eye movements. Loop is stopped once system determines that obtained data quality reached right threshold.

The present invention includes systems and methods for refractive errors assessment and NDDs (neurodegenerative diseases) screening based on eye movement abnormalities profiling are disclosed. The ultimate goal of the present invention is to simultaneously provide refractive errors determination and NDD screening tests. The present invention addresses the problems of two healthcare sectors: eye care and neurology. This combination has its grounds in the following aspects: 1) There is high public awareness for regular eye examinations. In comparison, screening tests targeting neurodegenerative disorders are expensive and inaccessible. By combining these two tests in a single device, the present invention breaks the barrier of availability and cost. The present invention makes it possible to perform NDD focused screening package during the accessible refraction test (which most of the people is aware of). The present invention aims to extend the popular refractive exams with NDD screening package. Thus, present invention enables to scale NDD screening accessibility in a way that is non-invasive to the patient and the health care system. The system does not require development of dedicated sales channels as the present invention leverages the popularity of the eye exams. The present invention helps reach a vast group of people, which is crucial to address huge social pain related to NDDs. 2) Additionally, the present invention allows for full automation of the assessment process, excluding potential human error and enabling the possibility of implementation entirely new models of care delivery that do not require presence of a specialist during the exam. 3) Sharing components for two applications allows for lowering the costs of implementation resulting with reasonable end-price, which also positively influences availability.

In general, the present invention describes a system that includes unique and novel combination of modules: varifocal optics, ocular reflex analyzer, MEMS eye tracking and 2D sensor profile eye tracking configured to perform NDD-focused screening tests and refractive errors exam within a single device, without specialized care provided (e.g. optometrist). The Refraction main features (simultaneous presence) include: a) Providing dichoptic visual stimuli within various and controllable depth distance according to set test scenario, b) Visual acuity and refractive errors determination based on ocular micro-movements behavior paired to set optical conditions in varifocal optics module, c) Controlling accommodation response to various optical states indicating if accommodation is relaxed, and d) During the assessment, utilizing unique combination of modules: varifocal optics, ocular reflex analyzer, 1ViEMS eye tracking, and 2D sensor profile eye tracking. The system includes NDD main features (simultaneous presence) including: a) Providing dichoptic visual stimuli within various and controllable depth distance according to set test scenario, b) Assessment of possible NDD development based on micro-movements behavior with the use of MEMS/2D-profile eye tracking, and c) During the assessment, utilizing unique combination of modules: varifocal optics, MEMS/2D-profile eye tracking. The system MEMS eye tracking method consisting of features including: a) Determining eye movement data through defining pupil and iris intersection points on analyzed Lissajous pattern. The 2D profile sensor (CMOS) eye tracking module configured to determine temporal features of eye movements (like latency). The system also increases the accuracy of the eye tracking data by excluding necessity of wearing corrective glasses, by implementing methods using varifocal optics.

In addition, the present invention includes a system that offers perfect conditions for conducting comprehensive NDD-focused screening test package. The device follows a concept of 'eye as a biomarker'

In addition, the present invention includes a system and methods for use in visual assessment and therapy extended by biomarking features. The system includes a head-mounted display (HMD) with built-in varifocal optics, at least one eye tracking module, and accommodation measurement module for vision assessment and therapy. Eye tracking module may act also as an ocular movement biomarking sensor.

In terms of vision assessment, the system also includes the possibility of refractive errors examination done in objective and subjective model in reference set depth plan with controlled accommodation stimuli and response. It means, that presented system covers eye care field nowadays conducted with the use of phoropters and autorefractors. Moreover, system capabilities presented below allow to implement an assessment methods for neuro-related diseases such as Parkinson's disease, Alzheimer's disease, Schizophrenia, Multiple Sclerosis, Concussion, mTBI, CTE, Dementia with Lewy-Bodies, Frontotemporal Dementia, Corticobasal Degeneration, Huntington's Disease, Multiple System Atrophy, Progressive Supranuclear Palsy, Dyslexia, ADHD, Bipoloar disorder, Autism spectrum disorder based on ocular movement behavior analytics (provided by presented eye tracking technology) in relation to generated visual environment with controlled accommodation stimuli and response.

The system 10 unifies all the techniques of therapy and diagnostics of binocular vision known today, extending them to include objective measurement methods. The system can perform exercises and activities at set depth plan by controlling accommodation stimuli separately to left and right eye in range of Near Point of Convergence, Near Point of Accommodation (5-6 cm) and relaxed ocular vergence and accommodation state (3-5 m). The system allows for customized treatment plans on an ongoing basis, based on objective data collected, which enables a more accurate selection of the training plan modified during its implementation. Binocular vision is a complex process consisting of many parameters. The system enables analysis of a plurality of vision parameters at the same time, thus providing the possibility of conducting therapy directed at each parameter. Vision care specialists have to conduct vision training and diagnosis in the close to natural visual conditions that can be parametrized and recurrent. Combination of VR environment with proposed modules is crucial to achieve this goal. Moreover, the system 10 is able to conduct subjective and objective refractive errors assessment.

Based on unique data collection modules and an AI driven core, the system 10 is capable of substituting or augmenting human engagement in any kind of vision assessment and therapy procedures. This is especially important in markets, where access to a well-qualified specialist is very limited. It also eliminates human error which is a common problem even on mature markets. Quality of eye care services depends on skills of specialists which require many years of education.

The system 10 consists of following major components:

1) Projection system based on varifocal optics and VR display that provides controlled depth perception visual cues in a full range of ocular abilities—from NPC (Near Point of Convergence) and NPA (Near point of Accommodation) to relaxed ocular vergence and accommodation state. B2C/B2C market focuses on solving Vergence-Accommodation-Conflict (VAC). The system 10 includes optical design to answer to much wider requirements than solving VAC, for example, to provide accommodation visual stimuli separated from convergence stimuli provided independently to the left and right eye. The system 10 implements different optical design in comparison to known solutions including Oculus™ in Half Dome prototypes. For example, FIG. 17 illustrates the differences between approach implemented by the system 10 ("Remmed optics") and regular B2C/B2B VR headsets in terms of optical design. Leading concept for this module is to implement varifocal metalenses capable of manipulating with cylindrical axis and spherical power, which will be important especially during subjective refractive errors assessment.

2) Eye tracking module able to analyze ocular movements in frequency up to 1000 Hz and accuracy 1 arcmin (including saccades, micro-saccades). Known eye tracking modules are based on NIR cameras, proper lighting, bulky head-mounting and image processing, which leads to limited accuracy and frequency of tracking and high computing power demands. Moreover, the highest data quality of known system could be only obtained by scientific grade equipment that costs over 30-50.000 USD. The system 10 is configured to implement the following approaches: 1) MEMS based eye tracking (bi-resonant or one line linear and second resonant); and 2) MEMS based eye tracking (bi-resonant or one line linear and second resonant) empowered by pupil position estimation coordinates provided by CMOS 2D profile used to narrowing MEMS operating area for higher density of tracking data points. In defined scenarios, estimation of pupil position can be realized by visual activity (training or diagnostic) scenario and displayed content without involvement of an additional sensor such as CMOS 2D profile sensor. For instance, system could indicate pupil position if visual activity scenario includes some predictable eye movements like smooth pursuits, saccades, fixation stability in relation to displayed objects in VR environment. Based on this input, system can limit maximum angle of MEMS mirror swing and actuate entry base position of the MEMS mirror according to estimated position of the pupil given by the scenario and content. Actuation of entry base zero point of MEMS (initial position) can be done by MEMS module itself or it can be realized by an external actuator combined with MEMS module based on: VR content and/or scenario of activity and/or 2D CMOS profile sensor. Mentioned options may also be supplied with traditional NIR/camera imaging enabling an eye specialist to observe eye movements and alignment as a safety preview executed during a stationary session.

3) Ocular accommodative response measurement module based on Shack-Hartmann wavefront sensors and/or automated retinoscopy method. It is very specific module directly correlating with use cases. Module is needed as an objective feedback describing ocular response to given depth stimuli. Based on the accommodation response, the system 10 could automate therapeutic scenarios. There is no need to implement such a solution in known B2C/B2B headsets, as the market value would be too minor in comparison to the increased production cost and therefore increased price. However, it brings significant value in vision therapy and diagnosis field. Module may act also as a method for objective refractive error measurement.

The system 10 includes a unique, novel combination of projection and measurement modules based on VR technology, which is different from other known approaches presented by e.g., Oculus™ or any other scientific publication.

The system 10 provides vision assessment tests including: 1) Visual acuity to the distance, near and intermediate distances; 2) Suppression assessment to the distance, near and intermediate distances; 3) Stereopsis to the distance, near and intermediate distances ; 4) Eye-movements to the distance, near and intermediate distances; 5) Eye alignment assessment to the distance, near and intermediate distances; 6) Binocular vision parameters to the distance, near and intermediate distances (simultaneous perception, fusion, stereopsis, vergence ranges, near point of convergence); 7) Fixation test; 8) Accommodation determination for distance, near and intermediate distances (measurements of the near point of convergence (NPC), amplitude of accommodation (AA), monocular and binocular accommodative facility (MAF and BAF) and negative and positive relative accommodation (NRA and PRA); and 9) subjective and objective refractive error measurement.

The system 10 also provides therapeutic methods including: 1) Therapy of eye movement disorders; 2) Therapy of unilateral vision impairment (amblyopia), binocularly reduced visual acuity, or low vision; 3) Insufficient convergence, excessive convergence, insufficient divergence, excessive divergence, intermittent strabismus, alternating strabismus and constants strabismus; 4) Therapy of interocular suppression in strabismus disorders (tropia) and in amblyopia; 5) Developing of motor and sensory fusion, stabilization of fusion, development of stereopsis; 6) Accommodation training in case of spasmodic accommodation, inefficient accommodation, insufficient accommodation; and 7) Training of visual-motor coordination.

The system 10 is capable of conducting refractive errors assessment (myopia, hypermetropia, astigmatism) done in subjective and objective model. Shack-Hartmann or an automated sciascopy module can provide objective data determining ocular refractive errors collected on accommodation relaxed state provided by varifocal virtual stimuli set on defined depth plan. Subjective model of an assessment can be done based on metalens varifocal optics capable of adopting its spherical power and cylindrical axis driven by an electric signal generated by the system. This task can be also executed by other types of varifocal optics including, for example, sets of movable lenses combined with linear movement mechanisms. Subjective test is based on user input determining iteratively comfort of visual perception and ability of optotype recognition. During mentioned iteration, varifocal optical system provides with different optical states as a simulation of corrective glasses lenses or contact lenses. Iteration is finished once system will assess that smallest possible angular size of an optotype can be recognized by a user in relation to current optical power of the varifocal optics. Based on subjectively assessed settings of varifocal optics system generates proper prescription for corrective glasses or lenses including results. System may include automated preferential looking tests thus objectivize subjective tests measuring smallest perceived spatial resolution. Controlling of ocular accommodation response may be an important input during the assessment. Described system capabilities may substitute currently implemented equipment necessary to refractive errors assessment such as: phoropter, autorefractor, 15-20 ft long office.

Referring to FIGS. 1-11, in the illustrated embodiment, the system 10 includes a vision assessment and therapy device 12, one or more user computing devices 14, and server system 16. The vision assessment and therapy device 12, user computing devices 14, and server system 16 communicate via a communications network 18 The communications network 18 may be any suitable connection, including the Internet, file transfer protocol (FTP), an Intranet, LAN, a virtual private network (VPN), cellular networks, etc. . . . , and may utilize any suitable or combination of technologies including, but not limited to wired and wireless connections, always on connections, connections made periodically, and connections made as needed.

Each user computing device 14 includes a display device and a processing device that includes a processor that is coupled to a memory device. For instance, main control-managing set provided to eye doctors could consist of 20-25" touch display (e.g., MONITOR LED HANNS-G HT225HPB) with an Android/PC box (e.g., X96 MAX) plugged into HDMI port that will run control panel application interface during stationary sessions. If a device works in remote mode where it is rented to patient's home—a regular PC tablet or smartphone is sufficient for safety assessment done by parents (in case if a patient is a child). The processing device executes various programs, and thereby controls components of the computing device according to user instructions received by the user to enable the user to access and communicate with the system 10 including sending and/or receiving information to and from the vision assessment and therapy device 12 and/or server system 16 and displaying information received from the vision assessment and therapy device 12 and/or server system 16. The user computing devices 14 may include, but is not limited to, a desktop computer, a laptop or notebook computer, a tablet computer, smartphone/tablet computer hybrid, a personal data assistant, a handheld mobile device including a smartphone, and the like. For example, in some embodiments, the system 10 may include a therapist tablet 20 including a tablet computer equipped with a built-in LTE modem and an active SIM card for providing a vison therapist access to the vision assessment and therapy device 12 and/or server system 16. The therapist tablet 20 may include as a web-based tool accessible via an Internet browser that displays a control panel 22 (shown in FIG. 3) that enable control and therapy settings adjustment for use in operating the vision assessment and therapy device 12 to provide vision therapy to a patient. The system 10 may also include a parent/guardian tablet 24 that includes a tablet computer equipped with a built-in LTE modem and an active SIM card for communicating with the vision assessment and therapy device 12 to provide an external display screen for the vision assessment and therapy device 12 to allow a parent/guardian to view images being displayed by the vision assessment and therapy device 12.

The server system 16 includes a server computer including a processor that is coupled to a memory device for executes various programs being stored on the memory device. The memory device may include a plurality of vision assessment and training program files 26 that include object data and instructions for executing and displaying various vision assessment and training sessions via the vision assessment and therapy device 12. Each vision assessment and training program file 26 may include information for displaying training games (shown in FIGS. 8-11) displayed in a virtual reality environment in a controlled depth plan that require the patient to perform a series of game related tasks in order to advance game play.

The vision assessment and training program files 26 may include information associated with visual properties such as intensity of dominant eye occlusion (optional auto level function), intensity of amblyopic eye stimulation (optional auto level function), ocular accommodation response, ocular motor behaviors including map of saccades and microsaccades, and intensity of binocular stimulation (optional auto level function) for each training game. The server computer 16 may also be programmed to allow a vision therapist to access the vision assessment and training program files 26 via the therapist tablet 20 to select one or more training games, customize the visual properties associated with each training game, and generate training programs that may be downloaded to the vision assessment and therapy device 12 including instructions for executing and displaying the customized training games to a patient.

The server computer 16 may also generate and store patient progress files 28 that include information associated with a patient including associated customized training programs, and progress information associated with a patient's use of the vision assessment and therapy device 12

In the illustrated embodiment, the vision assessment and therapy device 12 includes a Mobile virtual reality (VR) device 30 including a virtual reality head mounted display (VR-HMD) unit 32, a hand-held control device 34, and an external computing device 36. In one embodiment, the computing device 36 may be an externally plugged computing box. In other embodiments, the computing device 36 may be a user computing device 14 such as, for example the therapist tablet.

In the illustrated embodiment, the external computing device 36 includes a touchscreen display 38 and a controller 40 coupled to the touchscreen display 38. The controller 40 includes a memory device and a processor programmed to execute computer instructions including the training programs for use in displaying the visual training games to the patient using the VR-HMD unit 32. The touchscreen display 38 displays the control panel 22 to enable a therapy or diagnosis specialist to control the vision assessment and therapy device 12.

The hand-held control device 34 includes a plurality of position/motion sensors such as, for example accelerometer sensors, gyro sensors, and/or proximity sensors, one or more user input devices such as, for example a joystick, button, trigger, ball-tracking device, and the like, an a communications device to facilitate wired and/or wireless communication with the VR-HMD unit 32 and/or the computing device 36. The hand-held control devices could be substituted by hand tracking sensors based on ToF and/or regular cameras that doesn't require any hardware to be held.

The VR-HMD unit 32 includes a plurality of components 42 contained with a housing 44 containing. The components 42 include, but are not limited to, a VR display unit 46 and a sensor group 48. The sensor group 48 may include one or more position/motion sensors 50, an eye tracking system 52, a varifocal optics system 54, and an accommodation measurement system 56. The VR display unit 46 includes a VR display screen 58 and an integrated circuit 60 coupled to the VR display screen 58 for rendering a virtual reality scene on the VR display screen 58. The VR display screen 58 may be configured to display visual stimuli in dichoptic mode (e.g., separate scene generated per eye as shown in FIGS. 8-11). VR dichoptic content may be controlled by a pre-installed rendering software that will control virtual distance plane of generated scene according to obtained accommodation measurement data or visual activity scenario using varifocal optics. This kind of rendering software driver has to also implement managing with variable aberration and distortion correction that depend on currently set optical conditions. The integrated circuit 60 may include a SoC chip built into the VR-HMD unit 32 for rendering a VR scene using the VR display screen 58. The external controller 40 is programmed to analyze data collected by sensor group 48 and synchronizing data with the SoC HMD system 60.

For example, the VR display screen 58 may display on set depth plan through varifocal optics amblyopic eye stimulation (shown in FIG. 9) with increased contrast between the starfish and the diamond make assessing attention target positions easier, dominating eye occlusion (shown in FIG. 10) with increased brightness for the amblyopic eye means the intensity of light getting to that eye is higher diamonds are only displayed for the amblyopic eye, and/or amblyopic eye stimulation (shown in FIG. 11) with the image displayed for the dominating eye has reduced contrast to improve the intensity of signal getting to the amblyopic eye with diamonds are only displayed for the amblyopic eye. Changing the focal length of varifocal optics will affect with changing virtual distance (5 cm-5 m) which will occur with different binocular vision behaviors and visual parameters thresholds describing inter-ocular suppression. Different intensities of visual signals could be needed to conduct anti-suppression training in the full range of observing distance (near, intermediate, far).

The VR-HMD unit 32 also includes a communications device for use in communicating between the VR display unit 46, the eye tracking system 52, the accommodation measurement system 56, the varifocal optics system 54, the hand-held control device 34, and/or the computing device 36. The communications device may include a Wi-Fi antenna, a cellular network antenna, a Bluetooth™ communications device, a wired communications port, and/or any suitable wired and/or wireless communications device to facility communications with the hand-held control device 34 and/or the computing device 36. For example, the VR-HMD unit 32 may include a communication port 62 between the integrated circuit SoC goggle system 60 and the controller 40. In addition, the integrated circuit 60 may be programmed to receive training programs 26 from the controller 40 and to transmit information to the controller 40 for use in displaying information obtained from the eye tracking system 52 and an accommodation measurement system 56 to the controller 40 and/or display images of the training games being displayed on the VR display screen 58. In addition, the VR-HMD unit 32 may include a communication port 64 between the sensor group 48 and external controller 40 for use in transmitting information from the sensor group 48 to the external controller 40 and to facilitate operation and control of the sensor group 48 by the external controller 40. VR-HMD unit 32 may support 5G wireless network which could enable to using external computing box support that will execute computer power demanding tasks outside the HMD.

The position/motion sensors 50 may include, but are not limited to, accelerometer sensors, gyro sensors, and/or proximity sensors configured to sense movement and direction of the VR-HMD unit 32, and one or more integrated speakers with 3-D surround sound capability.

The eye tracking system 52 includes a near-infrared (NIR) camera assembly 66 and a micro-electro-mechanical systems (MEMS) assembly 68. The MEMS assembly 68 includes mirrors designed in one optical track with laser/light emitting module, light detector and beam-splitter (if needed). The eye tracking system 52 may also include a CMOS 2D profile sensor assembly 81 having a CMOS based 2D profile provided for pupil position estimation. Module could also include an actuator of base (zero) position of the MEMS mirror. Actuation can be done be an external module or it could be applied to MEMS module as an external addon.

The NIR camera assembly 66 is configured to perform eye tracking (viewer) based on NIR cameras for safety and eye doctor observation. The NIR camera assembly 66 includes a wide angle NIR LED 70 for eye illumination, an NIR camera 72 for recording the image illuminating the surface of the eye, a Hot mirror 74 configured to direct the light reflected from the eye surface to an NIR 72 camera.

The MEMS sensor assembly 68 provides eye tracking for precise eye movement analysis and includes a laser diode 78, a beam splitter 80, an oscillating micro-mirror 82 that directs the laser beam onto the eye surface within the operating range of the module, and a light detector 84.

MEMS based eye tracking: The context of eye tracking includes the therapy and diagnosis of vision in the VR environment using mobile HMD. These specific conditions mean that the module should fulfil the following functions: 1) High precision of 1 arcmin; 2) gaze determination calculation model 3) High frequency of measurement above 1000 Hz 4) Low computing power demand. The MEMS Module is designed to allow observation of special eye movement behaviors (e.g., fusionional vergence break and recovery point, fixation occurrence with/without fusion stimuli, ocular alignment change, fixation stability, smooth pursuits, saccades, micro saccades, fixation stability, ocular micro tremor).

Figure 4:
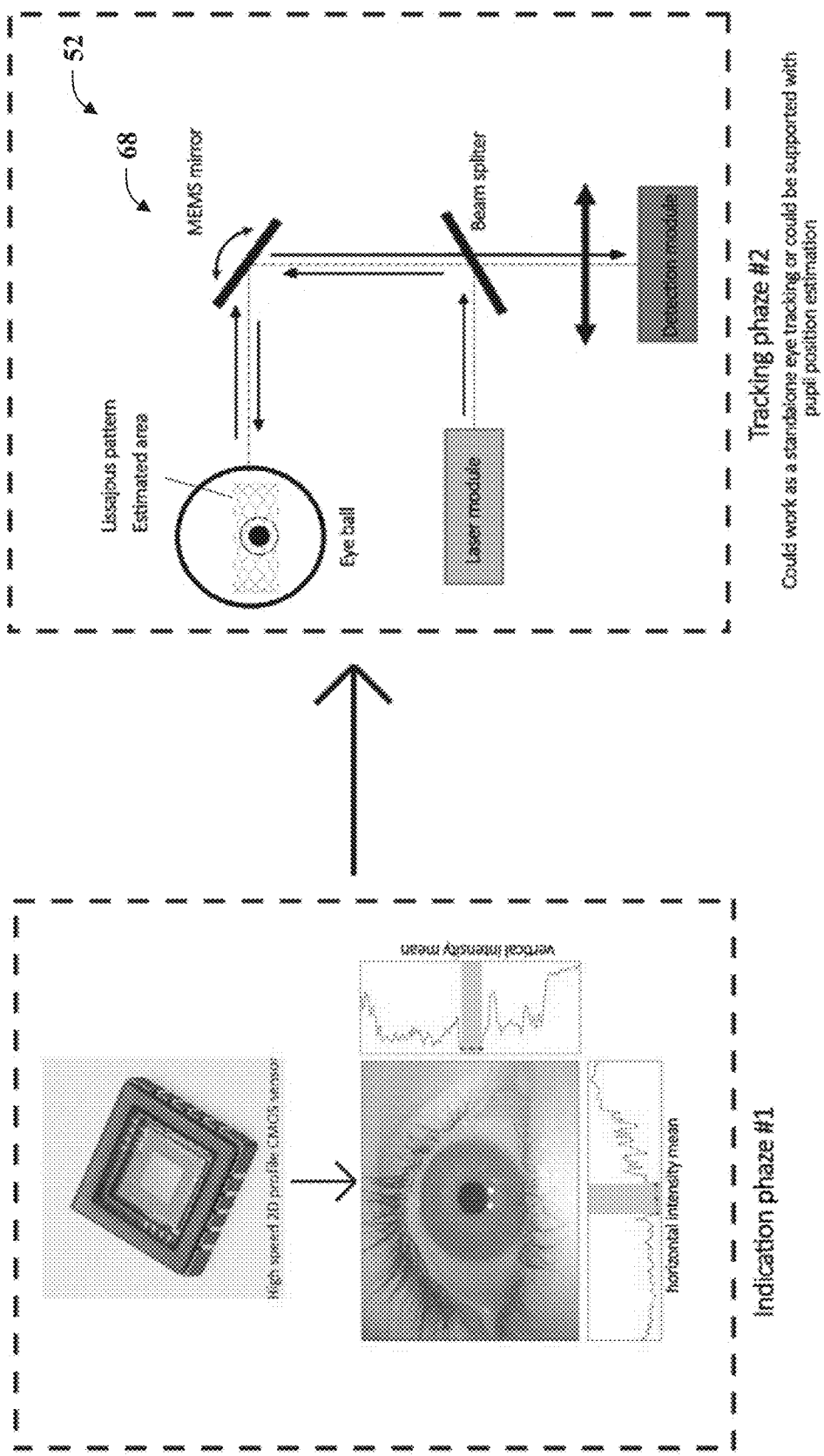
FIGS. 4-6 are schematic diagrams of an eye tracking system of the head-mounted display unit.
Figure 5:
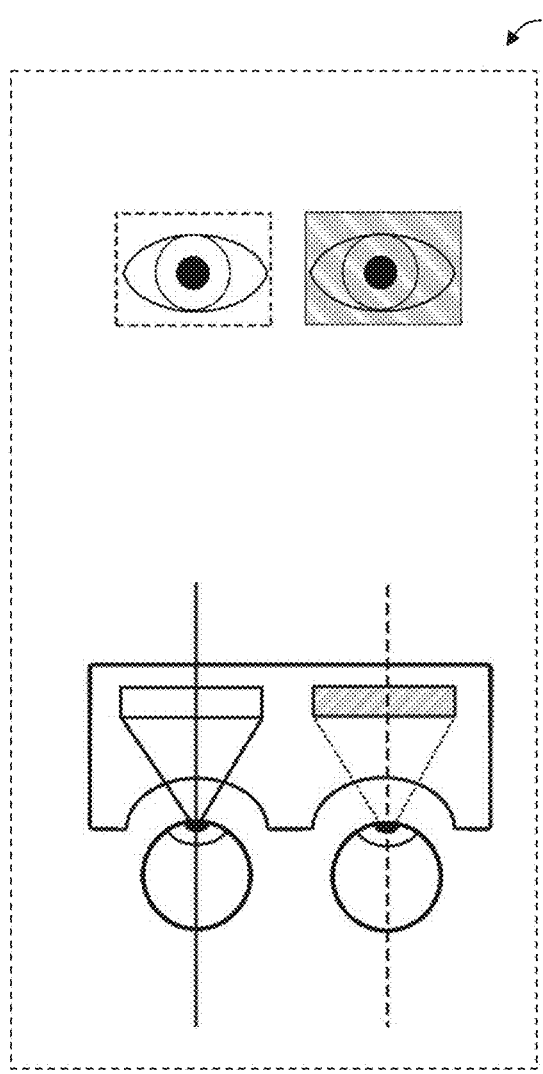

In some embodiments, the VR-HMD unit 32 includes an HMD construction with a built-in MEMS module according to the following design illustrated in FIG. 4 tracking phase 2 (main tracking). A laser diode emits a beam which, through a beam splitter, reaches a moving mirror and, after reflection, is reflected onto an object (eye). The mirror (electronically controlled) changes its angular position within the available range by changing the applied control voltage. The movement of the mirror results in a change of the laser beam's point of contact with the eye. The beam after lighting the object is reflected (dispersed). This reflected radiation emitted back passes through the moving mirror and beam splitter again and then falls on the detector. Changing the angular position of the mirror causes the laser beam to pass through the object alternately falling on the area of sclera, iris, pupil. Individual areas have different reflective characteristics, which results in a difference in the amount of radiation returning to the detector. A measurable effect is change of the amplitude of the signal when the beam is dispersed in the pupil's area in relation to the signal coming from the sclera area. By analyzing the variation in time of the signal obtained in comparison with the information about the position of the mirror, the position of the center of the object (i.e., the eye pupil) can be estimated.

In order to optimize the computational model, a specific MEMS module operating in control mode may be implemented, where the slow axis is controlled linearly, and the second, fast axis operates in resonant mode. This type of control is unique in the construction of the MEMS eye tracking module designed for eye tracking therapy and diagnosis, allowing for simplified estimation of mirror position and saving computing power, which is very limited in a mobile environment. In bi-resonant mode, the mirror position is more difficult to determine, and data is collected less homogeneously and more difficult to synchronize over time. However, this mode also provides advantages if it is designed to provide the system with a mirror position area feedback changing in time.

One of considered designs assumes that MEMS module may generate Lissajous pattern projected in area of pupil position estimated by CMOS 2D profile sensor (optional initial estimation—illustrated in FIG. 4 indication phase #1). Such a solution will affect with best data quality in terms of accuracy and resolution. Instead of projecting Lissajous pattern in field of view covering all eye surface, the system may limit beam sweeping area-based pupil position estimation done on second sensor that will provide high time-frequency. An example of such a module is CMOS based high-speed frame rate sensor capable of acquiring two-dimensional projection data such as S9132 provided by Hamamatsu™. A projection profile in the X and Y directions has very small amounts of data compared to normal area sensors and therefore allows high-speed position detection and moving object detection. The module works in the frame rate of 1600 frames/s (10-bit). The module collects data with low spatial frequency (256×256), which is not enough to perform high-quality eye tracking system. It is a perfect fit for pupil position estimation to be used as an approximate area to be tracked more accurately by MEMS module. Based on that, the system can dynamically control and limit MEMS mirror working angles according to the estimated area which will significantly increase accuracy and frequency of data obtained. Narrowing of MEMS operating field may be implemented in both MEMS specifications (one axis controlled linearly, second axis operating resonantly OR two axis's operating in resonant mode). Steering with base (zero entry) position of the MEMS mirror can be done by MEMS mirror itself or it could be controlled by an additional actuator combined with the MEMS mirror. Especially if one axis of MEMS mirror is controlled in linear mode, coordinate of this axis could directly depend on estimated coordinate of pupil position done by CMOS 2d profile. In such a case, second axis of MEMS mirror will work in resonant mode with limited constant sweeping angle with a variable base-point. Combination of these two modules works as a best solution providing science-grade data quality.

Referring to FIGS. 12-16, in some embodiments, the system 10 may track the movements of the object (eyeball) with minimal computational requirements based on a bi-resonant approach. The effect of the proposed method is to be the ability to determine the coordinates $(x_0, y_0)$ of the pupil center. The solution proposes to use a MEMS 2D micro-mirror to scan an object in the XY plane and analyze the signal intensity on the scanning path. Mirror modes of operation: resonant in X and Y axis. In this mode of operation, the XY plane is scanned according to Lissajous figures. The scanning frequencies in the X axis (F_X=a) and in the Y axis (F_Y=b) should be different. Ratio b/a>10; b/a $\notin$ N. Initial phases δ will be random. The X-axis (A) and Y-axis (B) swing amplitudes depend on the parameters of the MEMS mirror below visualization for case b/a=10

Based on the system calibration, the coordinates of the scanning point (x,y) in the XY plane as a function of the time moment (t) are known.

$$x(t)=A \sin(a*t+\delta); y(t)=B \sin(b*t);$$

When scanning an object (eye), the intensity of the detected s(t) signal will be variable. General rule illustrated in FIG. 14: outside the pupil of the eye, the signal will be greater than inside the pupil.

Area of scanning may be limited to the estimated pupil position provided by CMOS 2D profile sensor (FIG. 4 Indication phase #1). Mirror zero-baseline could be set based on this evaluation. Angle of axis will be narrowed, so density of resonant scan will be higher. By implementing such a solution, the system 10 increases the number of tracked points determining pupil edge which makes accuracy of tracking significantly better.

Figure 14:
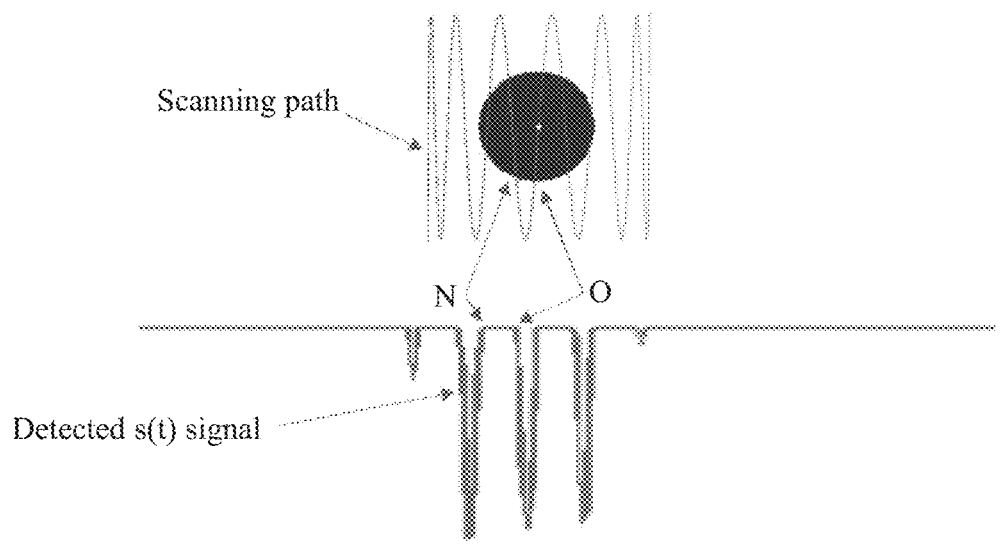
Figure 15:
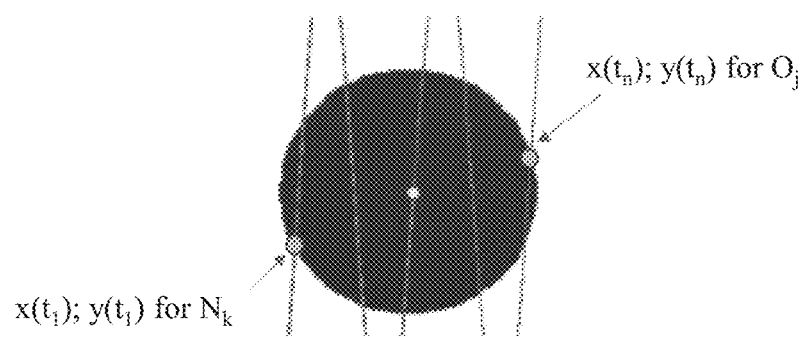
Figure 16:
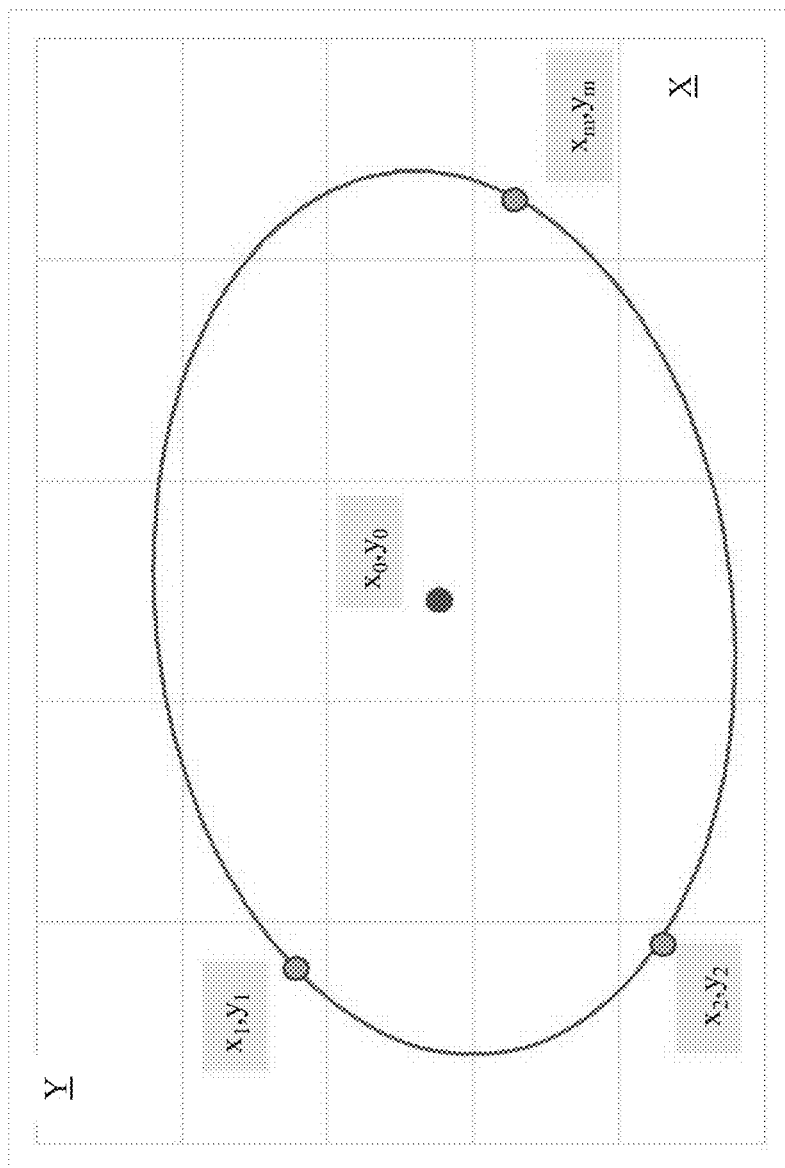

FIGS. 14-16 illustrate an example visualization for b/a=13. Based on the s(t) signal analysis, descending (input pupil area ->O) and ascending (output pupil area ->N) slopes are detected.

The sets of detected characteristic points ($N_k$ and $O_j$) for the following time moments t, allow to determine characteristic points $(x_i; y_i)$ in the XY plane which is illustrated on FIGS. 15-16.

Referring to FIG. 16, depending on the relative spatial relations between the object (eye) and the MEMS mirror, the object (pupil) in the XY plane can take various shapes, e.g., circle, ellipse. The ellipse can be described, among others, by the parametric equation:

parameter $0 \leq p < 2\pi$ $x(p)=A1 \cdot \cos(p)+x_0;$ $y(p)=A2 \cdot \sin(p+\alpha)+x_0;$ The general analytical function describing the edge of the object (pupil) will be the form:

$$Ax^2-Bxy+Cy^2-Dx-Ey+F=0$$

Referring to FIG. 15, having the set M (where: $M=N_k+O_j$) of such points $[(x_1,y_1); \ldots (xm,ym)]$ on the edge of the object and assuming the function y=f(x) describing the object (pupil), it is possible to determine the parameters of this function including the position of the center of the object (pupil).

The method of least squares may be used to determine the above-mentioned center $(x_0, y_0)$ (illustrated in FIGS. 15-16) and other f(x) function parameters:

$$S = \sum_{i=1}^{M} (y_i - f(x_i))^2$$

The minimum of this function (a derivative of the S function in relation to parameters $x_0$ and $y_0$ compared to zero) allows to determine the function describing the desired center of the object (pupil) for the series M measuring points.

$$\frac{\partial S}{\partial x_0} = 0; \quad \frac{\partial S}{\partial y_0} = 0$$

This in turn is the basis for further analysis to determine the orientation of the object (pupil in 3D) and then to determine the fixation point of the eyes.

In some embodiments, the eye tracking method may include state of the art MEMS mirrors such as the S13989-01H MEMS mirror (available from Hamamatsu™). The S13989-01H MEMS mirror was made smaller by arranging the magnet beneath the mirror, with high reliability achieved by employing a hermetic seal package. Electrical current flowing in the coil surrounding the mirror produces a Lorentz force based on Fleming's rule that drives the mirror. Hamamatsu™, Sercalo™, and Maradin™ MEMS mirrors offer a wide optical deflection angle and high mirror reflectivity. It is important also to receive a feedback from the module estimating mirror position area at time.

The accommodation measurement system 56 provides a set of elements combined for ocular accommodation response analysis. The accommodation measurement system 56 includes a light emitter 86 designed to obtain retinal reflex, a sensor 88 recording retinal reflex (e.g., a Shack-Hartmann sensor), a hot mirror 90, and a beam splitter 87. The accommodation measurement system 56 may be also based on light beam sweeping module and for quadrant diodes designed to implement like an automated sciascopy procedure (emitting a sweeping beam over the retina and controlling direction and intensity of obtained reflex).

For example, a key element of the VR-HMD unit 32 is the feedback analysis of the eye's accommodation response. In a situation where the varifocal optics module generates a stimulus for accommodation, the system must know if the accommodation system responds correctly by focusing on the specified optical plan. This information is crucial for the accommodation and convergence training.

Nowadays, during accommodation training, generation of a variable accommodative stimulus is done by mechanically changing lenses or by changing the distance of observation. It is not possible to objectively and dynamically assess the patient's accommodation response. Proposed solution will allow to generate variable stimulus with simultaneous assessment of the response, which will increase the effectiveness of accommodation training.

When the optical plan is known, on which the eye sets its focal length, the system can dynamically modify the position of the virtual plan with varifocal optics. For example, the system can change alternately the position of the virtual object in close distance and near distance. The patient's task is to focus on a given object. Once focused and obtained sharp vision, the accommodation response is consistent with the expected optical plan. This way the system can automate the training.

Today, the information about the accommodative response during vision therapy session (picture being sharpened by the patient) is given subjectively, which is burdened with a huge mistake due to a subjectivity of a statement made by a minor patient ('clear or blurry picture'). The accommodation measurement module 56 would allow for objective information about the optical condition of the patient's eye and would adjust the training scenario in real time. Similarly, it would be important to intentionally shift the accommodation stimulus by a constant value in dioptres and to force the patient's accommodation during training in a continuous pattern. In addition, information about the state of accommodation will give us objective information whether the optical plan controlled by the VR goggle variable-focal system in VR goggles properly stimulates the visual system—for example, if work at a distance of 1m is desired, it must be known whether the patient really focuses his eyes on the preset virtual distance. Another element is the control of accommodation in determining refractive errors (myopia, hypermetropia, astigmatism). A big problem for specialists is the uncontrolled change of accommodation during a subjective examination of refractive error based on the optotypes table (especially in children), which affects the outcome of the examination. In order to paralyzes the accommodation, the atropine is applied. The proposed solution coupled with the variable-focal system would allow for objective control of the visual system during subjective examination of visual acuity based on optotype-based tests.

The accommodation measurement system 56 may include a set of Shack-Hartmann optical system and algorithms that analyze the shape of the wave front reflected of the eye lens. The focusing optics will be based on a lens matrix or a meta-lens system. A similar solution is used in the measurement of all parameters of the optical system of the eye such as aberrations, which is necessary during the Lasik procedure. The system 10 may involve only the measurement of eye accommodations in HMD so calculation model will be simplified to that use case.

The accommodation measurement system 56 may also include automated sciascopy. This method is often used by eye doctors using analog tools. Automation of this method involves building a swinging beam emitter and detectors analyzing the filling and direction of retinal reflexes according to move of emitting beam. This method is a simple and computer power economic concept, easier to implement that Shack-Hartmann concept, however it could provide with less data characterizing ocular lens state. The accommodation measurement system 56 provides key features of the mobile VR HMD's accommodation measurement module to objectivize measurements for the diagnosis and treatment of binocular visual impairments and determination of refractive errors. Properly configured module will be able to calculate objective eye optical power (cylindrical and spherical) of refractive errors during relaxed state of accommodation which is market available devices could distract the output.

The varifocal optics system 54 includes varifocal optics 92 placed between the patient's eye and the screen 58 designed to provide controlled accommodation stimuli and depth perception plan.

Metalens based varifocal optics: a basic assumption of the system is to prepare a device that projects a virtual scene in a controlled depth perception plan. The technology today focuses on variable-focal optics in VR goggles in order to solve the vergence-accommodation conflict in HMD devices.

The varifocal optics system 54 is designed to enable the control of the accommodation stimulus (optical depth plan) independently to the right and left eye within a range from 5 cm to 5 m. This solution indirectly solves mentioned VAC problem, but it is not the main goal of the invention.

A main challenge of the system is to address Near Point of Accommodation and Near point of Convergence which means simulation of 5-6 cm virtual distance keeping ability of relaxing accommodation state through the optical system (3-5 m virtual distance). Important part is also a custom rendering engine for aberration, distortion, focal plane management. Key feature of the system is to provide two types of distance change: continuous and jumps independently for the left and the right eye.

The goal is much broader than solving Vergence Accommodation Conflict. The system 10 achieves a higher objective: to control accommodation stimuli separated from convergence stimuli provided independently to the left and right eye. Vision therapy scenarios often require different stimulus to accommodation and convergence depending on a prescribed scenario. Moreover, the system 10 doesn't require close to zero low latency varifocal optical system. To reduce distortions and aberrations issues, the system 10 implements proper gaming scenarios that will force patient to operate in relatively low Field of View.

The system is considered using 3 approaches of changing focal length of optical system: liquid-membrane lens, mechanical varifocal lens set, metalens varifocal lens/lens set. The most promising is a metalens approach as it could provide spherical power and cylindrical axis change. It could be crucial for refractive errors management. The most affordable solution is based on set of two lenses where position of one is actuated by linear movement mechanism.

The varifocal optics system 54 includes a variable-focal optical system that effectively performs exercises and diagnostics in the near, far and intermediate distances. Human visual system behaves differently depending on the optical plan it works in (different binocular vision behaviors depending on working distance of an exercise). In an office environment, it means that the therapist must have a large enough office and precise equipment to work in different conditions for eye accommodation (from 0.3 m to 5 m). The use of a variable focal length in VR goggles solves this problem by providing a number of depth perception conditions for near and far in visual exercises. Moreover, the use of this module opens us up to training and diagnosis of accommodation and convergence disorders, which is not possible with the use of traditional VR goggles.

The varifocal optics system 54 may include: 1) A set of meta-lenses where one is movable (movement can be triggered by a change in the volume of an electrically sensitive substance placed between the edges of the lenses—due to the light weight of the lenses, there will be no need for mechanical control of the system, which represents a major breakthrough and added value); 2) Single lens (the shape of which is electrically controlled); and 3) Meta-lens array with electrically controlled variable optical parameter(s) (e.g., polarization state, focal length) combined with a VR display 60 to generate light field as a visual stimuli.

The varifocal optics system 54 may be also based on one meta-lens provided per each eye when shape of each lens is controlled by electrically sensitive substance placed around the lens. The varifocal optics system 54 may be also based on liquid-membrane solutions designed by $3^{rd}$ party vendors like Optotune™. The varifocal optics system 54 may be also based on a set of 2-3 regular lenses wherein relative positions and angles of the lenses are controlled by micro stepper motors within designed movement mechanism. However, the most promising solutions are based on meta-lenses due to its optical flexibility and non-mechanical elements.

The varifocal optics system 54 provides key features including: 1) Use case context—application of meta-lenses in the varifocal optics embedded in mobile HMD VR for the diagnostics and therapy of binocular vision disorders, especially in the case of accommodation-vergence disfunctions; 2) system control without stepper motors, mechanical systems; 3) optical plan control for left and right eye independently for vision exercises and visual tasks provided by the VR system; and 4) calculation model for chromatic aberration and distortion correction at VR rendering level.

In some embodiments, the vision assessment and therapy device 12 provides eye alignment analysis system for diagnostics of binocular vision. The device 12 includes an eye tracking module, standalone VR goggles, an external computing unit, control software and a touch screen is designed to analyze the alignment of the eyes in the diagnosis of binocular vision: quantitative evaluation of the deviation of the eyes (phoria or tropia) and evaluation of vergence (fusion vergence ranges and near point of convergence). The basic principle of the device 12 is to analyze the position of the eyes through the eye tracking module in order to assess the occurrence of the specific visual system reaction: i.e., fixation occurrence and the breaking and recovery of the fusion in relation to the generated, isolated binocular stimulus in the VR environment. The device 12 automatically evaluates the occurrence of these reactions of the visual system under the conditions of fusion stimulus projection as monocular stimulus and compares them with the spatial geometry of the generated stimuli in the VR environment, which is the base for the measurements.

The unilateral and alternating cover test is performed up to a distance (4-6 meters) and up to the nearest distance (40 cm)—here the varifocal system it is necessary to correctly assess the alignment of the eyes with the impact of accommodation response. Crucial part of it, is that system doesn't really calculate gaze points. The system 10 is focused on determining occurrence of specific eye response against provided VR stimuli, and provides outcomes based on simplified analysis model. Other systems implementing eye tracking methods are focused on determination the outcomes based on gaze point data.

The vision assessment and therapy device 12 may include MEMS eye tracking/NIR cameras. The device can emphasize that the neural network/algorithm will evaluate the behavior of eye movements in an abstract way independent of the gaze point. That is, the device will analyze the movement of the pupil on a sequence of frames of images/data and provide information about its occurrence or non-occurrence, comparing it with the conditions of the spatial geometry of the VR scene. Known systems evaluate the occurrence of characteristic behaviors on the basis of ready-made data of gaze points and then draws conclusions. However, there is no need to determine the gaze points to realize the task, it is enough to analyze only the occurrence of pupil movement (binary output—yes, no) on the sequence of frames—this is a simpler solution, more economical for computing power and allows for greater precision of the result.

Based on presented eye tracking methods system is able to process data describing ocular movements in a reference to visual stimuli provided binocularly including set depth plan and controlled accommodation response. Data obtained may contain characteristics of each type of eye movement and behavior: saccades, micro-saccades, intersaccadic drift, ocular micro tremor, smooth pursuit, optokinetic nystagmus, vestibular ocular reflex, fixation stability. The science's position in that matter indicates that eye acts as a window to human brain activity. Ocular movements measured in such a precise way supported with AI driven data analysis bundled with advanced visual stimuli generation lead to ability of implementation early detection, screening, progress monitoring, diagnosis of neuro-related diseases such as: Parkinson's disease, Alzheimer's disease, Schizophrenia, Multiple Sclerosis, Concussion, mTBI, CTE, Dementia with Lewy-Bodies, Frontotemporal Dementia, Corticobasal Degeneration, Huntington's Disease, Multiple System Atrophy, Progressive Supranuclear Palsy, Dyslexia, ADHD, Bipoloar disorder, Autism spectrum disorder. On the top of that, ocular movement analytics done be presented system may evaluate pharmacological effects on brain systems. This approach may be a breakthrough in pharmaceuticals prescription and dose control. All of the mentioned activities in this section can be described as "ocular biomarking".

Below please see selected quotes from scientific studies confirming validity of the presented correlation:

Eye Movements as Biomarkers to Evaluate Pharmacological Effects on Brain Systems: "There is increasing evidence that eye movements are sensitive biomarkers of drug effects on discrete sensorimotor and cognitive processes both for examining side effects in early phase studies with healthy individuals as well as in studies of potential cognitive enhancers or therapeutics in clinical settings. In many examples reviewed above, eye movement paradigms have shown greater sensitivity to pharmacological effects than neuropsychological measures or subjective ratings, with strong dose-response effects that potentially could be used to individualize drug dosing for patients. In addition, use of eye movements in studies involving pharmacogenetics and genetics remains highly promising and may lead to improved understanding of heterogeneity in drug response as well as in drug selection. With the need for biomarkers to support the development of new drugs and assess their efficacy, eye movement studies offer particular methodological benefits including the translational linkages to discrete neurotransmitter and neural systems, the rational manner to evaluate pharmacological effects for proof of concept/target engagement, and for understanding individual differences in drug response." "the present results support the potential of microsaccade count for further investigation as a possible biomarker of drug response, possibly at the collicular level. If microsaccade rate reflects collicular activity levels the measure may provide a means of initially screening potential pharmacotherapies for disorders with a collicular component."

Typical and Atypical Development of Eye Movements: "Starting with an introduction and discussion of five basic paradigms in studying eye movements in atypically developing populations, Sect. 15.4 focused on four neurodevelopmental disorders—autism, attention-deficit/hyperactivity disorder, reading disorder and early-onset schizophrenia—and explained what eye movement research has contributed to the understanding of these disorders. We saw that standard paradigms like pro-, anti-, or memory-guided saccades can provide valuable information about deficits that may or may not be specific to individual disorders, whilst the free viewing paradigm can reveal peculiarities in visual attention for various kinds of social or non-social stimuli. Altogether, the studies presented in Sect. 15.4 made clear that the recording of eye movements is a highly versatile approach in the study 688 C. Klein et al. of neurodevelopmental disorders, capable of yielding unique results that cannot be yielded by other technologies."

Psychiatry—Schizophrenia: "Differences in performance were observed in patients with schizophrenia compared to controls in a variety of saccadic eye movement tasks using different parameters measured in each one of these tasks. In terms of robustness of these effects, the increase in antisaccade error rate is the best replicated finding in this large literature with the largest effect size in dissociating patients from controls at the group level." "We established an integrated eye movement score with high classification accuracy between patients with schizophrenia and healthy controls, although there was a significant effect of medication. This study provides further evidence of the utility of eye movement abnormalities in schizophrenia pathology and treatment." "The study confirms the existence of different relations between the symptom dimensions of schizophrenia and saccades tasks performances. Saccadic abnormalities were revealed in the clinical (schizophrenia) and pre-clinical (clinical high risk) populations that provide further evidence for assessing saccadic abnormalities as a possible neurobiological marker for schizophrenia."

Psychiatry—Autism spectrum disorder: "Enhanced visual preference for geometric repetition may be an early developmental biomarker of an ASD subtype with more severe symptoms."

Psychiatry—Bipolar disorder: "Bipolar disorder is a disturbance in mood marked by cycling periods of mania and/or depression. Bipolar patients have been shown to have an inhibition problem, as well as deficits in working memory and voluntary eye movement paradigms. Bipolar patients, as well as lithium-withdrawn manic patients, have been shown to perform more poorly than normal controls on an SPEM task."

Psychiatry—ADHD: "ADHD patients have been shown to be impaired on a countermanding task (similar to a delayed saccade task, but a stop signal may be presented on some trials to indicate the response should be withheld), which suggests that their impairment mainly consists of increased impulsivity. In addition, voluntary eye movement deficits have shown subtype differences within the ADHD population. Specifically, patients classified as ADHD-Inattentive have better motor planning and are less impulsive than ADHD patients with both inattentive and impulsive characteristics. Interestingly, methylphenidate improves the voluntary eye movement performance of both ADHD subtypes"

Psychiatry—Fatigue development: "The association of changing characteristics of eye movements with fatigue can potentially provide a quantitative approach to the development of an informed decision on a work-pause regime63 hampering fatigue."

Psychiatry—Dyslexia/reading skills: "Finally, it is important to stress that not all children who experience persistent difficulties in learning to read fit the same neuropsychological profile. It is well-established, for example, that there is considerable symptom overlap and a high rate of comorbidity between dyslexia, attention-deficit hyperactivity disorder (ADHD) and language impairment [54-55]. Moreover, it is also common to distinguish between different subtypes of dyslexia (e.g., surface vs phonological dyslexia). Therefore, diagnostic follow-up of a positive screening result is always necessary to gather a more comprehensive understanding of an individual's cognitive profile, so that intervention strategies can be tuned to individual needs. Nevertheless, early identification of individuals in need of support is the first important step in this process. For this purpose, using eye tracking during reading may prove very useful."

Neurology—Parkinson's Disease: "PD is also associated with eye movement disturbances, which commonly vary according to the task and to the progression of the disease. Saccadic metrics and latencies show significant differences in comparison to healthy individuals.

Neurology—Progressive Supranuclear Palsy: "Oculomotor disturbances are generally more pronounced in PSP than in PD. In PSP, saccades show abnormalities in velocity, latency, and amplitude. Saccadic velocity is reduced, particularly for saccades performed in the vertical dimension (and, in some cases, particularly for downward saccades). This sign is already observable early in the disease course."

Neurology—Multiple System Atrophy: "the oculomotor disturbances observed in MSA may have common features with the presentation of PD and PSP, such as excessive square wave jerks, mild vertical supranuclear gaze palsy, mild or moderate saccadic hypometria, mild (or no) slowing of vertical saccades, impaired smooth pursuit, and reduced vestibulo-ocular reflex cancellation. However, gaze-evoked nystagmus and positionally-induced downbeat nystagmus may be distinctive features of MSA."

Neurology—Huntington's Disease: "The most important clinical feature of HD is chorea (i.e., "dance-like", brief, semidirected, and irregular movements), which is initially transient, then progresses to continuous, athetoid, and dystonic movements. In this stage of the disease, the patient is unable to feed, dress, or to use the toilet. Personality changes may also be observed, consisting of irritability, apathy, and depression. A subcortical type of dementia, leading over time to a global dementia, is also associated with HD."

Neurology—Corticobasal Degeneration: "Corticobasal degeneration (CBD) is a rare, late-onset neurodegenerative disorder of unknown aetiology, which is characterized by a movement disorder, an asymmetric akinetic-rigid syndrome with marked dyspraxia, involuntary movements, and alien limb/hand behavior, in combination with cognitive disorders resulting in cortical dementia."

Neurology—Alzheimer's Disease (AD): "The oculomotor deficits in AD affect both saccadic and fixational eye movements. Saccades are usually hypometric, their velocity is—at least mildly—reduced, particularly for vertical saccades, and their latency in increased, particularly for voluntary saccades. The vestibulo-ocular reflex is usually preserved. Steady fixation is disrupted by small-amplitude square wave jerks and large-amplitude saccadic intrusions."

Neurology—Frontotemporal Dementia: "Oculomotor deficits in FD include reduced saccade velocities (particularly on the horizontal dimension), increased saccadic latencies, and poor performance in complex saccadic tasks, such as antisaccades: increased number of errors (but usually corrected), and a higher incidence of early saccades, in comparison to healthy individuals. Reduced saccadic velocity and deficient saccadic suppression seem to be largely dependent on the sub-syndrome type and on the anatomical distribution of the affected cerebral areas."

Neurology—Dementia with Lewy-Bodies: "The typical fluctuations in cognitive performance in DLB are also observed in oculomotor deficits: saccadic velocity and saccadic metric accuracy (i.e., gains) are usually reduced, but both parameters show a much greater variability than in healthy individuals. Saccadic latency is usually prolonged, and express saccades have a lower incidence. In complex saccadic tasks (e.g., antisaccades, target prediction), DLB patients show higher error rates than healthy individuals, compatibly with their cognitive impairments. Generally, vertical gaze seems to be more affected than the horizontal one, and upward gaze more than the downward one."

Neurology—Multiple Sclerosis: "Most frequent oculomotor dysfunctions were impaired smooth pursuit (42.3%), saccadic dysmetria (41.7%), unilateral INO (14.7%), slowing of saccades (14.7%), skew deviation (13.5%), and gaze evoked nystagmus (13.5%)."

"Microsaccades provide objective measurements of MS disability level and disease worsening."

Neurology—Concussion: "If one defines concussion based on history, physical examination, radiographic and SCAT3 criteria, it is possible to generate an eye tracking based biomarker that enables detection of concussion with reasonably high sensitivity and specificity."

Neurology—mTBI/CTE: "Eye tracking shows promise as an objective, sensitive assessment of damage after mTBI." "Concussion, or mild traumatic brain injury (mTBI) usually results from a blow to the head that leads to temporary functional alterations in the brain frequently including executive function deficits. These most often occur in sports, motor vehicle accidents, or falls, but can also result from explosions (even without direct impact to the head). The term subconcussive describes blows to the head that produce neuronal changes similar to those in concussion, but without the acute symptoms such as nausea, headache, irritability, or obvious executive function impairment. Most concerning, however, is recent evidence that suggests that repetitive subconcussive head impacts themselves, even without history of concussion, may lead to executive function deficits (with tasks similar to these eye tracking paradigms), imaging and pathological deficits, as well as increased vulnerability to develop a neurodegenerative disease, such as chronic traumatic encephalopathy (CTE)."

Figure 6:
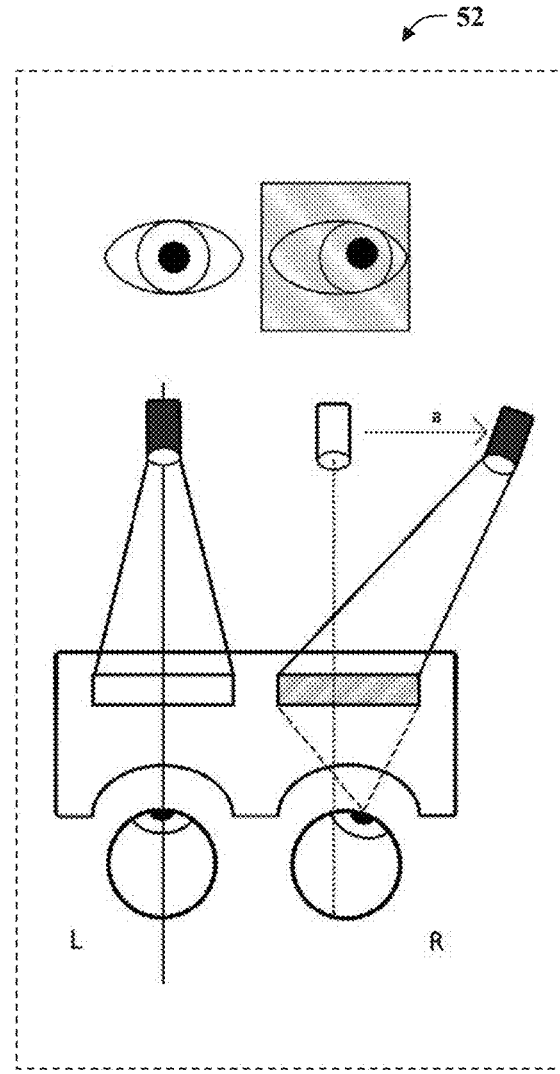
Figure 7:
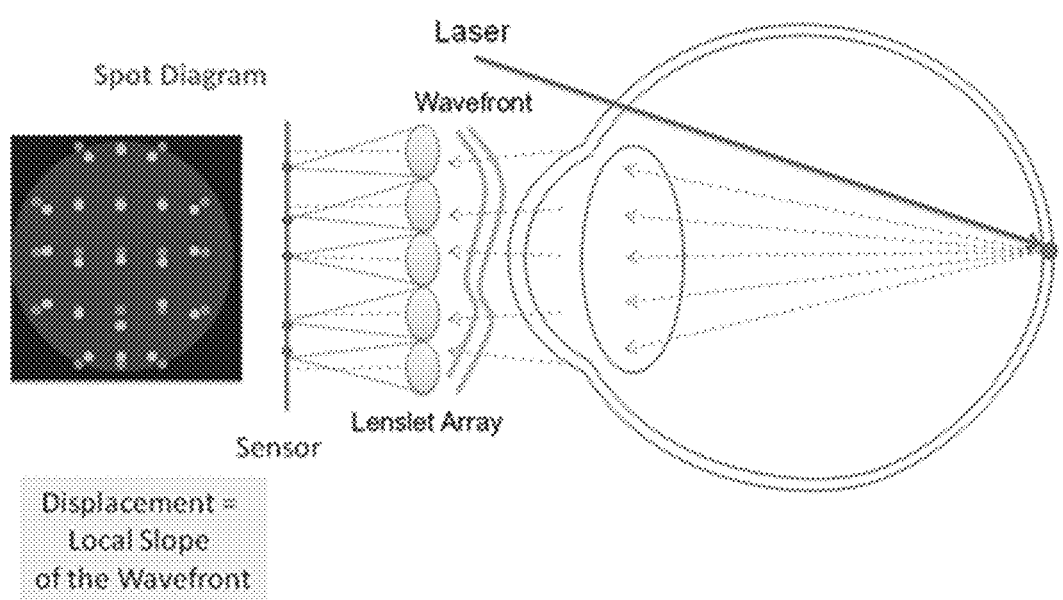
FIG. 7 is a schematic diagram of an accommodation measurement system of the head-mounted display unit.
Figure 8:
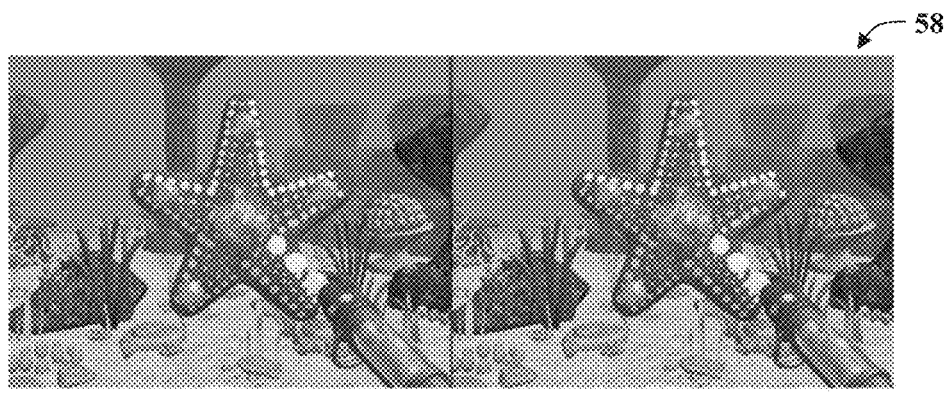
FIGS. 8-11 are illustrations of images that may be displayed by the head-mounted display unit.
Figure 9:
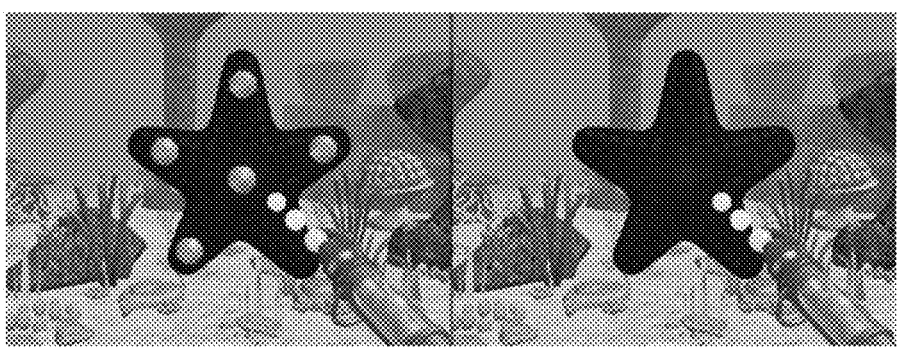
Figure 10:
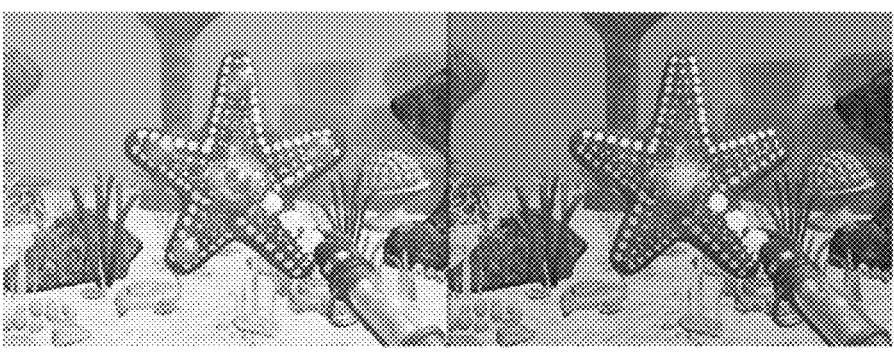
Figure 11:
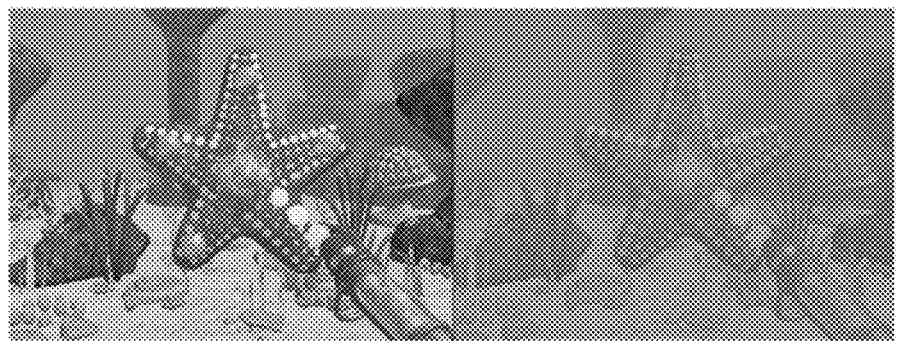
Figure 12:
FIGS. 12-16 are illustrations of the algorithms that may be executed by the system for use in operating the eye tracking system shown in FIG. 4 to track movement of a patient's eyes.
Figure 13:
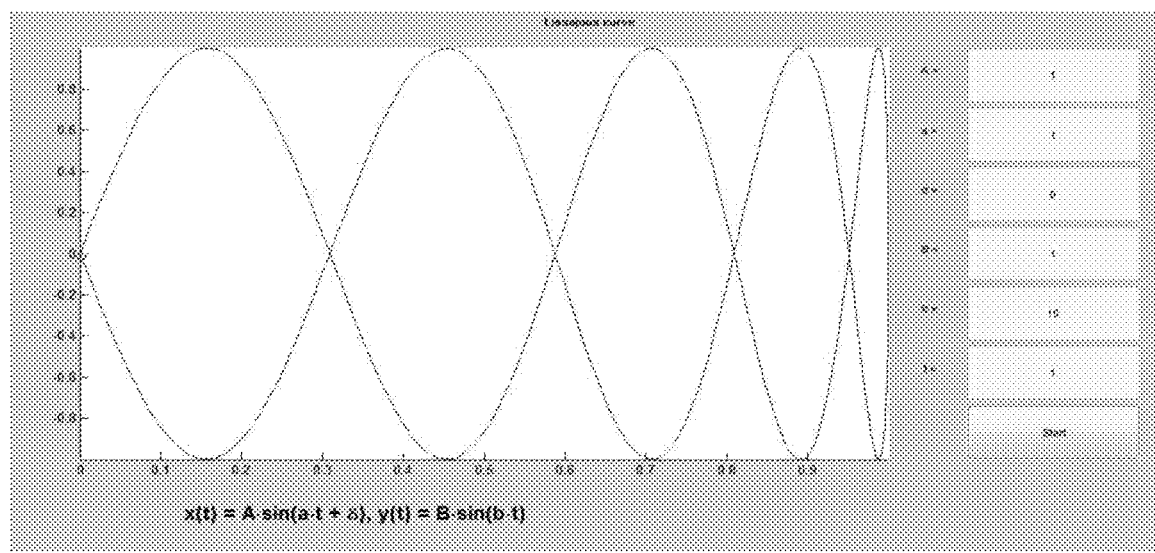

In some embodiments, the vision assessment and therapy device 12 may include: 1) the evaluation of the occurrence of the specific eye movement is carried out automatically by the control software without gaze point calculation; 2) the simulation of the covering/uncovering of the eye is based on the turning off/on of a screen providing stimuli to the left or right eye (shown in FIG. 5); 3) the prism strip used to quantify eye alignment is replaced by a virtual camera projecting independent scenes for the right and left eye, which changes its angle of deviation in such a way as to compensate for the movement of the eyes during the examination (shown in FIG. 6).

The vision assessment and therapy device 12 may also include: 1) Eccentric fixation stabilization system dedicated for patients with AMD designed to improve their visual skills based on MEMS eye tracking and mobile VR platform; 2) Visual field restoration system dedicated for post-stroke patients; and 3) Visual field assessment system.

The vision assessment and therapy device 12 may also be implemented in a mobile VR platform based on Qualcomm™ XR/Snapdragon solutions. The device would control the fixation of the object displayed in front of the patient using built-in eye tracking module and take a field of view test only when the patient is focused on the object.

The vision assessment and therapy device 12 may also include HMD with built in metalens varifocal system, MEMS eye tracking, Shack-Hartmann based accommodation measurement module for vision assessment and therapy. A combination of all modules creates a system for binocular vision therapy, and diagnosis and refractive errors diagnosis in one device. Unification of all concepts, vision therapy exercise and diagnostic tests mentioned above in a single device.

Modules/platforms/features: 1) Mobile VR device consisted of HMD and externally plugged computing box; 2) Varifocal metalens optical system; 3) Eye tracking based on MEMS module empowered by 2D profile sensor estimating pupil position; 4) Eye viewer based on NIR cameras; and 5) Accommodation measurement module based on Shack-Hartmann concept and/or automated sciascopy.

The vision assessment and therapy device 12 may include ophthalmic and optometry fields to be covered by a single device: 1) Binocular vision therapy and diagnosis: 3 grades: simultaneous perception, fusion, stereopsis; fusional vergence ranges 2) Eye movement therapy and diagnosis: Saccades/pursuits; 3) Accommodation disorders therapy and diagnosis; and 4) Refractive errors determination subjective and objective: myopia, hypermetropia, astigmatism.

In some embodiments, the vision assessment and therapy device 12 is configured for use in vision assessment and therapy and ocular movement biomarking of neuro-related diseases. The vision assessment and therapy device 12 may include the Virtual Reality-Head Mounted Display (VR- HMD) unit 32. The VR-HMD unit 32 may include a housing 44, a virtual reality (VR) display unit 46 positioned within the housing 44 and configured to display images to a user simulating a virtual reality environment, a varifocal optics system 54 positioned within the housing 44 and orientated between the VR display unit 46 and the user's eyes, an accommodation measurement system 56 positioned within the housing 44 and configured to measure an accommodation response of the user's eyes, and an eye tracking system 52 positioned within the housing 44 and configured to track movement of the user's eyes.

The varifocal optics system may include a pair of metalenses, each metalens being associated with a corresponding eye of the user. For example, the varifocal optics system may include a first set of metalenses associated with a first eye of the user and a second set of metalenses associated with a second eye of the user, each set of metalenses including at least one tunable metalens. The varifocal optics system may also include a pair of tunable liquid-membrane lenses, each tunable liquid-membrane lens being associated with a corresponding eye of the user.

The accommodation measurement system may include a projection assembly including a near-infrared (NIR) marker projecting module configured to produce an image marker on both a retina and a cornea of the eye. The accommodation measurement system may also include an acquisition assembly is configured to perform detection of the image marker produced by the proj ection assembly. In some embodiments, the accommodation measurement system may include a light emitter configured to emit light to obtain retinal reflex of the user's eye, a sensor configured to receive reflected light from the user's eye and record the retinal reflex of the user's eye, and a hot mirror configured to reflect the light emitted from the light emitter towards the user's eye and reflect the reflected light from the user's eye towards the sensor. The accommodation measurement system may also include a beam splitter orientated to reflect the light emitted from the light emitter towards the hot mirror and pass the reflected light from the hot mirror towards the sensor.

In some embodiments, the eye tracking system may include a micro-electro-mechanical systems (MEMS) sensor assembly for tracking a position of the user's eyes. The MEMS sensor assembly may include a laser diode for emitting a beam of light, a light detector configured to detect reflected radiation from the user's eye, and an oscillating micro-mirror configured to reflect the light emitted from the laser diode towards the user's eye and reflect radiation from the user's eye towards the light detector. The MEMS sensor assembly may also include a beam splitter orientated to reflect the beam of light from the laser diode towards the oscillating micro-mirror and pass the reflect radiation received from the oscillating micro-mirror towards the light detector. In some embodiments, the eye tracking system may include a CMOS 2D profile sensor for providing pupil position estimation.

The vision assessment and therapy device 12 may also include a processor programmed to perform a neurodegenerative disease screening exam by executing an algorithm including the steps of adjusting the varifocal optics system to an initial refractive correction, displaying visual stimuli on the VR display based on desired test scenario, collecting eye movement data using eye tracking system, and determining neurodegenerative disease by comparing collected eye movement data with baseline eye movement data associated with desired test scenario. The processor may also be programmed to execute the algorithm including the steps of adjusting the visual stimuli based on collected eye movement data, collecting subsequent eye movement data in response to adjusted visual stimuli, and determining indication of neurodegenerative disease by comparing collected eye movement data with baseline eye movement data associated with desired test scenario.

In some embodiments, the processor may also be programmed to perform a refractive errors assessment by executing an algorithm including the steps of operating the varifocal optics system to adjusting optical conditions to an initial refractive correction, displaying visual stimuli on the VR display based on desired refractive errors assessment test scenario, collecting eye movement data using eye tracking system, collecting ocular accommodation data using the accommodation measurement system, and determining ocular behavior based on collected eye movement data and ocular behavior data. The processor may also be programmed to execute the algorithm including the steps of adjusting optical conditions and/or visual stimuli, collecting subsequent eye movement data and ocular accommodation data in response to adjusted optical conditions and/or visual stimuli, and determining ocular behavior based on the subsequent eye movement data and ocular accommodation data.

Referring to FIGS. 18-41, in some embodiments, the system 10 may include a diagnostic device 102 that includes the varifocal optics system 54 simulating proximity and far distance enhancing the visual stimuli perception, the eye tracking system 52, and the accommodation measurement system 56 including an Ocular Reflex Analyzer (ORA) assembly 104 that assesses the optical state of the eyes during an ongoing refractive examination. In some embodiments, the diagnostic device 102 may be coupled to the external computing device 36 including the controller 40 programmed to execute computer instructions including the diagnostic programs for use in performing refractive errors assessment and NDDs (neurodegenerative diseases) screening based on eye movement abnormalities profiling. In other embodiments, the diagnostic device 102 may also include the controller 40.

In the illustrated embodiment, the varifocal optics system 54 is equipped with an optical mechanism for vision correction which is controlled electrically from the controller 40. An optics assembly 106 is coupled to a display unit 108 including a screen displaying visual stimuli, thus providing a controlled spatial plane in the patient's perception.

The eye tracking system 52 includes two sub-assemblies including the MEMS eye tracking assembly 68 and the CMOS 2D profile sensor assembly 81. The MEMS eye tracking assembly 68 is configured to detect eye position measurement providing high temporal and spatial resolution with ~1 arc min accuracy providing precise eye movement data. The CMOS 2D profile sensor eye tracking assembly 81 is configured to acquire eye movement information with ultra-high temporal resolution allowing to assess e.g. saccade latency relative to the displayed stimulus.

The ORA assembly 104 includes two sub-assemblies including a projection assembly 110 and an acquisition assembly 112 and beam splitter 114 used in the circuit to enable cooperation between the projection assembly 110 and an acquisition assembly 112. The projection assembly 110 includes a NIR projection module that generates markers obtained from image projection onto the retina and cornea. The acquisition assembly 112 provides a system for testing the ability to assess changes in the focus plane of the eye lens and is designed to analyze accommodation responses of the patient's eyes. The controller 40 may include a computation and control unit with pre-installed software for local data analysis and providing data output.

Figure 18:
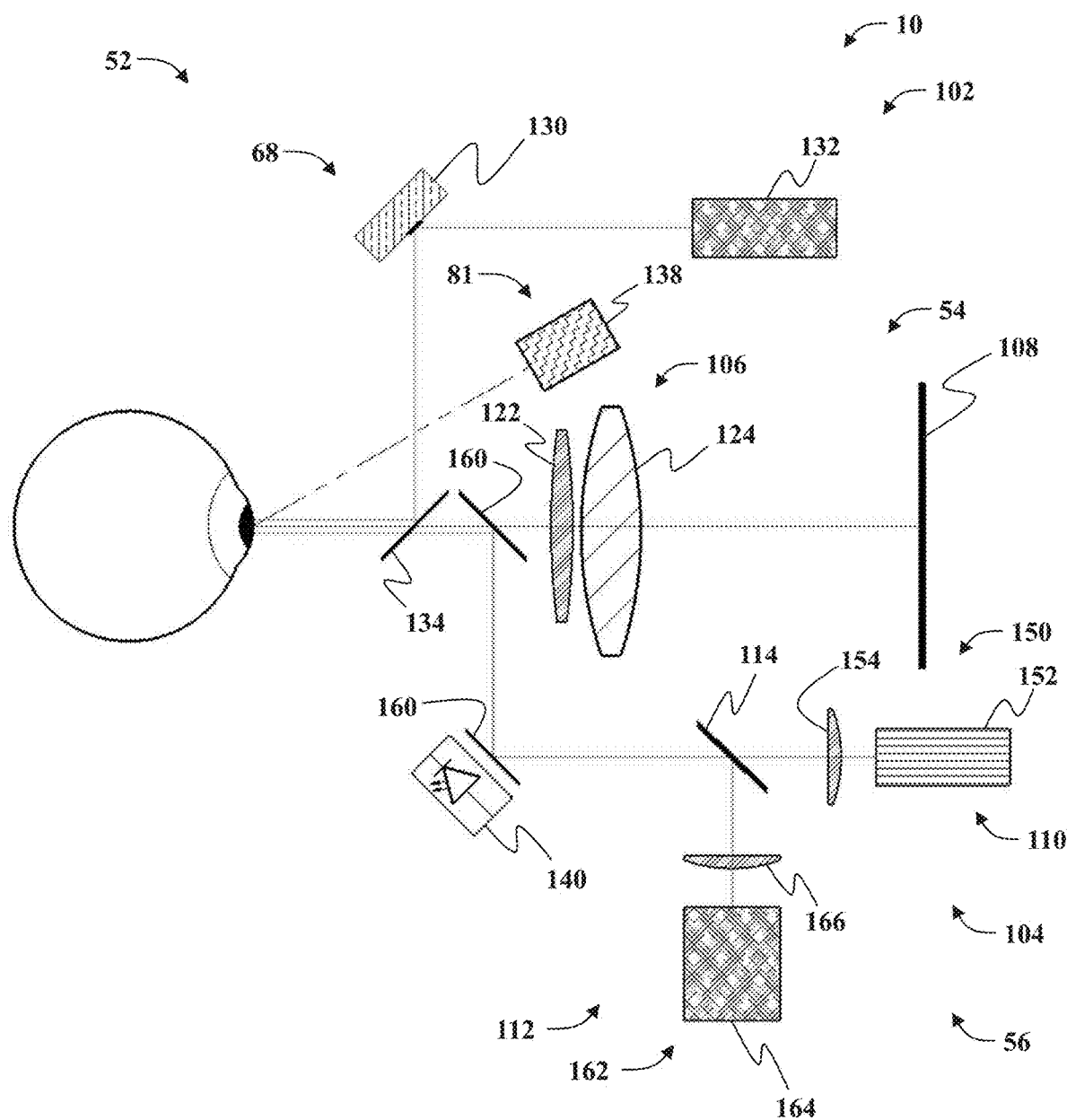
FIG. 18 is a schematic diagrams of the system including a diagnostic device, according to embodiments of the present invention.
Figure 19:
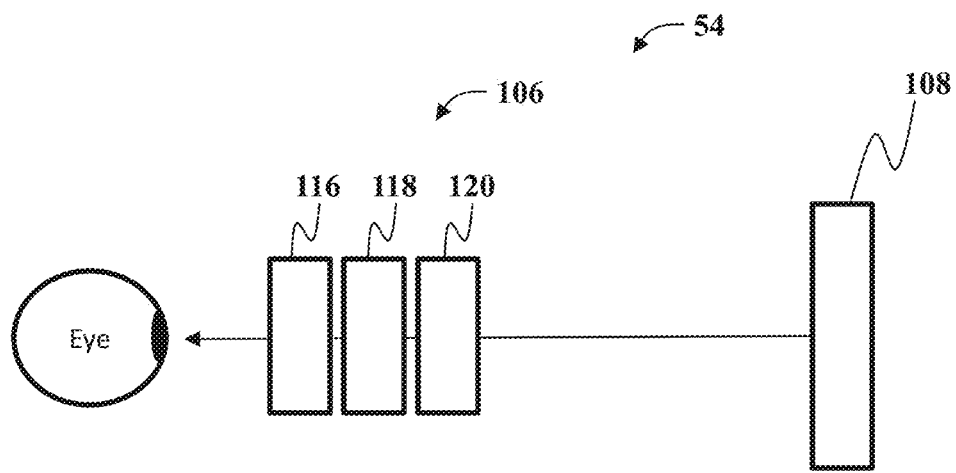
FIGS. 19 and 20 are schematic diagrams of a varifocal optics system that may be used with the system shown in FIGS. 3 and 18.
Figure 20:
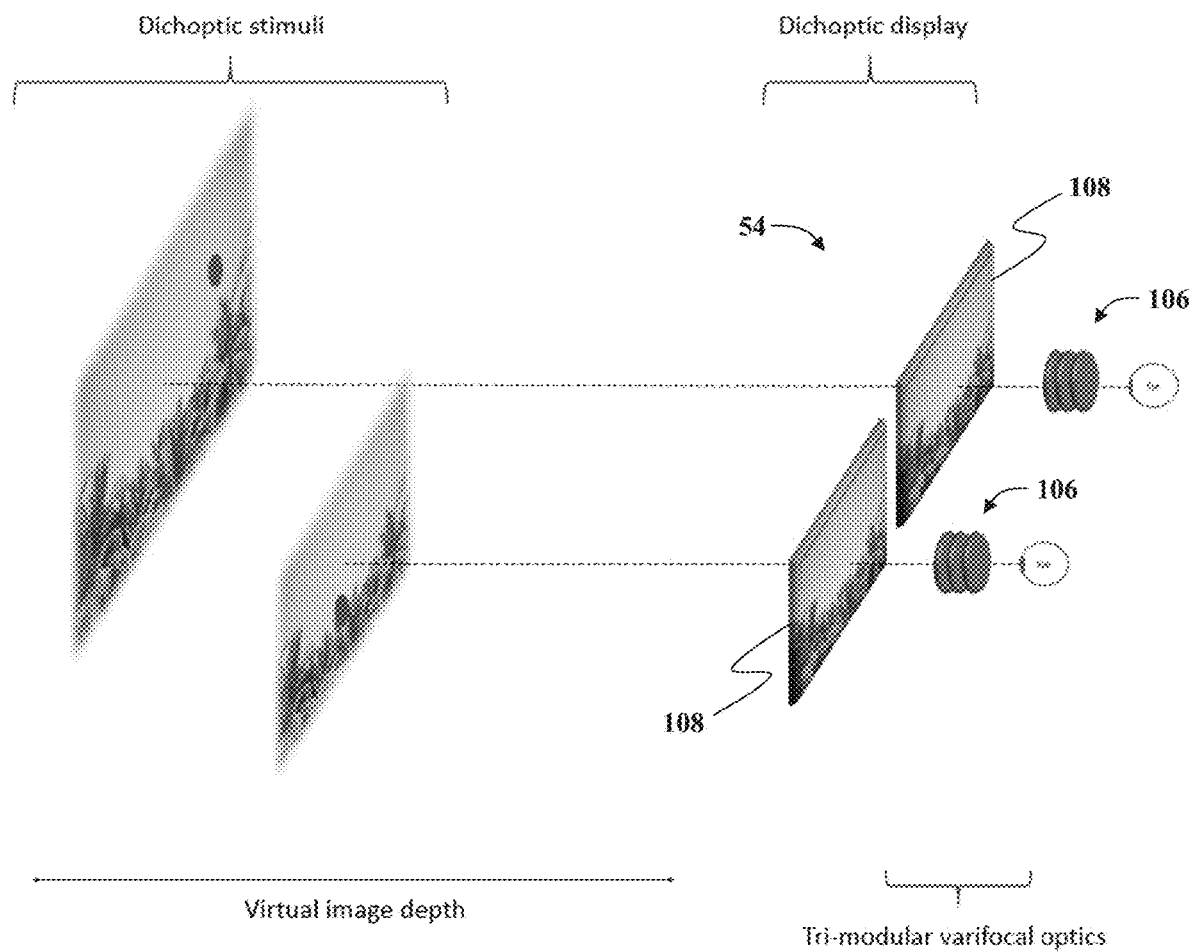

Referring to FIGS. 18-20, in some embodiments the varifocal optics system 54 may include a stimuli projection assembly 110 that includes the optics assembly 106 positioned between a display unit 108 and the patient's eyes. The optics assembly 106 may include a tri-modular varifocal optics including an electrically controlled cylindrical optics 116 providing with astigmatism correction, an electrically controlled varifocal optics 118 providing with spherical correction, and an electrically controlled varifocal optics 120 providing virtual image synthesis at set depth distance. The display unit 108 is coupled to the controller 40 and configured to render dynamically adjusted, dichoptic visual stimuli (VIS/RGB) including set of visual features adjusted in the line of currently used test scenario. In other embodiments, as shown in FIG. 18, the optics assembly 106 may include an electrically tunable lens 122 and a fixed lens 124 positioned between the electrically tunable lens 122 and the display unit 108.

The varifocal optics system 54 can be implemented by combining components among a group of solutions like: single varifocal metalens, plurality of varifocal metalenses, Jackson cross cylinder, set of Alvarez lenses, set of movable lenses with variable relative distances.

As shown in FIG. 20, in some embodiments, the varifocal optics system 54 includes a stimuli projection assembly 110 associated with each of the patient's eyes to include an optical design that provides a binocular projection of the visual stimulus, where the stimulus may have different features displayed independently to the left eye and the right eye. This opens a possibility of conducting additional set of tests designed for binocular vision disorders, which is important for holistic vision assessment. This component also is included into NDD screening results. In some embodiments, the varifocal optics system 54 may include a field of view provided by the optics around 40~ degrees as sufficient for its purpose.

The varifocal optics system 54 may be electrically controlled from the controller 40, without human intervention. The optical state is defined by the scenario of a given test and its course. The Principles behind module design are related to the requirements of two major use cases: 1) Simulation of various refractive correction states acting as an equivalent of adjustable glasses or contact lenses. Providing patient with different optical conditions is a basic principle behind subjective refraction done by an optometrist. During operation of the system 54, managing the optical conditions is preceded by data collection done by the eye tracking system 52. Those data are further processed to analyze micro-saccadic eye behavior and provide with an outcome aiming to suit best refractive correction. 2) The varifocal optics system 54 is capable of substitute refractive correction and creates perfect conditions for excluding need of wearing corrective glasses/lenses during NDD screening part. Any obstacle between the lens and the eye influences eye tracking data quality. Mitigating this issue is crucial to obtain best possible data reflecting eye movements.

Referring to FIGS. 18 and 21-26, in some embodiments, the MEMS eye tracking assembly 68 is configured to analyze ocular movements in frequency up to 1000 Hz and accuracy 1 arcmin (including saccades, micro-saccades). Known eye tracking modules are based on NIR cameras, proper lighting, bulky head-mounting and image processing, which leads to limited accuracy and frequency of tracking and high computing power demands. Moreover, the highest data quality of known system could be only obtained by scientific grade equipment that costs over 30-50,000 USD.

Figure 21:
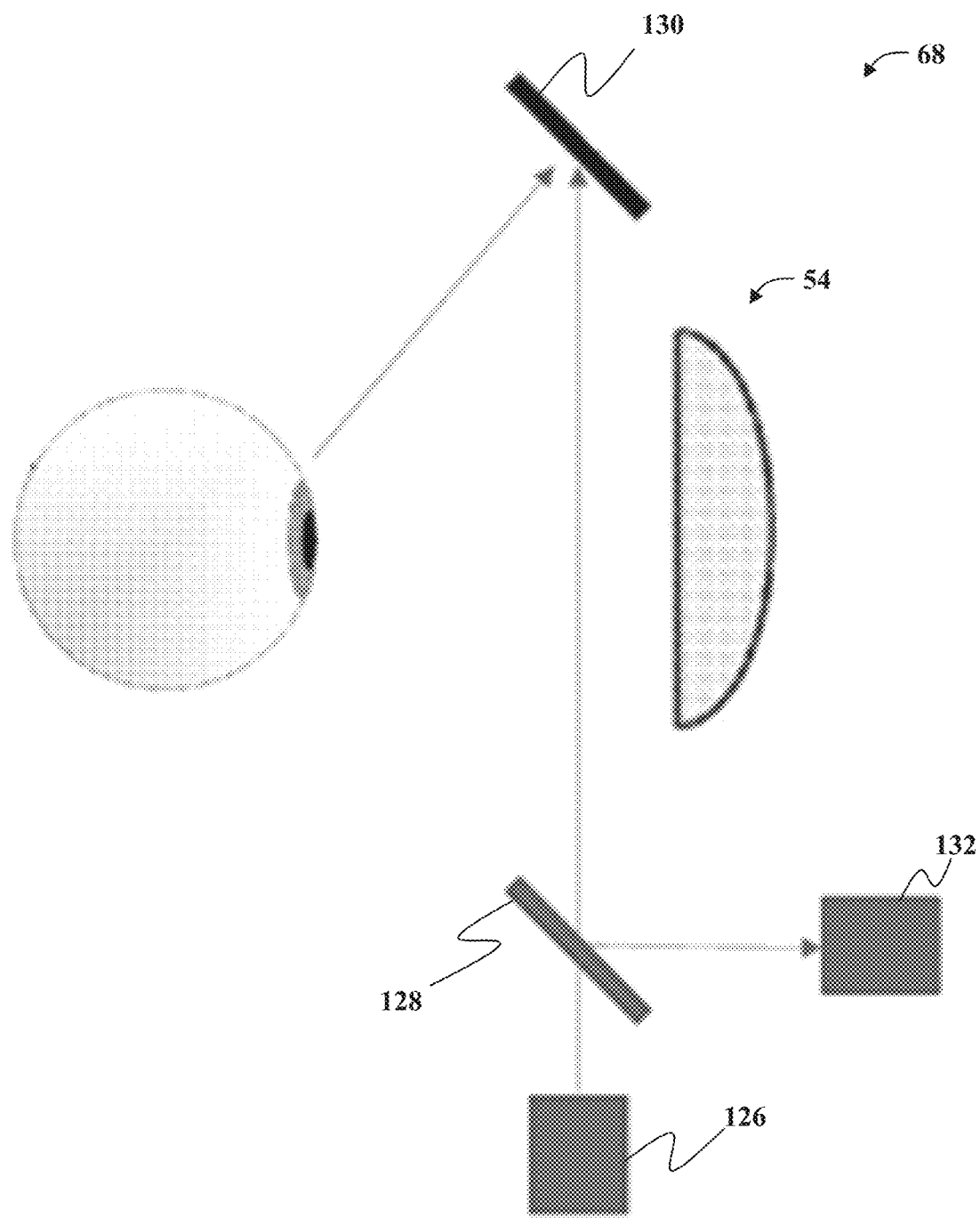
FIG. 21 is a schematic diagram of the eye tracking system including a micro-electro-mechanical systems (MEMS) assembly that may be used with the system shown in FIGS. 3 and 18.

As shown in FIGS. 18 and 21, the MEMS eye tracking assembly 68 may include a laser diode 126 providing illumination by emitting a beam which, through a beam splitter 128, reaches a moving MEMS mirror 130 and, after reflection, is reflected onto an object (eye) or through homogeneous illumination system using LEDs. The mirror (electronically controlled) changes its angular position within the available range by changing the applied control voltage. The movement of the mirror 130 results in a change of the laser beam's point of contact with the eye. The beam after lighting the object is reflected (dispersed). This reflected radiation emitted back passes through the moving mirror 130 and beam splitter 128 again and then falls on the detector 132. Changing the angular position of the mirror causes the laser beam to pass through the object alternately falling on the area of sclera, iris, pupil. In some embodiments, as shown in FIG. 18, the MEMS eye tracking assembly 68 may include a Hot mirror 134 for reflecting the beam to/from the MEMS mirror 130.

Individual areas have different reflective characteristics, which results in a difference in the amount of radiation returning to the detector. A measurable effect is change of the amplitude of the signal when the beam is dispersed in the pupil's area in relation to the signal coming from the sclera area. By analyzing the variation in time of the signal obtained in comparison with the information about the position of the mirror, the position of the center of the object (i.e., the eye pupil) can be estimated. In order to optimize the computational model, a specific MEMS assembly operating in control mode may be implemented, where the slow axis is controlled linearly, and the second, fast axis operates in resonant mode.

Based on the stimuli scenario, system may limit maximum angle of MEMS mirror 130 swing and/or actuate entry base position of the MEMS mirror 130 according to estimated position of the pupil given by the scenario and content. Actuation of entry base zero point of MEMS (initial position) can be done by MEMS module 68 itself or it can be realized by an external actuator combined with MEMS module 68.

Figure 22:
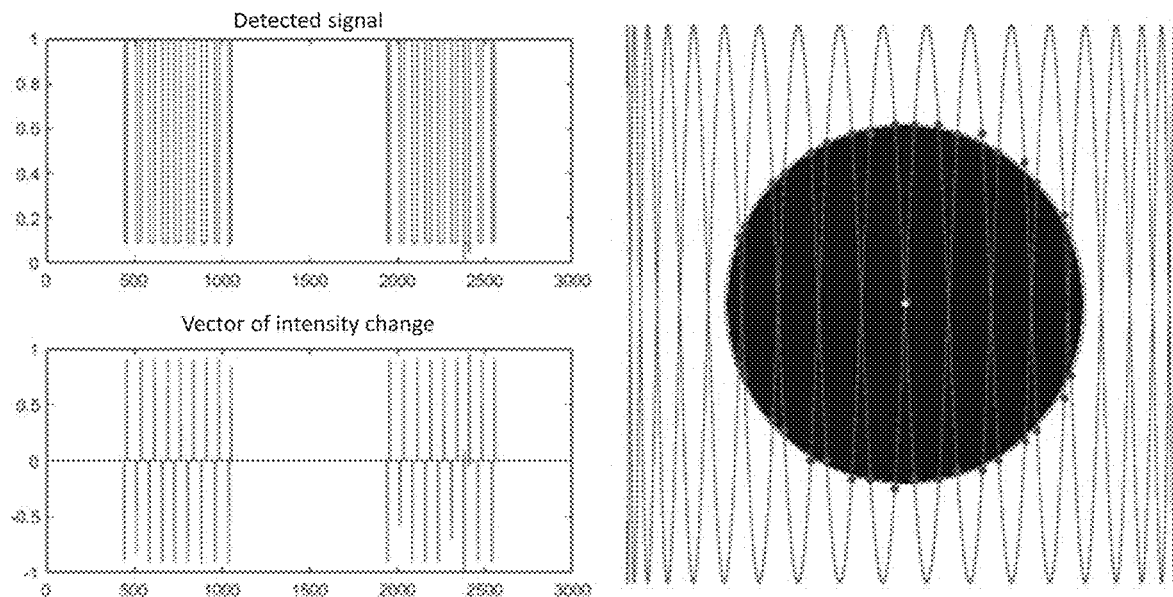
FIGS. 22-26 are illustrations of the algorithms that may be executed by the system for use in operating the eye tracking system including the MEMS assembly shown in FIG. 21 to track movement of a patient's eyes.
Figure 23:
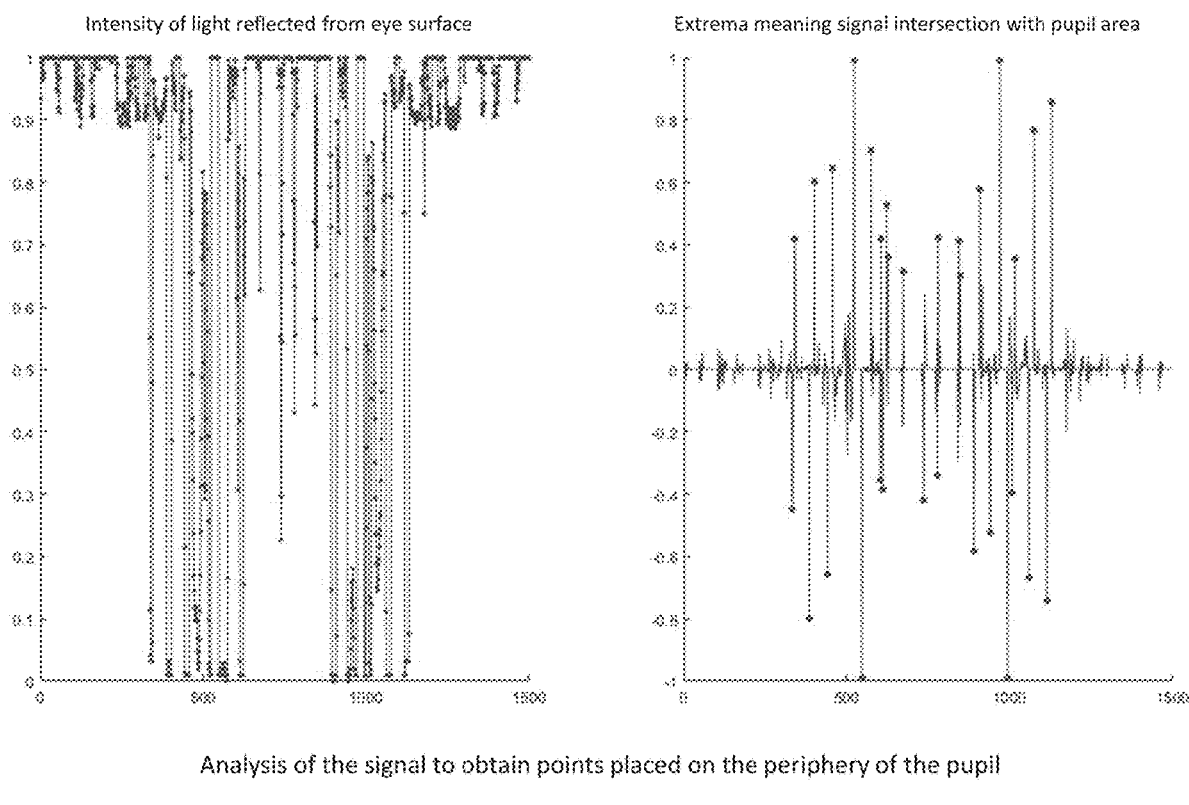
Figure 24:
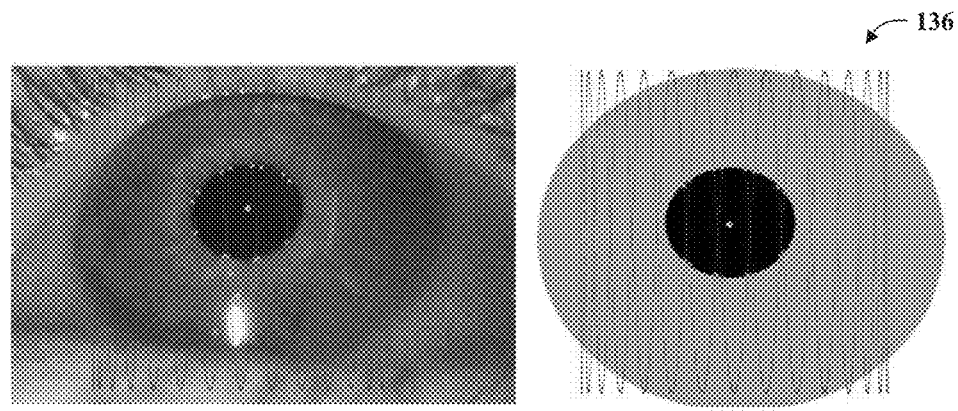

Referring to FIGS. 22-26, in some embodiment, the controller 40 may be programmed to execute a MEMS scanning method algorithm 136 operate the MEMS eye tracking assembly 68 to detect and analyzes a position and movement of a patient's eyes. For example, to detect the intersection points of the pupil area, the change in signal intensity is taken into account. Therefore, after detecting the local extremes of the vector, the gradient of the slope is analyzed, which indicates the suddenness of the signal change. In order to count the extremes as pupil peripheral points, the value of its derivative must exceed a predefined threshold. An additional criteria is the temporal separation of the points—knowing the course of the curve, it is possible to estimate how often the intersection of the pupil area may occur. Points highlighted but placed below this criterion are also discarded. FIG. 22 shows a plot of the reflected signal intensity and the pupil edge points that emerge from it. During a single period of the slow axis, the signal scans the area twice—back and forth. Therefore, the pupil area is scanned twice, as can be seen in the graphs.

In the course of further analysis, the determined points are compared with the model of the curve of mirror movement. On this basis, a 2D image of the point distribution is obtained by using points determined as placed on the pupil's periphery. Then, based on the method of least squares or analysis of the positions of the function maxima, an ellipse estimating its edge is determined.

Figure 25:
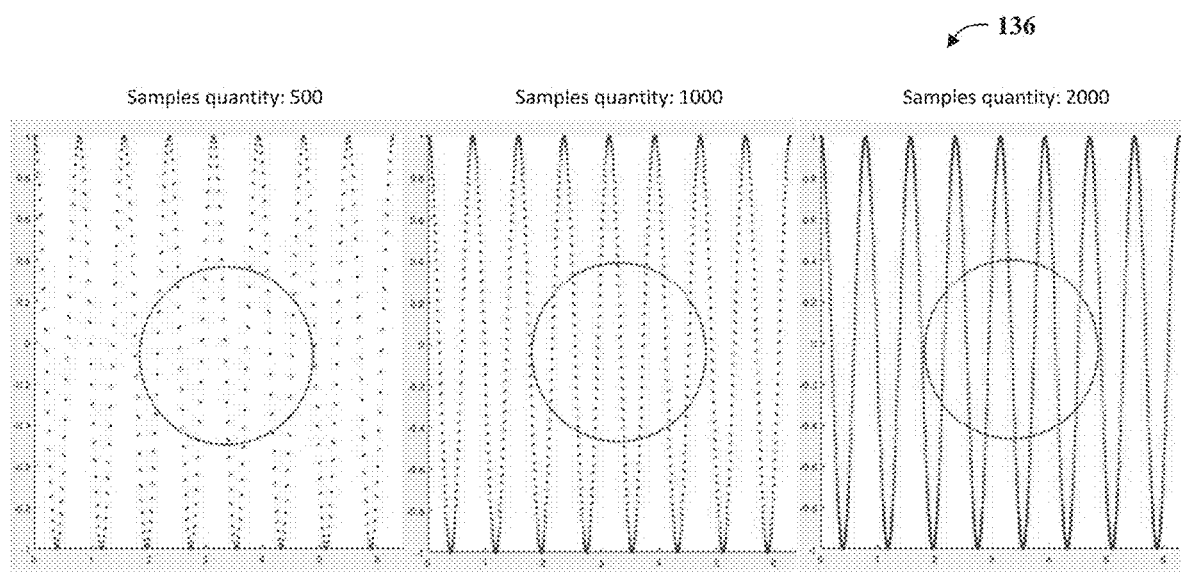

A number of method parameters affect the accuracy of pupil position determination. One of them is the number of detection samples. The quantity of detection samples is directly proportional to the sampling rate of the signal. The idea of the effect of sampling rate on the number of points of intersection of the pupil area is shown in FIG. 25. The black circle indicates the edges of the sample pupil.

Eye movements detection: Available eye tracking technology in its principles focuses in the first place on determining the gaze points (often in on-line mode). Usually, it is used to allow user to interact with the content directly through the gaze. In some cases, it is used also to analyze user attention or other behavioral parameters. This approach defines set of needs dictating module design (both from hardware and software perspective).

The present MEMS scanning method solution evolved on the basis of another requirements resulting from strictly defined applications in eye care and neurology sectors. The primary objective of the MEMS scanning method is to provide the system 10 with the data describing eye movements characteristics, emphasizing those ones occurring in the micro scale. For example, the eye tracking system 52 may be configured to provide a data set collected and processed within disclosed system to create Ocular Movement Abnormalities Profile comprised of the following parameters: 1) Saccades: Amplitude, Peak Velocity, Duration, Latency; 2) Smooth pursuits: Initial acceleration, Peak velocity, Velocity at set time points, Latency; 3) Intersaccadic drift; 4) Ocular micro tremor; 5) Optokinetic nystagmus; and 6) Pupillary light reflex.

The results are obtained through comparing and subtracting single data frames storing information about spatial characteristics of selected eye features e.g. retina position. A single frame is collected during each scan (half of the period), done within maximum operating range angles (2D, two axes). Those frames are assigned to appropriate time signatures coming from MEMS mirror assembly 68 and/or 2D profile sensor. Combination of those means complete data stack that is further processed to the final output describing temporal and spatial properties of eye movements.

The eye tracking system 52 is also capable of gaze point determining similar to other eye tracking solutions. However, it wasn't a main goal of a module design and idea. Gaze points data may be obtained through 2D profile sensor (as an on-line input) due to the simplified computing model in comparison to MEMS mirror approach. Those may be used for assessing if user follows the visual task scenario properly.

Figure 26:
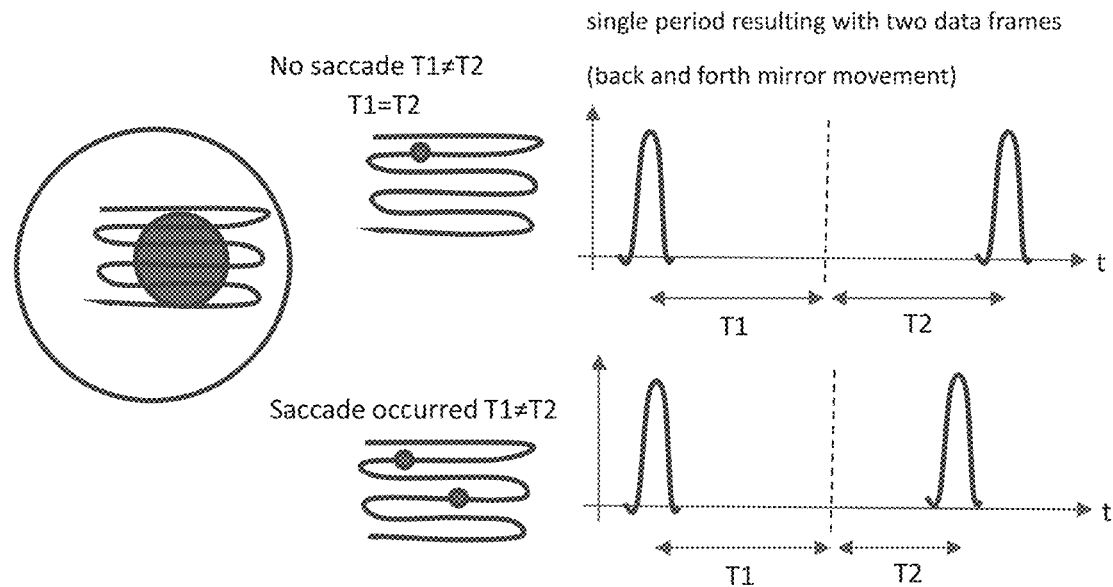

The basic principle of eye movements assessment is illustrated by FIG. 26. Occurrence of the eye movement is related to implemented thresholds identifying particular types of ocular behavior. Classification to those may utilize machine learning computation models. Since the eye is in constant motion, the lack of difference between T1 and T2 applies to the theoretical, simplified model. Spatial differences between those two frames are paired with time signatures, then processed to obtain final outcomes.

Referring to FIGS. 18 and 27-30, the CMOS 2D profile sensor assembly 81 includes a 2D sensor profile as an alternative approach to existing eye-tracking technology. Unlike camera-based solutions that rely on image-based eye movement tracing, the CMOS profile sensor is a high-performance sensor designed to acquire projection data in the x and y dimensions. The application of this solution gives the possibility of acquisition and processing the measurement data in a remarkably short time. Using a combination of two-axis information (x-axis and y-axis profile data) extracted from the profile sensor, achieves the ability to detect the position of the eye pupil at a fast rate and satisfactory resolution with small digital computation.

Figure 27:
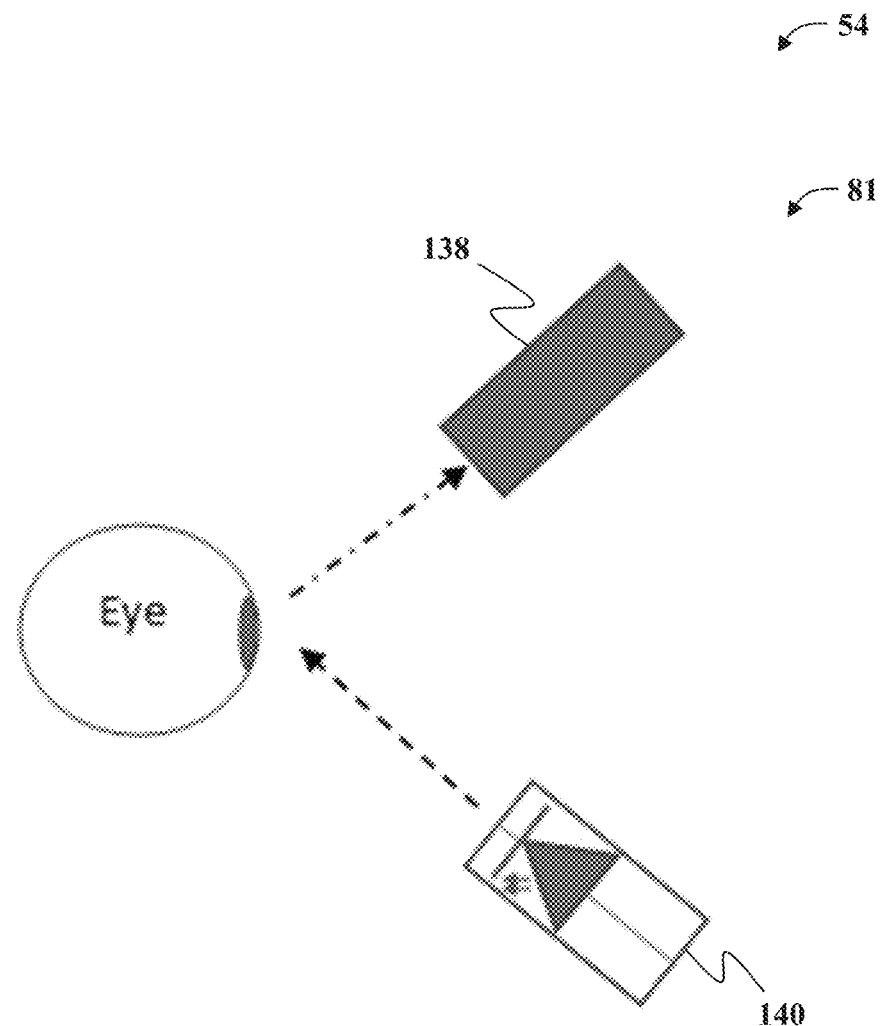
FIG. 27 is a schematic diagram of the eye tracking system including a CMOS 2D profile sensor assembly that may be used with the system shown in FIGS. 3 and 18.

Eye-tracking based on the CMOS profile sensor is essential for the system in terms of rapid data acquisition for eye movement analysis. A simplified measurement scheme is shown in FIG. 27. Basic setting of the CMOS profile sensor assumes a profile analyzer sensor 138 that is orientated on one side of the eyeball, so that its detection center is positioned on the sclera. On the other side of the eyeball a light source 140 is located, which homogeneously illuminates it. This position of the profile analyzer sensor 138 and light source 140 in relation to the eye enables to obtain measurements both from the sclera and pupil of the eye.

Figure 28:
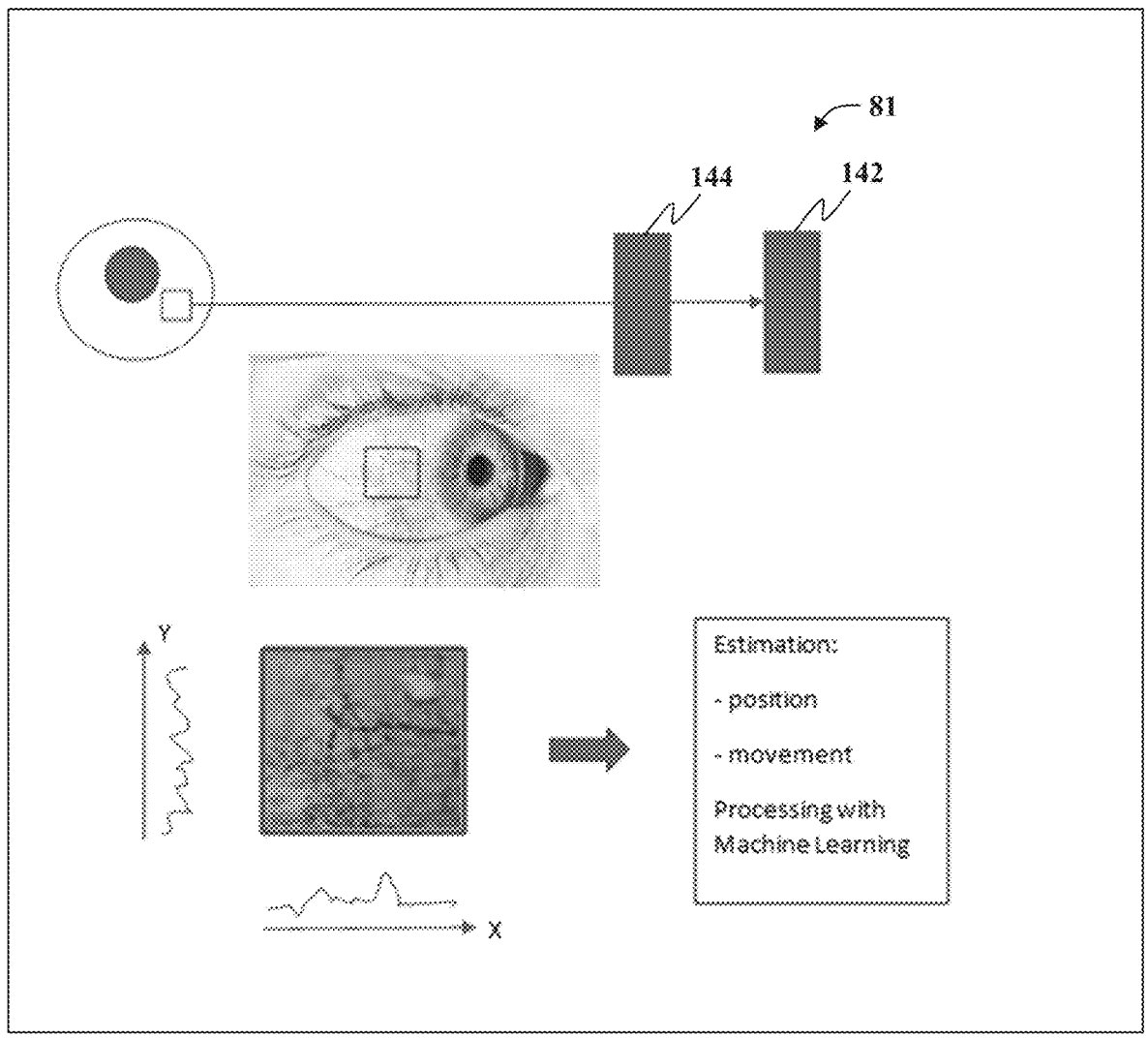
FIGS. 28-30 are illustrations of the algorithms that may be executed by the system for use in operating the eye tracking system including the CMOS 2D profile sensor assembly shown in FIG. 27 to track movement of a patient's eyes.

Referring to FIG. 28, a schematic of a measurement system using the CMOS profile sensor may include a 2D profile sensor 142 and a varifocal optics 144 for image formation on the sensor. The varifocal optics 144 is placed in front of the profile sensor 142 to allow manipulation of the image that will form on the sensor. This system provides position and eye movement estimation using a profile sensor. Neural networks (machine learning) are used to analyze the data acquired from the proposed method.

In some embodiments, the proposed measurement scheme implemented by the CMOS 2D profile sensor assembly 81 may involve placing several profile sensors 138 at different positions relative to the eyeball, where each sensor profile will perform a different function. As shown in FIG. 28, the sclera pictured under magnification shows blood vessels. This gives the ability to detect motion based on the changing pattern of vessels in the detector field of view.

Figure 29:
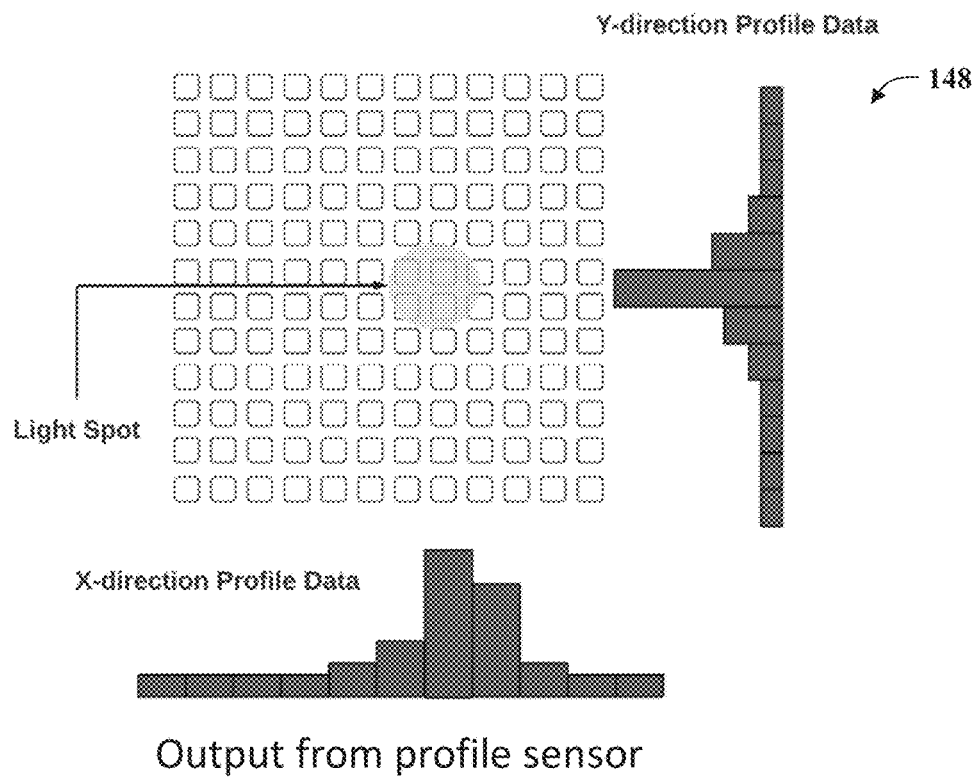
Figure 30:
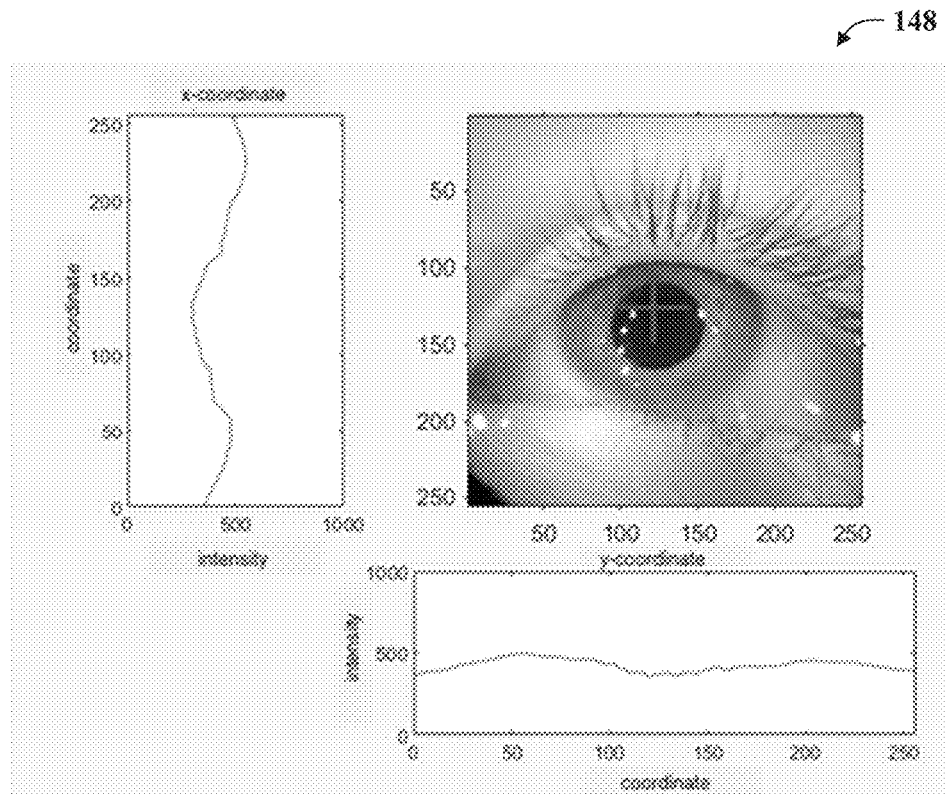

Referring to FIGS. 29-30, the system may be programmed to execute a measurement method algorithm 148 to operate the CMOS 2D profile sensor assembly 81 to detect and analyzes a position and movement of a patient's eyes.

The CMOS 2D profile sensor assembly 81 is designed to work independently (i.e. it does not use data contained in other modules). However, the measurement data from the profile sensor assembly 81 will be crucial for the operation of the whole system, because as a separate unit, this profile sensor assembly 81 will be able to determine the position of the eye over its entire range of motion.

The CMOS 2D profile sensor assembly 81 also contributes significantly to the operation of the display by giving feedback to the controller 40 on where to project the accommodative response stimulus for the other measurement systems.

The proposed CMOS 2D profile sensor assembly 81 is a unique adoption of CMOS image sensor. It consists of an array of pixels placed vertically and horizontally at equal distances from each other. Each pixel is in fact a photodiode. Their function is to detect the intensity of light reaching a given area of the sensor. The measurements are then processed using neural networks.

For example, FIG. 29 illustrates a spot where a light is detected in active area. The detection of profile data recorded by the 2D CMOS profile sensor follows the X and Y axes. For the Y-axis, the profile data is the summation data taken from each row of pixel image sensor, analogously for the X-axis, the projection data is the summation data taken from each column of pixels. FIG. 30 illustrates an example reading of data acquired from a profile sensor, which shows the practical application of the schemes discussed in this issue. In this application, the system looks for minima in the X and Y plots that indicate the center of the pupil.

This CMOS type of sensor operates at very high temporal resolution. The spatial resolution, however, is subject to high error here. As part of the eye tracking system, this sensor primarily enables the analysis of temporal parameters related to the occurrence of eye movements. Of particular importance here is the saccade latency relative to the displayed visual stimulus. The analysis of this parameter is crucial within the test scenarios associated with a group of neurodegenerative disorders. The results of recent studies indicate, for example, that subjects with anisometropic amblyopia have a longer latency of saccadic movements in the visually impaired eye compared to the guiding eye, it appears that not only in the context of visual anomalies but also in neurological disorders similar cases can be observed. In these cases, it is not the precision of the eye movements that is significant, but obtaining an estimate of the entire eye path in a short period of time. This allows analysis of the movement of the eyeball based on the direction and speed of its movement.

Figure 31:
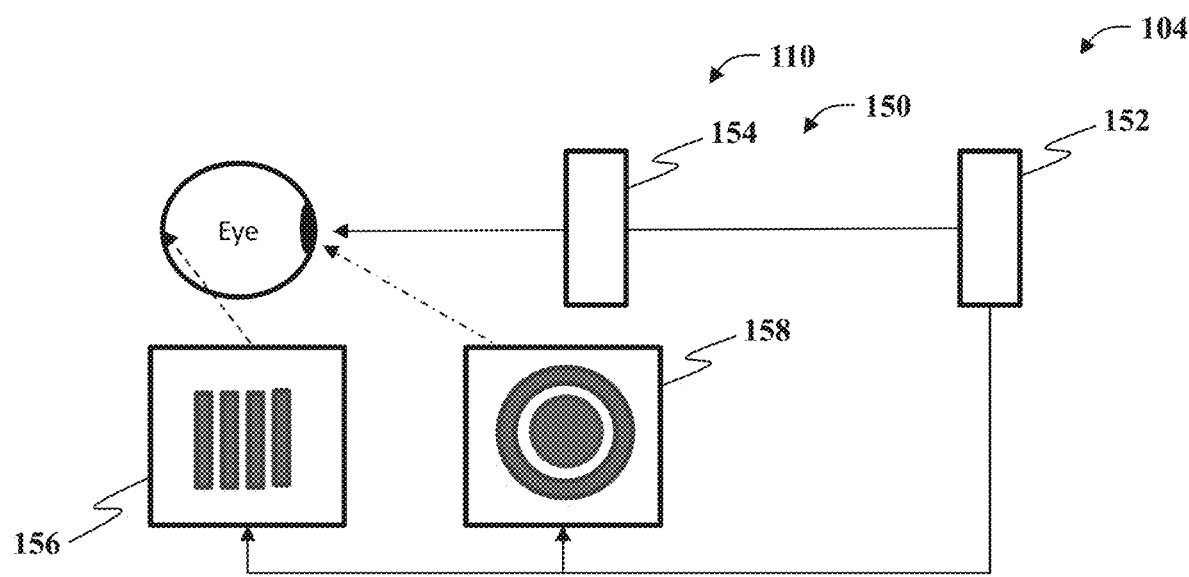
FIGS. 31 and 32 are schematic illustrations of the accommodation measurement system including an ocular reflex analyzer (ORA) assembly including illustrations of the algorithms that may be executed by the system for use in ORA assembly for use in evaluating changes in the focal plane of the patient's ocular lens.
Figure 32:
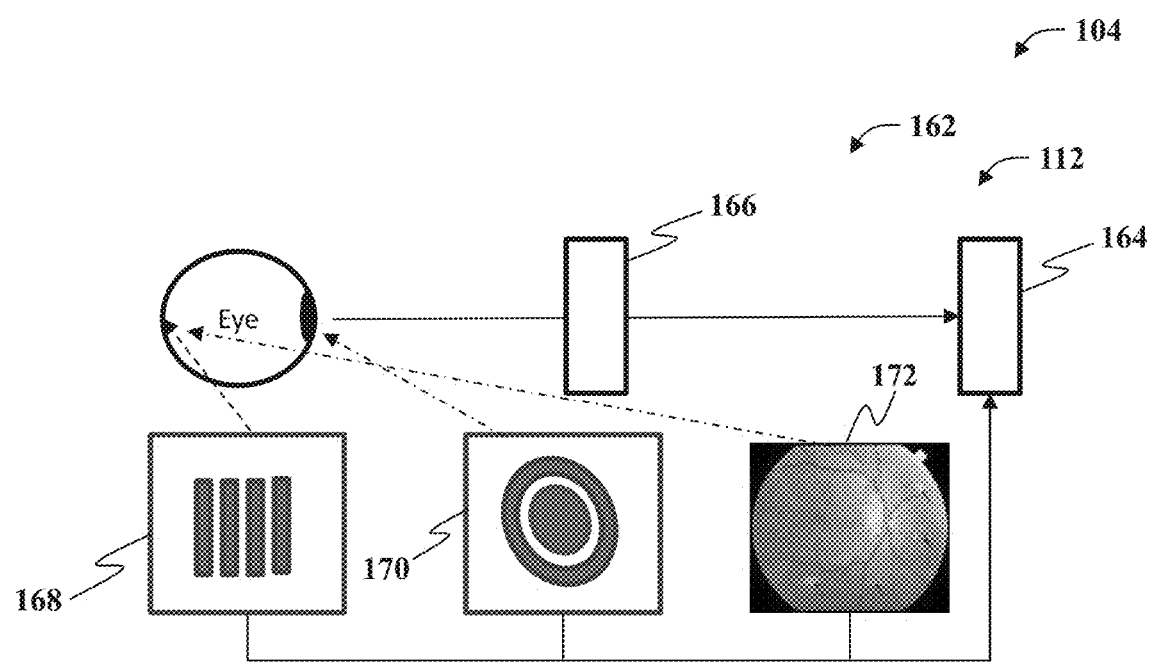

Referring to FIGS. 18 and 31-32, the ORA assembly 104 provides a system for investigating the ability to evaluate changes in the focal plane of the ocular lens. The ORA assembly 104 is a solution, composed of two sub-assemblies including the projection assembly 110 and the acquisition assembly 112. The projection assembly 110 is configured to generate a NIR marker. The acquisition assembly 112 is configured to perform marker detection (light signal reflected from the eye region) and further analysis. The two assemblies work concurrently. Synchronization of the operation of both systems of these assemblies is achieved by performing a calibration procedure.

As shown in FIG. 31, the projection assembly 110 may include a NIR marker projecting module 150 that is designed to produce an image on both the retina and the cornea of the eye. The NIR marker projecting module 150 operation simulates a change in the distance of an object observed by the eye. Thus, by manipulating the focal length of the system, it is possible to obtain the markers of a specific eye element. A NIR marker is a slit with a modified width and variable position relative to the optical axis of the marker projector. The marker will be optically projected on the retina and the cornea. The image of the marker passing through the eye lens twice (in the direction of eye and back) will be modified, which is registered by the dedicated system of acquisition. The analysis of the variability of such an image (as a result of changes in the accommodative distance) is the basis for assessing the occurring changes in the optical system of the eye. In some embodiments, the NIR marker projecting module 150 includes an NIR display 152 and a varifocal optics system 154 for image synthesis of the measurement marker including: a) retinal reflectance marker 156 for accommodative and astigmatism analysis; and b) corneal reflex marker 158 for the analysis of astigmatism.

A key component of the ORA assembly 104 is the NIR display 152. Operating at a wavelength of near-infrared light allows to enter into the system a measurable object that is safe and invisible to the human eye. The second element of the module, the varifocal optics system 54, allows changing the distance of the virtual image. This can be implemented by using components among a group of solutions like: single varifocal metalens, plurality of varifocal metalenses, Jackson cross cylinder, set of Alvarez lenses, set of movable lenses with variable relative distances. The NIR marker projecting module 150 will generate two markers, which will be obtained by changing the length of the optical system. The marker obtained by image projection onto the retina works directly with the accommodation analyzer, additionally the marker of image projection onto the cornea will be integrated with the astigmatism analyzer. In some embodiments, as shown in FIG. 18, the ORA assembly 104 may include a beam splitter 114 and a plurality of Hot mirrors 160 for reflecting near-infrared light from the NIR display 152 towards the patients' eyes and towards the acquisition assembly 112.

As shown in FIG. 32, in some embodiments, the acquisition assembly 112 may include a reflex acquisition module 162 to analyze the image of the generated reflex as a function of changing optical parameters of the eye (focus distance/focal length change in relation to the distance to the observed object/synthesized apparent image). The reflex acquisition module 162 is used evaluate changes in the focus plane of the eye lens.

The reflex acquisition module 162 includes an image sensor 164 and varifocal optics system 166 for image generation on the sensor. With a varifocal optics system 166, the image formed on both the retina or cornea can be altered, providing the ability to adjust the focal length of the system to the optical power of the eye lens. The element "closing" the path of optical radiation in the measuring system is the lens of the eye. The path of the optical radiation in the reflex acquisition module 162 begins at the marker projector described above.

For example, as shown in FIGS. 31-32, the optical radiation pathway begins at the NIR marker projector 150, passes through the ocular lens, reflects off the retinal/cornea of the eye and returns passing through the ocular lens again, then directs to the eye reflectance detector 164 (image sensor).

The acquisition assembly 112 in the basic version may include an image sensor 164 and varifocal optics system 166 for image formation on the sensor. The controller 40 may be programmed to operate the acquisition assembly 112 to perform: (a) retinal reflectance analysis 168 of the marker for accommodative analysis, which by analyzing the sharpness of the image of the measurement marker formed on the retina, pathological changes can be detected; (b) corneal reflectance marker analysis 170 for astigmatism analysis—Based on the analysis of the deformation of the marker projected on the cornea, possible pathological changes such as astigmatism are inferred; and (c) retinal image analysis 172 (ophthalmoscopy)—This functionality will produce fundus images using Machine Learning and the operation of neural networks. This type of images gives information about abnormalities in the structure and functioning of the retina, choroid membrane and optic nerve.

In some embodiments, the ORA assembly 104 may provide an initial objective refraction measurement supporting the automated decision making and giving initial estimation of refractive errors for disclosed, novel procedure for refractive eye exam. In regular refraction routine (both binocular and monocular), it is important to control accommodation response. During a subjective refraction accommodation must be not be allowed to fluctuate randomly. The eye should be as relaxed as possible so that changes in the accommodative state do not influence the end-result. The gold standard for measuring refractive error in children's population studies is with cycloplegia because of its ability to control accommodation. Inadequate control of accommodation can impact on refractive error measurements in children, particularly with regard to hyperopia. Noncycloplegic measurements, using either autorefraction or retinoscopy, have been shown to underestimate the hyperopic refractive state of a child; this underestimation is referred to as latent error. However, there are a number of disadvantages associated with cycloplegia, including time, discomfort, cost, and inconvenience. Accordingly, cycloplegic refractions have not always been the method of choice in research settings, which creates a problem with population studies where comparisons are compromised by the different methods adopted to measure refractive errors. Optical fogging provides an alternative method of measuring refractive error, where accommodation is controlled by adding positive lenses in front of the eyes, to relax accommodation. Having an objectively collected feedback describing patient's accommodation state analyzed continuously during disclosed refraction method brings significant value for automated decision making process and data quality control. Moreover, continuously calculated ocular accommodation states may be compared to the predictive accommodation response models defined by test scenarios and determined baselines. Additional outcomes may indicate accommodation related vision problems like accommodation insufficiency or improper accommodation-convergence reflex.

Figure 33:
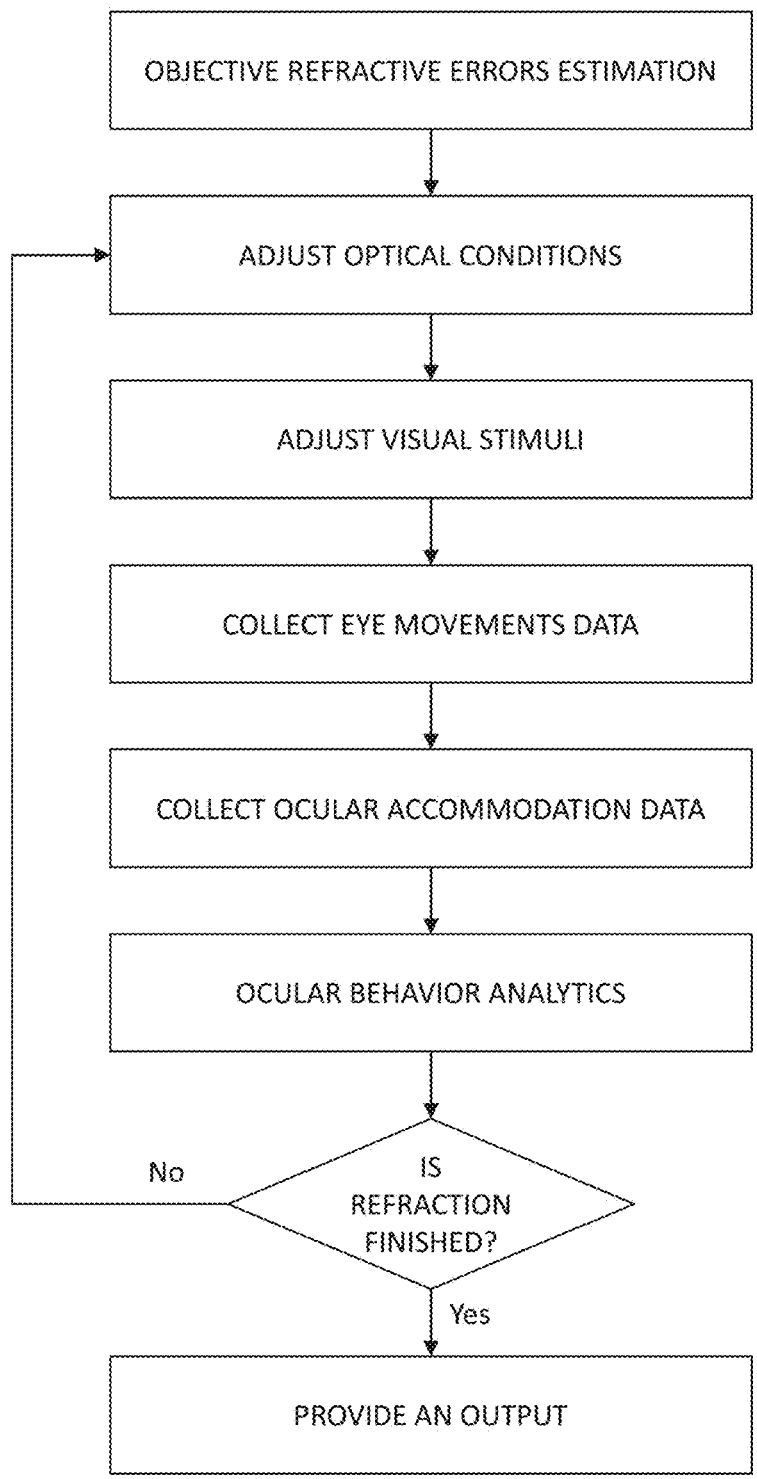
FIGS. 33 and 34 are flowchart of algorithms that may executed the system shown in FIGS. 3 and 18 for use in analyzing eye movements relative to visual stimulus and detecting eye movement abnormalities.
Figure 34:
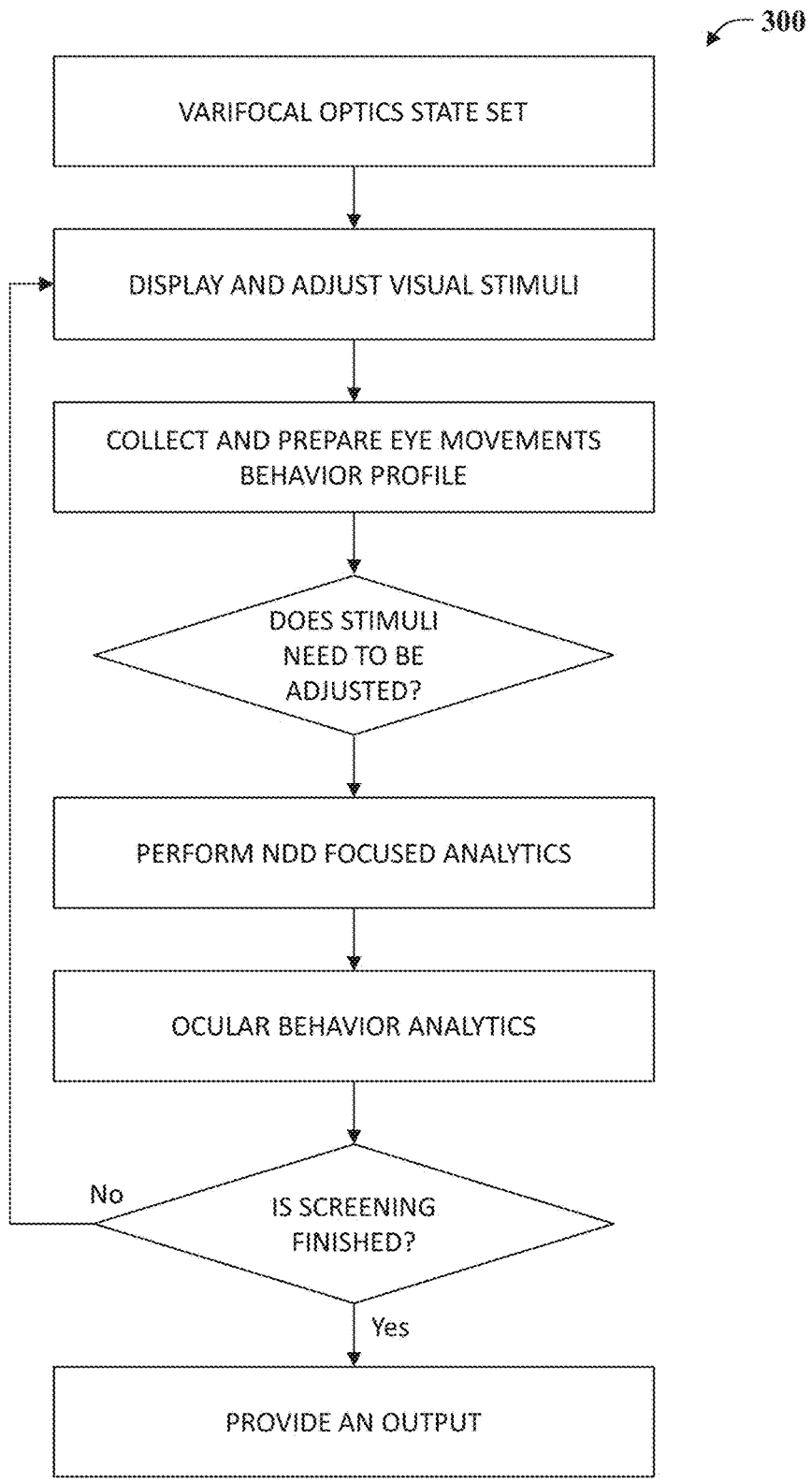
Figure 39:
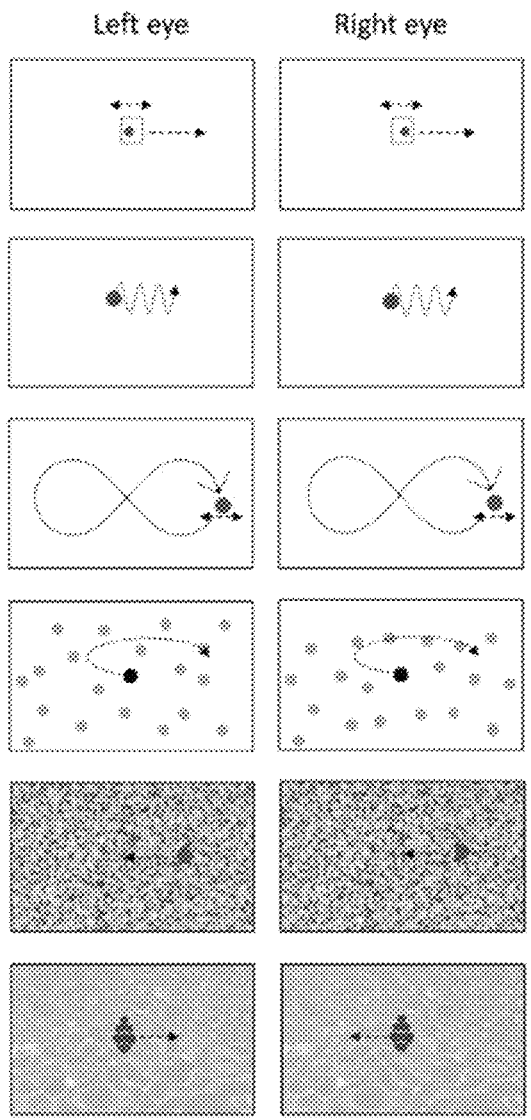
Figure 40:
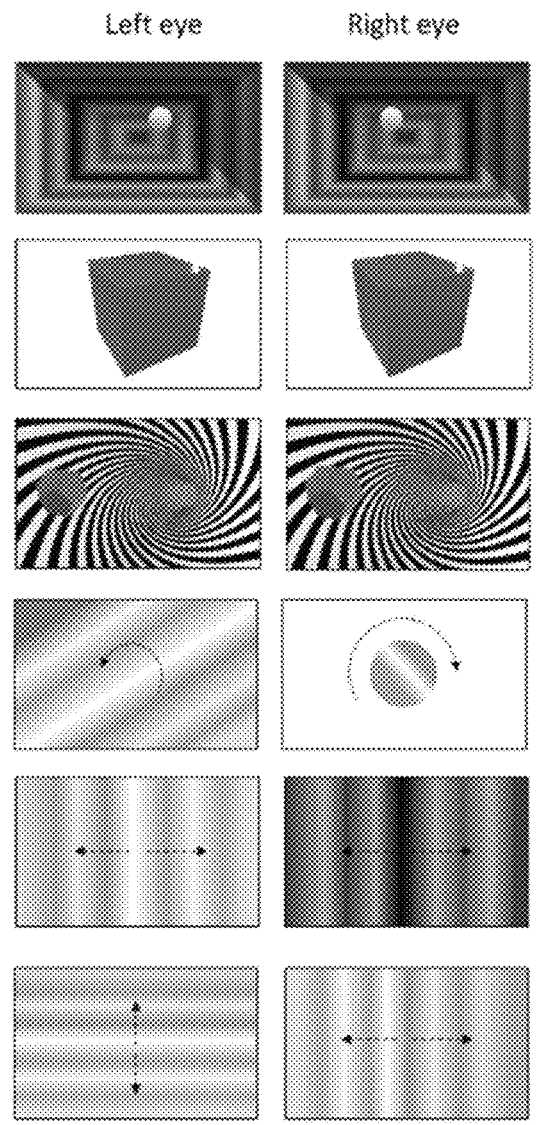
Figure 41:
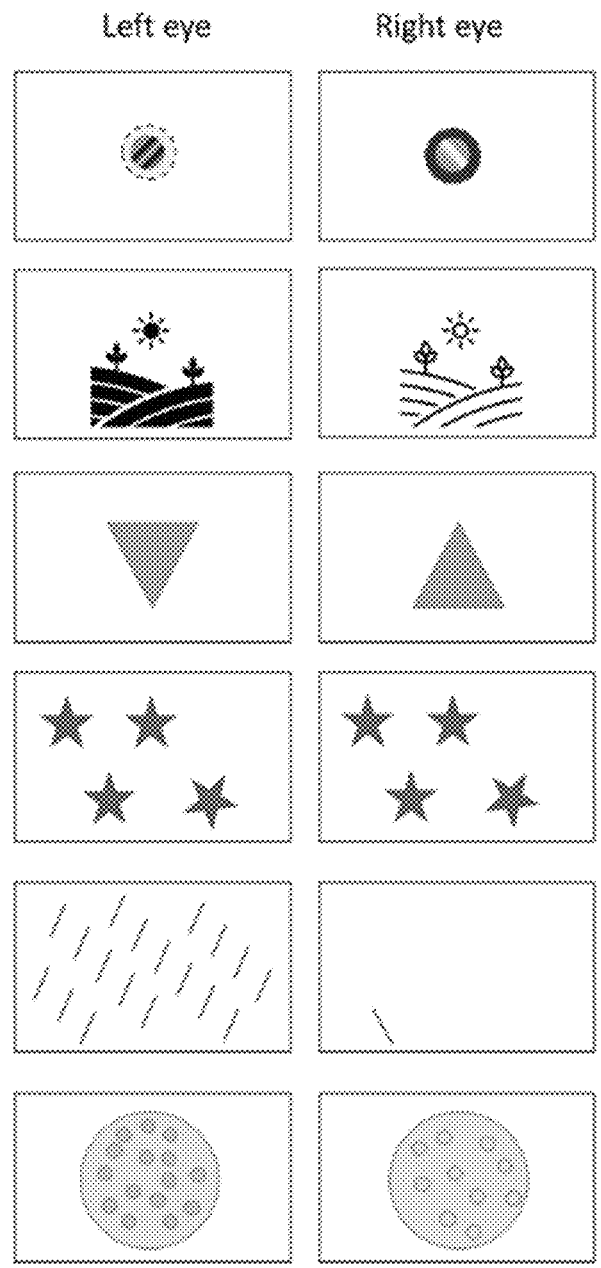

FIGS. 33 and 34 are flowcharts of methods 200 and 300 including a plurality of algorithm step that are executed by the diagnostic device 102 for precisely analyzing eye movements relative to a visual stimulus generated in a controlled depth plane. The methods 200 and 300 include a plurality of steps. Each method step may be performed independently of, or in combination with, other method steps. Portions of the methods may be performed by any one of, or any combination of, the components of the system 10.

In the illustrated embodiment, the controller 40 of the diagnostic device 102 is programmed to include an Ocular Movement Abnormalities Profiler (OMAP) module. The OMAP module is programmed to execute the algorithm steps of methods 200 and 300 to precisely analyze eye movements relative to a visual stimulus generated in a controlled depth plane. The diagnostic device 102 is designed as novel device offering unprecedented conditions to conduct such activities.

Data collected during the assessment creates unique, individual profile of ocular movement behavior and abnormalities. Mentioned profile may be used for the assessment performed in comparison to the health population determined baselines. Retrospective analysis compared to previous assessments of an individual (e.g. disease management support) means additional, valuable feature of application.

To meet the stated target, the system 10 projects through varifocal optics system a changeable and controllable, dichoptic visual stimuli with set depth distance. Additionally, system 10 implements eye tracking method of extreme accuracy and precision reaching ~1 arc minute. Use case determined objectives define a need for simultaneous observation of spatial and temporal features of retina position.

Relevant part of obtaining the results is that the NDD-focused screening procedure is not directly related with determination of the gaze points (which is main objective for most of the eye trackers). The approach is to focus on analyzing the movement behavior (especially micro-movements) of the eyes (based on retina position determination) in comparison to the reference eye movement model that is dictated by visual stimuli scenario with preset movement trajectories. The eye movement model features may be obtained e.g. during standardization procedures involving health people groups aiming to the define the baselines. In this context, calculating the gaze points doesn't play a major role. Gaze point data may be used for adjusting the visual stimuli features during the test, but it is not crucial for OMAP main target which is to quantize ocular behavior under changeable, controlled, dichoptic visual conditions.

Additionally, device manufacture cost needs to answer market circumstances like customer behavior or price sensitivity. The MEMS mirror approach combined with 2D profile sensor creates perfect conditions allowing for operating within very high spatial and temporal resolution of the measurement with kept business and usability aspects (especially in comparison to video-oculography). Eye tracking method implemented for presented purposes has to be user-friendly in a way non-limiting commercial implementations.

Varifocal optics being a part of the device will act in this scenario as internal refractive correction excluding the need of wearing eyeglasses during the test. It may significantly increase eye tracking performance through cutting of potential measurement distractors. As accuracy and precision is key factor in obtaining proper results, this feature brings great value.

Nowadays, refractive exams quality depends on optometrist skills and experience. A goal is to merge experience and outcomes gained from accumulated number of tests performed worldwide, which cannot be compared to a single optometrist's experience and insights. This leads to the development of new applications thanks to the ability of a unique data set to be processed.

Known video based eye tracking (video oculography, VOG) techniques cannot be potentially implemented to presented intended use due to the following issues: 1) Video artifacts and technology principles limit micro-saccadic and vergence related data acquisition and analysis; 2) High demand for computing power and energy; and 3) Bulky hardware design and limited usability.

Refractive errors assessment method principles: Nowadays, most common refraction procedures consist of two methods: 1) A subjective refraction where the result depends on the patient's ability to discern changes in clarity. This process relies on the cooperation of the patient. 2) An objective refraction (usually retinoscopy) where the result depends purely on the examiner's judgement to determine the optimum optical correction. An autorefractor (can also be used to obtain an objective refraction.

Subjective refraction consists of three distinct phases. The first is designed to correct the spherical element of the refractive error in such a way as to facilitate the accurate determination of any astigmatic element present. It should be remembered that, although astigmatism is often present, a refractive error may be entirely spherical. The second phase is the determination of the astigmatic error and the third phase involves the balancing and/or modification of the refractive correction to ensure optimal visual performance and patient comfort. As always, the patient's history and symptoms are important and can be used to help predict a refractive error.

Objective refraction Objective refraction (retinoscopy) is often used to determine the initial spherical element of refraction. However, when a patient has a recent correction that is providing good acuity, say 6/9 or better, this can be taken as the starting point.

The purpose of the first phase of a subjective refraction is to determine the best vision sphere (BVS). This can be defined as the most positive (or least negative) spherical lens that provides best visual acuity. During a subjective refraction accommodation must be not be allowed to fluctuate randomly. The eye should be as relaxed as possible so that changes in the accommodative state do not influence the end-result. As the accuracy of any subjective test or routine relies on the individual patient's ability to discriminate and communicate accurately, the potential for error must be kept to a minimum. The ability to discriminate and communicate will varies widely from person to person.

The objective refraction only considers the optical factors. Due to this, the subjective refraction which takes into account both optical and neural factors is used to determine the final optical correction. The subjective refraction is often described as the gold-standard method though the procedure varies widely. The methods used to perform subjective refraction mainly vary in terms of steps used to determine best sphere, usage of duochrome, the technique used to determine cylinder and binocular balance. It has been recommended that subjective refraction can be used as a gold standard when new refractive procedures are assessed if the procedure for subjective refraction is fully described. Apart from the neural factors, the difference between the objective and subjective refraction could also be explained by instrument related factors. Comparing the objective and subjective refraction, the accuracy of objective refraction measurement is shown to be good with open-field view autorefractometers. Instrument myopia can be induced with closed-field view of the autorefractometers and whether there is a fogging step used during autorefractometer measurement. Image quality metrics based on the wavefront data is also widely used to optimize the objective refraction and predict the subjective image quality.

The results of the subjective refraction are important both to the optometrist and to the patient, because most patients judge all aspects of the eyecare they have been provided based on the clarity and comfort of their prescription. In view of this, it is surprising that there is lack of evidence based research on reproducibility of refractive error testing.

The system 10, being the subject of the application, proposes a novel method of refractive errors assessment by means of an evaluation of microsaccadic eye movement patterns triggered by a changeable and controlled dichoptic visual stimuli, following a defined scenario, that utilizes varifocal optics system. The controlled change in optical conditions, combined with an appropriate visual stimulus, makes it possible to determine visual acuity without acquiring a feedback from the patient which is normally used by an optometrist to indicate perception quality of an optotype provided under set optical conditions. Today, optometrists require a phoropter and an optotype board (mostly digital display) placed about 16-20 ft away from the patient. This equipment is fundamental for performing subjective refraction. The patient provides a constant feedback to the optometrist, e.g. by reading letters or recognizing patterns that are controlled by an optometrist executing applied routine and associated steps. Recognized optotype with the smallest angular dimensions determines the visual acuity often provided in LogMAR scale. The phoropter provides plurality of optical conditions that simulate, for example, different spectacle lenses. The subjective information indicating the readability or visibility of an optotype provided by the patient during various optical conditions generated by a phoropter is recursively processed by an optometrist until best optical match for refractive errors correction (glasses, contact lenses) is found. Indication of sharp vision concluded on the basis of patient's feedback is replaced in our system by the evaluation of micro-saccadic eye movement patterns indicating whether the patient sees given optotypes sharply or blurred (presented during automatically changeable states of varifocal optics). It translates to a novel approach of conducting refractive errors exams that excludes highest factors of potential errors: unskilled optometrist, perceptual and/or interpersonal issues (e.g. in the youngest children or the elderly).

Vision quality, comfort and sharpness is directly linked to subjective feelings of the patient. Currently, there is no device that is capable of quantization this subjective feeling. However, recent studies highlight possible links between eye movements (especially micro-movements) and visual acuity and comfort. Vision science indicated that intersaccadic drift and tremor movements are tuned during high visual acuity tasks. Additionally, there is scientific conclusion that induced refractive errors (added lenses) impacts eye movements behavior. Those mechanisms are foundations of visual acuity assessment system using tailor-made dual-phase eye tracking module consisting of MEMS mirror and 2D profile sensor. Implementation of this mechanism is performed within disclosed system through unique combination of tailored module responsible for eye behavior analysis and projecting dichoptic stimuli under variable optical conditions. This approach means novel method that can become a gold standard in eye care industry. Nowadays, eye behavior analysis isn't included in regular eye exam. Scientists suggest that value of this component leads to discovering new facts about mechanisms regulating the visual perception and comfort. Disclosed device answers this need in a complete way that can be performed without human involvement (both optometrist and patient). This can be especially important for patients with limited perceptual or communicative abilities, such as children, elderly, mentally or physically impaired patients.

Referring to FIG. 33, the controller 40 may be programmed to execute the algorithm steps shown in method 200 to detect refractive errors. In method 200, the OMAP module of the controller 40 performs the following steps: 1) Initial refractive errors objective determination done by ORA module helps to indicate approximate range of possible optical states to be examined during next refractive assessment recursive part. 2) Adjusting optical conditions impacting visual stimuli perception (independently to the left and right eye) is executed by the controller 40. Action utilizes varifocal optics system adopted in accordance to the initial objective refraction output AND/OR decision-making algorithm output. 3) Adjusting visual stimuli type and features like angular size, contrast, shape, movement trajectory, background is executed (independently to the left and right eye). Action utilizes a display paired to varifocal optics and computational unit (objects rendering) adopted in accordance to the initial objective refraction output AND/OR decision making algorithm output. 4) Acquiring light signal determining retina position within high spatial and temporal by using a combination of data collected through 2D profile sensor and MEMS mirror based eye tracking modules. 5) Acquiring ocular accommodation related light signal describing current state of eye accommodation. 6) Procedure may also include an optional user feedback indicating current perceptual status. It is not mandatory for obtaining the results, however decision making block may include this input to determine the next steps. 7) Ocular behavior analysis is executed. Under this block, system performs classification of eye movement types along with associated quantized parameters. Collected data sets are paired to currently set optical conditions and visual stimuli features provided by varifocal optics and paired display. This part also covers specifying of eye accommodation state that may be used for further proceedings.

8) Decision making block takes into equation pre-processed data calculated from raw light signals, describing current state of eye behavior including: movements characteristics (types and parameters) and accommodation state. Those data stacks are matched with optical conditions and visual stimuli provided within the data acquisition timeframe. Decision making process analyzes changes occurred in calculated data sets caused by adjusted optical state and/or visual stimuli. Differences between those data sets are an input factor defining next steps to be applied during the next iteration (varifocal optics adjustment, visual stimuli adjustment). For most of the cases, system follows a scenario implementing a change in only one stimuli aspects (optical conditions or stimuli visual features) in order to keep data homogeneous and explicit. Decision making block does include procedures based on traditional refraction routines considered as best practices in the range of: sphere determination, astigmatism determination and binocular balance techniques. Each steps are empowered by objectively collected data which enables to lower the number of steps needed for obtaining the end result (like on-going accommodation control). Mostly important is a benchmark between lastly computed two sets of eye behavior collected during two different optical states ("A" and "B"). Comparison of eye responses caused by two different optical states indicates whether best refractive correction is placed inside or outside the analyzed optical range. Block contains also an implementation of a reference model used to estimate best refractive correction conditions depending on all the data collected during previous iterations, so system is capable of predicting whether best correction is placed closer to the optical state "A" or "B". Based on the result, optical range adjustment is determined to be applied during next iteration. System may also include into the next step specific adjustment of varifocal optics (causing f. e. retinal blur) meant to influence eye accommodation state and/or perceptual conditions, once system assessed a necessity to avoid potential result distractor. When it is determined that changes applied in varifocal optics and/or stimuli visual features do not cause with visual acuity improvement (or other tested parameter of visual system), the loop stops. 9) Lastly defined optical state bundled with all previously obtained data are transposed into a prescription-like output allowing to choose preferred correction like glasses or contact lenses.

Additionally, disclosed system allows for improved routine in the following contexts: 1) suiting multifocal or progressive lenses (including simulation of the corrective lens visualizing usability and comfort aspects); 2) Far and near distance visual performance assessment (binocular vision behavior); 3) Contrast sensitivity measurement based on eye movement behavior only; and 4) Indication of visual acuity loss due the saccadic abnormalities may indicate need for deeper proceedings.

Referring to FIG. 34, the controller 40 may also be programmed to execute the algorithm steps shown in method 300 to perform NDD-focused screening tests. NDD-focused screening tests methods principles: the diagnostic device 102 follows a concept of 'eye as a biomarker'. Eye movement abnormalities are among the most common phenotypic manifestations of patients with neurodegenerative diseases. The prominent features include the saccadic abnormalities, fixation instability, and abnormal smooth pursuit. The diagnostic device 102 is designed as system that offers perfect conditions for conducting comprehensive NDD-focused screening test package.

Main system's features supporting this thesis include: 1) Eye tracking tailor-made for eye behavior analysis designed as a combination of MEMS mirror based module and 2D profile sensor module. Eye tracking modules are provided separately for left and right eye. 2) Varifocal optics module able to substitute refractive correction excludes necessity of wearing eyeglasses during the assessment which positively influence eye tracking data quality without negative influence on the patient's visual perception. 3) Device design allows for steady head position while providing isolated, dichoptic conditions of generated visual stimuli. No visual distractor may influence the assessment which is important feature in comparison to scientifically applied approaches utilizing e.g. regular LCD displays. 4) Dichoptic conditions allow to extend stimuli scenarios through adjusting stimuli features to left and right eye independently in a very flexible way which cannot be done with the same effect by using regular LCD display. 5) Visual stimuli scenarios can be adopted to perform cognitive tests assessing features like visual memory. 6) Comprehensive vision benchmark including binocular vision (e.g. stereopsis) and visual acuity may act as additional data set incorporated into the assessment (especially in individual retrospection, progress monitoring mode). 7) System provides heterogeneous data collected through different test types in categories of: ocular movements behavior assessment, vision assessment, cognitive assessment. It is important due to the fact, that NDD symptoms may occur different in individuals. 8) System brakes accessibility barriers through leveraging high social awareness of recursively conducted eye exams. 9) Sharing the technology units for refraction and NDD screening positively influence economics of commercial implementation. 10) Screening methodology is designed as a non-invasive set of tests. 11) Screening methodology is purely based on objectively collected data which excludes potential human error and subjective data disadvantages. 12) Data analytics models consist of two mutually non-exclusive approaches: a) Individual retrospection—mode takes into account previously collected profile and analysis if any significant change occurred. b) Population baseline—mode assumes comparison of the collected profile to the health population baseline and associated prediction models acting as a reference. 13) Available system modes tailored to the use case: a) Standalone screening device—expanding offer of existing points of care. b) Decision support—extended mode that may incorporate detailed tests variants used as a support for disease progression assessment fe. observing response to pharma treatment applied to an individual by a neurologist.

When executing method 300 to perform NDD-focused screening tests, the controller 40 performs the algorithm steps of: 1) Refractive correction excluding necessity of wearing eyeglasses during the screening process is provided, based on user data input and/or conducted refraction assessment (described in section above). 2) Stimuli type and visual features adjustment based on given test scenario and live results. Instructions are dictated by decision making block or initial settings. 3) Collecting eye movements data determining retina position within high resolution of spatial and temporal frames done through combination of 2D profile sensor and MEMS mirror eye tracking module (detailed description of technical principles was disclosed in one of above paragraphs). Additionally, MEMS mirror operating angles may be dynamically narrowed according to test scenario and visual stimuli angular size change. This approach impacts level of precision through increasing the number of retina/iris intersection points (changed density of Lissajous pattern). 4) Scenario related decision if visual stimuli has to be adjusted according to lastly obtained eye behavior outcomes. 5) Once data set is collected and prepared—NDD focused analytics is performed. Depending on device mode, obtained date are compared to individual profile collected during previous assessment(s) and/or obtained data are compared to health population baselines and associated eye behavior prediction models acting as a reference. 6) Decision of ending the assessment relies on reaching defined number of completed tests which may depend on device mode and intended use. 7) An output is provided in the form of indication of possible occurrence of NDD development and/or raw data print for further use.

Recent studies conclude presence of links between eye movement abnormalities and development of particular disorders. Those indications may support comparison between collected data sets to the eye movement prediction models and health population baseline benchmark. However, it is worth to mention that our system collects far more comprehensive set of data in comparison to quoted scientific studies. On this basis, the system 10 implements machine learning-based classification techniques that, for the first time, will include such a complete set of cues related to the possible development of NDDs.

For example, the system 10 may be programed to generate the data file 174 shown in FIG. 35 for use in executing method 300. Referring to data file 174, the character "+" character indicates presence of the abnormality 1 Eye movement abnormalities are mostly not detected clinically (without special eye movement recordings) 2 Especially on self-paced saccades 3 But not always 4 Later on, there is limitation of vertical gaze range. Differential diagnosis of vertical supranuclear gaze palsy include corticobasal degeneration (CBD), frontotemporal dementia (FTD), Kufor-Rakeb syndrome (KRS), Niemann-Pick type C (NPC), neuronal intranuclear inclusion disease, Gaucher's disease, and Whipple's disease 5 In vertical direction; can have round-the-house saccades 6 Prominent 7 In some patients with progressive supranuclear (PSP)-like phenotype 8 Opsoclonus/ocular flutter 9 Horizontal gaze more affected than vertical gaze, as opposed to PSP. Also has impairment in anti-saccade task 10 Anecdotally, eye movements tend to be preserved relatively to motor and psychiatric impairment, as opposed to HD 11 Hypometric vestibulo-ocular reflex 12 Downbeat, gaze-evoked or rebound nystagmus 13 Patients can have alternating skew deviation, gaze-evoked or periodic alternating nystagmus; oculocutaneous telangiectasia (not always); elevated alpha-fetoprotein (AFP) 14 Oculomotor apraxia 15 Elevated AFP Abbreviations: PD, Parkinson's disease; MSA, multiple system atrophy; PSP, progressive supranuclear palsy; OMAS, opsoclonus-myoclonus ataxia syndrome; HD, Huntington's disease; SCA, spinocerebellar ataxia; AT, ataxia-telangiectasia; AOA, ataxia with oculomotor apraxia.

Parkinson disease: Clinical eye abnormalities are subtle, but hypometric horizontal and/or vertical saccades can sometimes be seen.

Multiple system atrophy: Patients can display square wave jerks and saccadic dysmetria.

Progressive supranuclear palsy: Square wave jerks are common. Patients have slow vertical saccades early in the course, and this precedes ophthalmoplegia.

Opsoclonus-myoclonus ataxia syndrome: Opsoclonus is a diagnostic feature.

Huntington disease: The main ocular finding is impairment of saccade initiation. oculomotor findings are an early diagnostic clue. Patients can also have saccadic slowing and an impairment in the antisaccade task.

Spinocerebellar ataxia: Saccades are important diagnostic clues in certain types of SCA, as slowing of saccades on horizontal gaze is a hallmark clinical feature of SCA2. Macrosaccadic oscillations are seen in spinocerebellar ataxia with saccadic intrusions (SCASI).

Friedreich ataxia: Prominent fixation instability may cause macrosaccadic oscillations or continuous square wave jerks.

Oculomotor apraxia: Delayed initiation of saccades due to impaired higher cortical control. Patients may employ head thrusts or eye blinks to generate saccades.

Ataxia-telangiectasia: Hypometric saccades, alternating skew deviation, and square wave jerks can be seen.

Visual Task Scenarios. In some embodiments, the OMAP module of the controller 40 may be programmed to provide visual tasks that are designed to drive and assess all crucial features of eye movements (e.g. saccades, smooth pursuits, fixation, OKN). Some of the stimulus are also extended through dichoptic elements designed to induce selected aspects of binocular behavior or to separate monocular and binocular ocular movement strategies. Some of the stimulus may also use varifocal optics to drive depth perception or convergence. However, varifocal optics module is mostly important here to reduce necessity of wearing corrective glasses during the assessment which reduces the possible entry barriers and impacts eye tracking data quality level. Additionally, proposed stimulation does include tasks related to visuospatial skills, cognition and visual memory. Precise ocular movement analysis conducted during those activities translates to a major added value to overall test results.

Mechanics of those exercises are mostly based on the holding or directing user's gaze onto selected attention objects defined by a task scenario. User input may be composed of gaze tracking and decision based input (e.g. hand controller, set of buttons). FIG. 36 illustrates sets of frames illustrating selected principles behind the visual stimulation. Final form is provided as an interactive, animated set of visual tasks. Proposed set of tasks bundled with scientific-grade data acquisition models, dichoptic view conditions and optically controlled depth plan creates best possible conditions for ocular movement based biomarking.

Visual stimuli scenarios included in OMAP module are designed to evoke and analyze listed below types of eye movements and behaviors within variable and controlled perceptual and visual conditions.

Prosaccades—Prosaccades involve the simple redirection of gaze to a stimulus and typically are generated to align the fovea with visual targets of interest. These are visually-guided saccades that do not involve complex volitional processes.

Express saccades—Express saccades are very short latency reflex-like eye movements that are mediated by direct pathways from the retina or visual cortex to the superior colliculus. These saccades bypass the more time-consuming, extensive processing from the frontal cortex, and can be produced under laboratory circumstances. They occur when a "gap" is inserted between the extinction of a fixation point and the appearance of a peripheral stimulus.

Predictive saccades—Predictive saccades occur when gaze is fixated on a target moving in a temporally or spatially predictive manner (such as when following a fast-moving object with one's eyes).

Memory-guided saccades—Memory-guided saccades occur when the eyes move toward a remembered point with a prior visual stimulus. Implementation of a memory guided saccade requires basic oculomotor control, dorsolateral prefrontal cortex, anterior cingulate, and supplementary eye field. Deficits are related to frontal functioning.

Anti saccades—Antisaccades are eye movements that are an intentional shift of gaze away from a visual stimulus. Implementation of an antisaccade requires the top-down inhibition of a reflexive saccade to the target location, as well as the execution of a voluntary eye movement to the mirror location of the target. Directional errors can therefore be linked to frontal lobe dysfunctions, Saccade sequencing—Saccade sequencing occurs when subjects generate saccades to memorized targets in a learned order. Errors may be linked to supplementary eye fields, which are important for motor sequence learning, or to the frontal eye fields, posterior parietal cortex, or the anterior cingulate cortex.

Microsaccades—Microsaccades are saccades that range from about 0.01°-0.3° in amplitude and are unconsciously generated during fixation. They appear to correct for fixation errors from slow eye drifts and may prevent fading of the visual scene, which can occur when the image is stabilized on the retina. Microsaccades are suppressed during tasks requiring fine visual discrimination.

Ocular micro tremor—Ocular microtremor is a constant, physiological tremor of the eye of high frequency and low amplitude. It occurs in all normal humans, even when the eye is apparently stationary, and results from the continuous activity of brainstem oculomotor units.

Intersaccadic drift—fixational eye movement characterized by a smoother, slower, roaming motion of the eye when fixed on an object. The exact movement of ocular drift is often compared to Brownian motion, which is the random motion of a particle suspended in fluid as a result of its collision with the atoms and molecules that comprise that fluid. The movement can also be compared to a random walk, characterized by random and often erratic changes in direction. Ocular drifts occur incessantly during intersaccadic fixation. Although the frequency of ocular drifts is usually lower than the frequency of ocular microtremors (from 0 to 40 Hz compared to from 40 to 100 Hz), it is problematic to distinguish ocular drifts and ocular microtremors. In fact, microtremors might reflect the Brownian engine underlying the drift motion. Resolution of intersaccadic eye movements is technically challenging.

Optokinetic nystagmus—Optokinetic nystagmus/response (OKN/R) is nystagmus that occurs in response to a visual stimulus on the retina. It is present in normally developed patients. The optokinetic response allows the eye to follow objects in motion when the head remains stationary (e.g., observing individual telephone poles on the side of the road as one travels by them in a car, or observing stationary objects while walking past them).

Smooth pursuits—Slow, continuous eye movement that is responsive to feedback provided by brain regions involved in processing visual information, thus enabling continuous fixation on a moving object.

Fixation strategy—Optimizing attention to two spatially distinct objects. Assuming the two objects require attention nearly simultaneously, subjects either could fixate one object or they could fixate between the objects.

Fixation stability—Several definitions, measurements, and implicit meanings of 'fixation stability' have been used in clinical vision research, leading to some confusion. One definition concerns eye movements observed within fixations (i.e., within periods separated by saccades) when observing a point target: drift, microsaccades and physiological tremor all lead to some degree of within-fixation instability. A second definition relates to eye position during multiple fixations (and saccades) when patients fixate a point target. Increased between fixation variability, combined with within-fixation instability, is known to be associated with poorer visual function in people with retinal disease such as age-related macular degeneration.

Saccades detailed characteristics:

Amplitude—the size of the saccade, usually measured in degrees or mins. of arc. The amplitude determines the saccade accuracy. This is sometimes denoted using "gain". The gain is the ratio of the actual saccade amplitude divided by the desired saccade amplitude (usually determined by the size of a target step). Gains of <1 indicate the saccade was too small or hypometric; gains of >1 indicate the saccade was too large or hypermetric. A number of congenital conditions, diseases lesions or drugs cause saccade dysmetria (saccades of the wrong size) to a lesser or greater extent.

Peak Velocity—this is the highest velocity reached during the saccade. Saccade velocity profiles are usually symmetrical at least for small and medium size saccades. So, determining the peak is usually straight forward. In some conditions while the size of saccades remains reasonably accurate, the saccade velocity is greatly reduced—so-called slowed saccades.

Duration—the time taken to complete the saccade. This is most easily measured from the velocity profile. Partly because of the high velocities involved, most saccades are complete within a few tens of milliseconds (ms). As it takes about 80 ms for visual information to reach the visual cortex, these short durations mean that saccades cannot be modified "in-flight" by visual information. If a target moves, new information is used to trigger a corrective saccade.

Latency—this is the time taken from the appearance of a target to the beginning of a saccade in response to that target. Whereas the other parameters tend to fall in a narrow range for a given set of circumstances, latency is extremely variable. The latency for most medium amplitude saccades) (5°-10° is usually around 200 ms. However, it can be as low as 100 ms, or as high as 350 ms. The distribution of saccade latency has attracted a great deal of attention recently, as it may indicate alterations in processing in the oculomotor system above the level of the brainstem and superior colliculus."

Smooth pursuits characteristics:

Smooth pursuit can also be assessed in term of its parameters. However, pursuit parameters are more difficult to measure and are not as stereotyped as for saccades. Pursuit consists of two phases—initiation and maintenance. Measures of initiation parameters can reveal information about the visual motion processing that is necessary for pursuit. Maintenance involves the construction of an internal, mental, representation of target motion, and the use of this to update and enhance pursuit performance.

Smooth pursuit is when the eye is following a moving target. It is typically in the range of 10 deg/s to 30 deg/s [Holmqvist et al., 2011] but it can reach up to 100 deg/s Meyer et al. [1985] but those movements typically consists of both smoothpursuit and saccades termed catch-up saccades.

Initial acceleration—this is the rate of change of the eye velocity. The first 20 ms or so of pursuit tends to be the same regardless of target parameters. However, for the next 80 ms or so, target speed and position has a large effect on acceleration. The first 100 ms of pursuit is open-loop; no visual feedback is available because of the delays in the visual system. Thereafter, visual feedback is available to close the loop, and other sources of information are also available to improve performance.

Peak velocity—After pursuit initiation, velocity usually rises to a peak and then either declines slightly or oscillates around the target velocity. This peak velocity can be used to derive a value for gain (peak velocity/target velocity). It is usually near the velocity of the target.

Velocity at set time points—Instead of using peak velocity, it is also sometimes of interest to use measures of velocity at particular times relative to either target appearance or pursuit initiation. Eye velocity up to 100 ms after target appearance can be used as a measure of prediction or anticipation. Velocity measured 100 ms after pursuit begins reveals something about the ability of pursuit system in the absence of visual feedback. Peak velocity usually occurs several hundred milliseconds after pursuit initiation.

Latency—the time from target appearance to the beginning of pursuit. The difficulty here is defining when pursuit begins. Usually it is measured from traces of eye velocity. While it can be judged by eye, it is often calculated by finding the intersection between two regression functions one fitted to velocity about the time of target appearance, and the second fitted over the initial part of the pursuit response.

Binocular vision related components included in OMAP:

Vergence—A vergence is the simultaneous movement of both eyes in opposite directions to obtain or maintain single binocular vision. When a creature with binocular vision looks at an object, the eyes must rotate around a horizontal axis so that the projection of the image is in the centre of the retina in both eyes.

Binocular fusion—The ability to maintain visual focus on an object with both eyes, creating a single visual image. Lack of binocular vision is normal in infants. Adults without binocular vision experience distortions in depth perception and visual measurement of distance.

Binocular rivalry—The oscillating perception of first one then the other of two visual stimuli which differ radically in color or form when they are presented simultaneously to congruent areas of both eyes.

Perceptual components included in OMAP (cognitive assessment results paired with ocular behavior data): Visual memory—ability to remember or recall information such as activities, pictures or words that have been viewed in the past. Short-term visual memory is the ability to recall images that have just been viewed. Visual spatial perception—The Visual-Spatial Perception is the ability to recognize an object's physical location as well as the physical relationships between objects.

In some embodiments, the diagnostic device 102 is configured for use in performing refractive errors assessment and neurodegenerative disorders screening. The diagnostic device 102 includes a display 108 configure to render dynamically adjusted, binocular, and/or dichoptic visual stimuli to a user, a varifocal optics system 54 orientated between the display and the user's eyes, an ocular reflex analyzer 104 emitting light signals towards the user's eye s and obtaining light signal reflected from selected part of the eye to measure eye accommodation during an on-going visual stimulation, and an eye tracking system 52 configured to track movement of the user's eyes.

The varifocal optics system may include a pair of metalenses, each metalens being associated with a corresponding eye of the user. The varifocal optics system may include a first set of metalenses associated with a first eye of the user and a second set of metalenses associated with a second eye of the user, each set of metalenses including at least one tunable metalens. The varifocal optics system includes a pair of tunable liquid-membrane lenses, each tunable liquid-membrane lens being associated with a corresponding eye of the user.

The ocular reflex analyzer may include a projection assembly including a near-infrared (NIR) marker projecting module configured to produce an image marker on both a retina and a cornea of the eye. The ocular reflex analyzer may also include an acquisition assembly is configured to perform detection of the image marker produced by the projection assembly. The ocular reflex analyzer may also include a light emitter configured to emit light to obtain retinal reflex of the user's eye, a sensor configured to receive reflected light from the user's eye and record the retinal reflex of the user's eye, a NIR sensor configured to receive reflected light from the user's eye and record the cornea reflex of the user's eye, a hot mirror configured to reflect the light emitted from the light emitter towards the user's eye and reflect the reflected light from the user's eye towards the sensor, and a varifocal optics for image synthesis of the measurement marker from retina and cornea reflex of the user's eye. The ocular reflex analyzer may also include a beam splitter orientated to reflect the light emitted from the light emitter towards the hot mirror and pass the reflected light from the hot mirror towards the sensor.

The eye tracking system may include a micro-electromechanical systems (MEMS) sensor assembly for tracking a position of the user's eyes. The MEMS sensor assembly may include a laser diode for emitting a beam of light, a light detector configured to detect reflected light from the user's eye, and an oscillating micro-mirror configured to reflect the light emitted from the laser diode towards the user's eye and reflect radiation from the user's eye towards the light detector. The MEMS sensor assembly may also include a beam splitter orientated to reflect the beam of light from the laser diode towards the oscillating micro-mirror and pass the reflect radiation received from the oscillating micro-mirror towards the light detector. In some embodiments, the eye tracking system may also include a 2D profile sensor for providing temporal features of eye movements based on retina position.

The diagnostic device 102 may also include a processor that is programmed to perform a neurodegenerative disease screening exam by executing an algorithm including the steps of adjusting the varifocal optics system to an initial refractive correction, displaying visual stimuli on the display based on desired test scenario, collecting eye movement data using eye tracking system, and determining neurodegenerative disease by comparing collected eye movement data with baseline eye movement data associated with desired test procedure. The processor may also be programmed to execute the algorithm including the steps of adjusting the visual stimuli based on collected eye movement data, collecting subsequent eye movement data in response to adjusted visual stimuli, and determining indication of neurodegenerative disease by comparing collected eye movement data with baseline eye movement data associated with desired test scenario.

The processor may also be programmed to perform a refractive errors assessment by executing an algorithm including the steps of operating the varifocal optics system to adjusting optical conditions to an initial refractive error correction (initial refractive correction may be provided as an additional input to the system., for example, in NDD context, it is used to exclude necessity for wearing corrective glass (it could be a potential distractor for eye tracking)), displaying visual stimuli on the display based on desired refractive errors assessment test procedure, collecting eye movement data using eye tracking system, collecting ocular accommodation data using the ocular reflex analyzer, and determining ocular behavior and best refractive correction based on collected eye movement data and ocular behavior data. The processor may also be programmed to execute the algorithm including the steps of adjusting optical conditions and/or visual stimuli, collecting subsequent eye movement data and ocular accommodation data in response to adjusted optical conditions and/or visual stimuli, and determining ocular behavior based on the subsequent eye movement data and ocular accommodation data.

Figure 42:
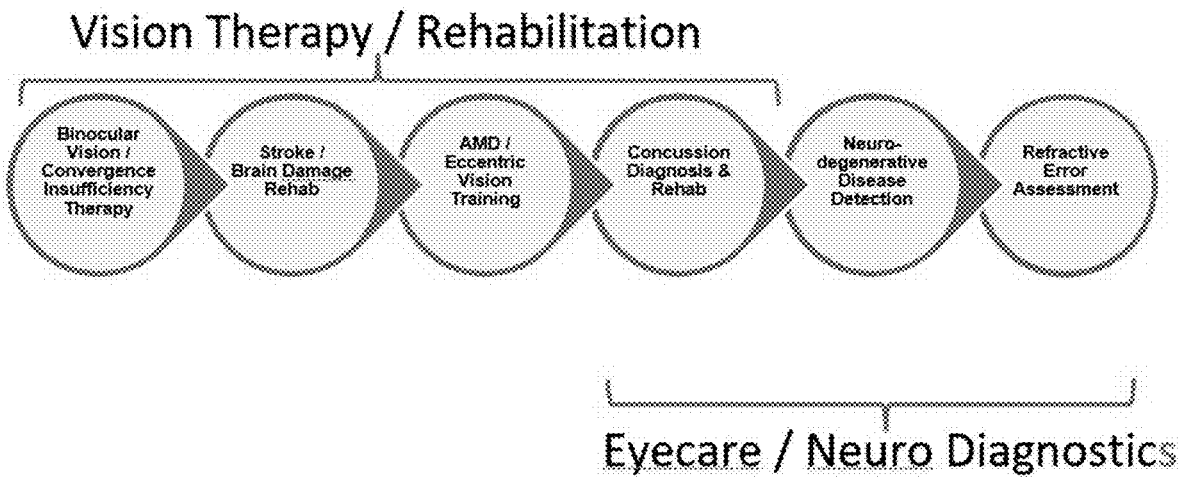
FIGS. 42-43 illustrates some of the use cases that may be performed using the system shown in FIGS. 3 and 18.

Referring to FIG. 42, in some embodiments, the system 10 may be used for binocular vision disorders allowing for vision therapy sessions carried at home under remote specialist's supervision utilizing tailored telemedical features and simplified device design allowing for scalable implementation addressing market price sensitivity levels. The system 10 additionally contains variation adjusted to the vision therapy and assessment provide at specialized eye care units (e.g. vision therapy clinic). Apart from amblyopia and strabismus therapeutic capabilities that are major use cases within vision therapy sector, human visual system performance is often impaired by NDD development or brain injury caused by e.g. stroke, accident. Additionally, the system 10 may be adjusted for home use may also provide cognitive training supporting NDD treatment. Serving this group of patients means important part of the platform concept merging all intended use cases under one, consistent hardware and software ecosystem.

Figure 43:
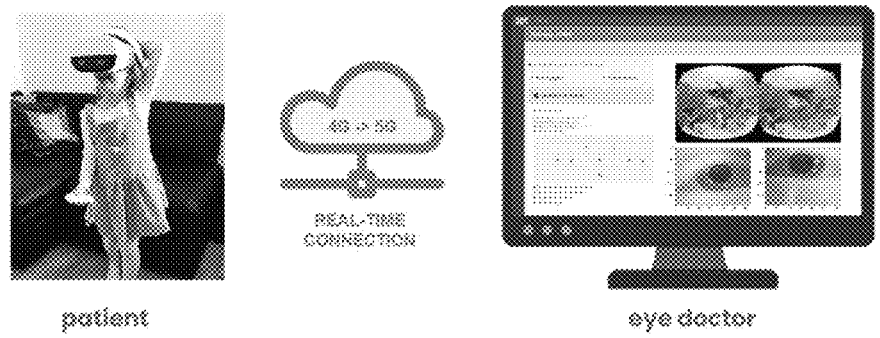

Referring to FIG. 43, the system 10 provides Telemedical aspects—Substitute for sessions conducted at the clinic. Tele-presence tool for specialists increasing attractiveness of home-based therapy. Those sessions may help to evaluate if patient is following the prescribed therapy routine in a fully compliant way. An outcome related to this topic is also additional decision factor influencing changes in adjustment of daily home therapies plan. Remote sessions can be performed within chosen time periods (like once a month). Real time specialist's supervision with real-time data transfer between therapist and patient including: Voice connection; Visual stimuli scenario chose and parameters adjustment done in real time through the specialist's dashboard; Eye movements image stream to the specialist's dashboard; Gaze point data combined with the visual scenario; and Headset display stream to the specialist's dashboard.

For example, in some embodiments, the system 10 may exclude the accommodation measurement module as this is not mandatory for therapy and increases overall costs. In addition, the system 10 may exclude the MEMS/2D-profile CMOS eye tracking and include a video camera eye tracking module mounted, which provides sufficient quality for the therapy while keeping reasonable price/value balance.

Figure 44:
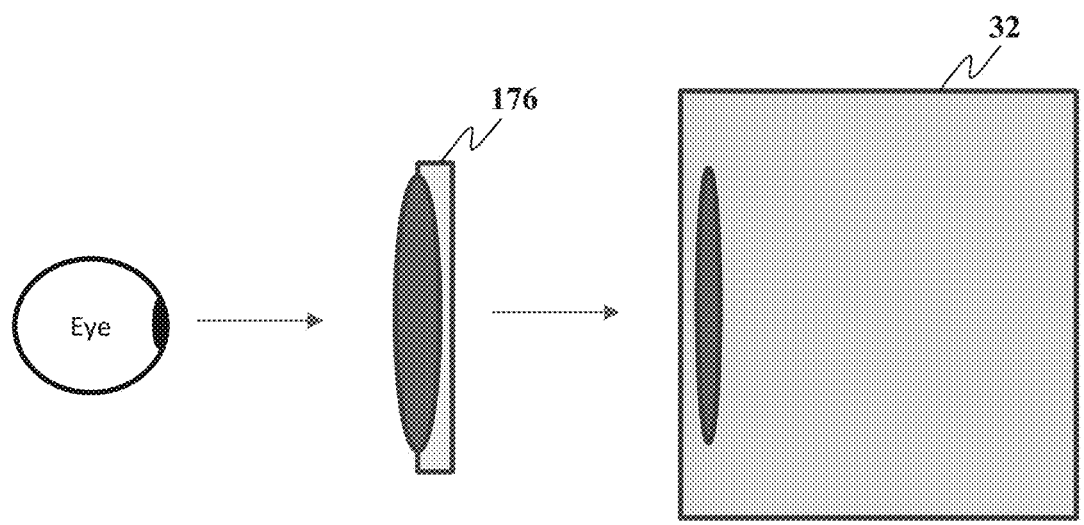
FIG. 44 is a schematic diagram of a portion of the system shown in FIG. 3.

Referring to FIG. 44, in some embodiments the system 10 may replace the varifocal optics assembly by adjusting the depth plane by a static component 176 placed in the front of the headset 32 that contains optical lenses referring to visual training scenario. Module may also act as a substitution for refractive glasses while lenses can be customized to the patient. Module can be manually mounted on the HMD. Lenses mounted in the module are changeable, those can be replaced according to individual disorder parameters and therapy plan. Each therapy assigned to the patient may incorporate a few optical sets to be changed by a parent/guardian between the sessions.

The system 10 may also include specific camera eye tracking features including: 1) Control of eye alignment and real-time stimuli adjustment (virtual prism adjustment according to stability of eye alignment—in case of eyes misalignment, system be able to correct stimuli projection to maintain desired eye alignment defined by the therapeutic adjusted game scenario. 2) Control of vergence/fusion during the therapy and real-time fusion threshold control (disparity between the objects projected in front of the right and left eye may increase until system determines that fusion is broken—it is visible as specific unvoluntary eye movements that are different comparing to the eye movements obtained during correct training range of stimuli. 3) Training stimulating smooth pursuits and saccades with on-going assessment of saccades number, accuracy and pursuits continuity. Visual acuity loss may be diagnosed through diagnostic device embodiment as an effect of fixational eye movements impairment. This can be treated during the home training which creates complete healthcare chain: from diagnosis to therapy. 4) Dynamic blurring/decreasing image quality/adjusting visual parameters of the gaze-dependent VR environment part addressing central vision only. It means dynamic filters added to the stimuli that follow gaze point and project different visuals for amblyopic and non-amblyopic eye. It may be also used to dynamically adjust any kind of static videos/content like 360, VR cartoons. 5) Control of the eyes opened—in some cases of simultaneous perception training it can be possible cheated through closing of fellow eye during the session. Patient has to have both eyes opened during the session. Content may stop if system detects cheating (e.g. too frequent blinking, complete or partial closure of the eye). 6) Reports merging eye movement performance and gamified results paired to given stimuli conditions create perfect data set describing therapy progress (in the form of printed PDF for parents or available via a web browser or in a dedicated user application). Those data sets are also used for therapy adjustment done by AI software between the sessions. 7) Automated training for visual field loss based on dynamic visual field assessment conducted during the training (e.g. scotoma occurred poststroke). Objects positions can be adjusted according to observed gaze reactions in assessed lack of visual field. System may provide with strong visual stimuli to the inactive parts of visual field implementing threshold increase with controlled gaze reactions. 8) Nystagmus control training with added sound cues under provided visual stimuli. 9) Perception integration training combining visual, motor and sound cues and exercises provided by the system as a part of functional/behavioral vision training addressing real world environment and conditions. 10) Set of separate vision assessment and therapy progress monitoring focused activities including: a) visual acuity test done through preferential looking tests; b) visual acuity test evoking optokinetic nystagmus with nystagmus amplitude measurement paired to stimuli parameters; and c) virtual implementation of cover test (eye alignment).

Figure 45:
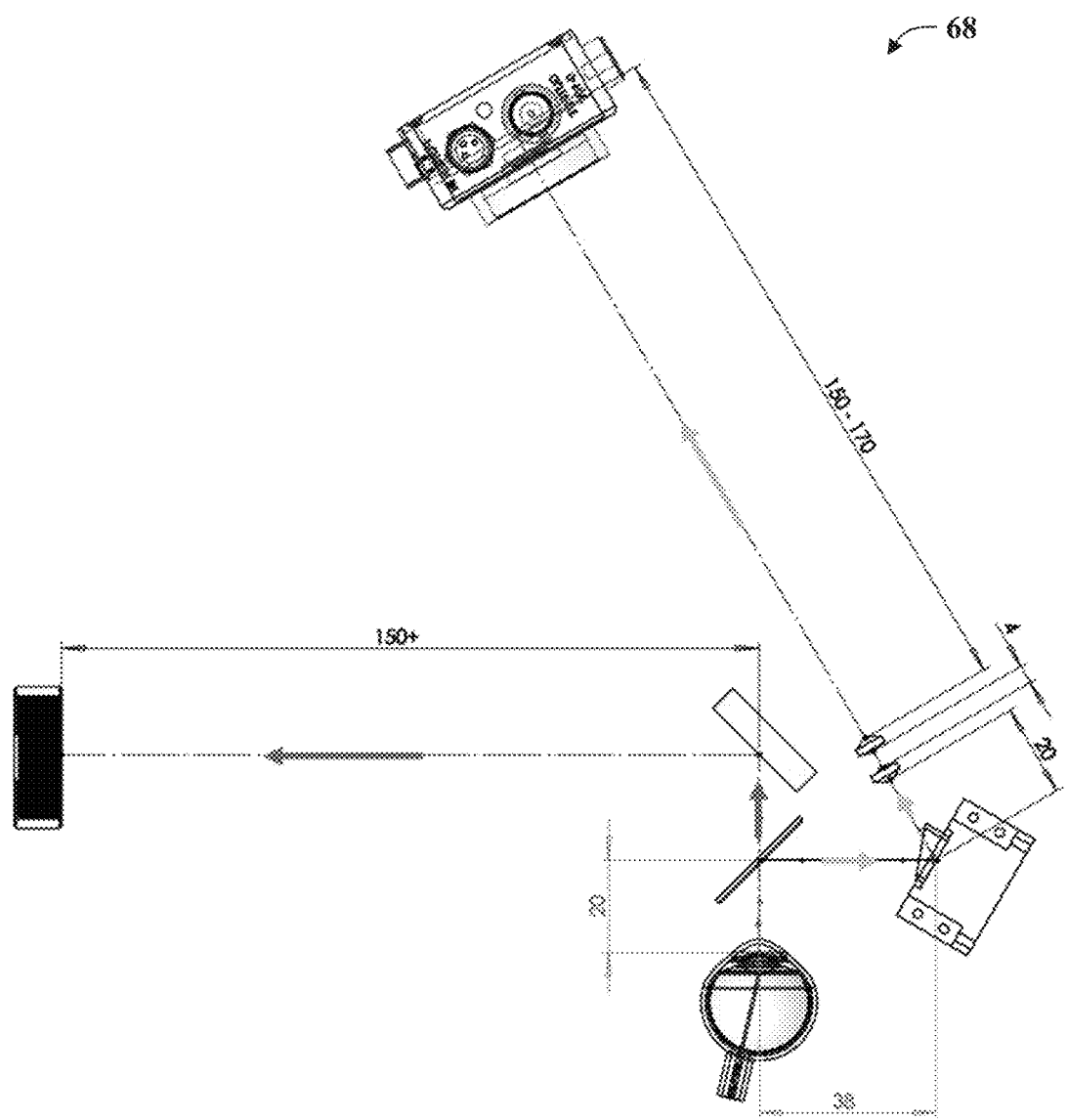
FIG. 45 is a schematic diagram of a 1VIEMS scanning system with an accommodative stimulus.

Referring to FIG. 45, in some embodiments, the MEMS based eye tracking assembly 68 may be based on scanning the eyeball with constant LED lighting and an accommodative stimulus. Referring to FIG. 42 in this setup, the subject observes an accommodative stimulus at a given distance. It maintains a constant eye position. Through a beam splitter, a MEMS mirror scans the area of the eye. A stationary LED light is placed directionally in front of the eye (e.g., above the beam divider assembly).

Any combination of one or more computer-usable or computer-readable media (or medium) may be utilized. For example, a computer-readable media may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis. The term "coupled" means any suitable communications link, including but not limited to the Internet, a LAN, a cellular network, or any suitable communications link. The communications link may include one or more of a wired and wireless connection and may be always connected, connected on a periodic basis, and/or connected on an as needed basis.

A controller, computing device, server, or computer, such as described herein, includes at least one or more processors or processing units and a system memory (see above). The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

What is claimed is:

1. A diagnostic device for use in performing refractive errors assessment and neurodegenerative disorders screening, comprising:
   a display configure to render dynamically adjusted, binocular or dichoptic visual stimuli to a user;
   a varifocal optics system orientated between the display and the user's eyes, the varifocal optics system including a pair of metalenses, each metalens being associated with a corresponding eye of the user;
   an ocular reflex analyzer emitting light signals towards the user's eyes and obtaining light signal reflected from selected part of the eye to measure eye accommodation during an on-going visual stimulation; and
   an eye tracking system configured to track movement of the user's eyes.

2. The diagnostic device of claim 1, further comprising a processor programmed to performing a neurodegenerative disease screening exam by executing an algorithm including the steps of:
   adjusting the varifocal optics system to provide an initial refractive error correction;
   displaying visual stimuli on the display based on desired test procedure;
   collecting eye movement data using eye tracking system; and
   determining neurodegenerative disease by comparing collected eye movement data with baseline eye movement data associated with desired test scenario.

3. The diagnostic device of claim 2, wherein the processor is programmed to perform a refractive errors assessment by executing an algorithm including the steps of:
   displaying visual stimuli on the display based on desired refractive errors assessment test procedure;
   collecting eye movement data using eye tracking system;
   collecting ocular accommodation data using the ocular reflex analyzer; and
   determining ocular behavior and best refractive correction based on collected eye movement data and ocular behavior data.

4. The diagnostic device of claim 1, wherein the varifocal optics system includes a first set of metalenses associated with a first eye of the user and a second set of metalenses associated with a second eye of the user, each set of metalenses including at least one tunable metalens.

5. The diagnostic device of claim 1, wherein the varifocal optics system includes a pair of tunable liquid-membrane lenses, each tunable liquid-membrane lens being associated with a corresponding eye of the user.

6. The diagnostic device of claim 1, wherein the ocular reflex analyzer includes a projection assembly including a near-infrared (NIR) marker projecting module configured to produce an image marker on both a retina and a cornea of the eye.

7. The diagnostic device of claim 6, wherein the ocular reflex analyzer includes an acquisition assembly is configured to perform detection of the image marker produced by the projection assembly.

8. The diagnostic device of claim 1, wherein the ocular reflex analyzer includes:
   a light emitter configured to emit light to obtain retinal reflex of the user's eye;
   a sensor configured to receive reflected light from the user's eye and record the retinal reflex of the user's eye;
   a NIR sensor configured to receive reflected light from the user's eye and record the cornea reflex of the user's eye;
   a hot mirror configured to reflect the light emitted from the light emitter towards the user's eye and reflect the reflected light from the user's eye towards the sensor; and
   a varifocal optics for image synthesis of the measurement marker from retina and cornea reflex of the user's eye.

9. The diagnostic device of claim 8, wherein the ocular reflex analyzer further includes a beam splitter orientated to reflect the light emitted from the light emitter towards the hot mirror and pass the reflected light from the hot mirror towards the sensor.

10. The diagnostic device of claim 1, wherein the eye tracking system includes a micro-electro-mechanical systems (MEMS) sensor assembly for tracking a position of the user's eyes.

11. The diagnostic device of claim 10, wherein the MEMS sensor assembly includes:
   a laser diode for emitting a beam of light;
   a light detector configured to detect reflected light from the user's eye; and
   an oscillating micro-mirror configured to reflect the light emitted from the laser diode towards the user's eye and reflect radiation from the user's eye towards the light detector.

12. The diagnostic device of claim 11, wherein the MEMS sensor assembly further includes a beam splitter orientated to reflect the beam of light from the laser diode towards the oscillating micro-mirror and pass the reflect radiation received from the oscillating micro-mirror towards the light detector.

13. The diagnostic device of claim 10, wherein the eye tracking system further includes a 2D profile sensor for providing temporal features of eye movements based on retina position.

14. A method of operating a diagnostic device for performing a neurodegenerative disease screening exam, the diagnostic device including a display configure to render dynamically adjusted, binocular or dichoptic visual stimuli to a user, a varifocal optics system orientated between the display and the user's eyes, an eye tracking system configured to track movement of the user's eyes, and a processor, wherein the eye tracking system includes a MEMS sensor assembly for eye movements spatial parameters determination and a 2D profile sensor for eye movements spatial parameters determination, the method including the processor executing the algorithm steps of:
   adjusting the varifocal optics system to an initial refractive correction;
   displaying visual stimuli on the display based on desired test procedure;
   collecting eye movement data using eye tracking system; and
   determining neurodegenerative disease by comparing collected eye movement data with baseline eye movement data associated with desired test scenario.

15. The method of claim 14, wherein the processor executes the algorithm step of:
   adjusting the visual stimuli based on collected eye movement data;
   collecting subsequent eye movement data in response to adjusted visual stimuli; and
   determining indication of neurodegenerative disease by comparing collected eye movement data with baseline eye movement data associated with desired test scenario.

16. A method of operating a diagnostic device for performing a refractive errors assessment, the diagnostic device including a display configure to render dynamically adjusted, binocular or dichoptic visual stimuli to a user, a varifocal optics system orientated between the display and the user's eyes, an ocular reflex analyzer emitting light signals towards the user's eye s and obtaining light signal reflected from selected part of the eye to measure eye accommodation during an on-going visual stimulation, an eye tracking system configured to track movement of the user's eyes, and a processor, wherein the eye tracking system includes a MEMS sensor assembly for eye movements spatial parameters determination and a 2D profile sensor for eye movements spatial parameters determination, the method including the processor executing the algorithm steps of:
   displaying visual stimuli on the display based on desired refractive errors assessment test procedure;
   collecting eye movement data using eye tracking system;
   collecting ocular accommodation data using the ocular reflex analyzer; and
   determining best refractive correction and ocular behavior based on collected eye movement data and ocular behavior data.

17. The method of claim 16, wherein the processor executes the algorithm step of:
   adjusting optical conditions and/or visual stimuli;
   collecting subsequent eye movement data and ocular accommodation data in response to adjusted optical conditions and/or visual stimuli; and
   determining ocular behavior based on the subsequent eye movement data and ocular accommodation data.

* * * * *